(12) United States Patent
Ogita et al.

(10) Patent No.: US 10,535,823 B2
(45) Date of Patent: *Jan. 14, 2020

(54) COMPOSITE MATERIAL, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Kaori Ogita, Isehara (JP); Hiromi Nowatari, Atsugi (JP); Harue Osaka, Sagamihara (JP); Takahiro Ushikubo, Ashikaga (JP); Satoshi Seo, Sagamihara (JP); Takako Takasu, Chigasaki (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,480

(22) Filed: Oct. 25, 2018

(65) Prior Publication Data

US 2019/0067586 A1    Feb. 28, 2019

Related U.S. Application Data

(63) Continuation of application No. 15/819,231, filed on Nov. 21, 2017, now Pat. No. 10,121,972, which is a continuation of application No. 15/198,244, filed on Jun. 30, 2016, now Pat. No. 9,831,435, which is a continuation of application No. 13/419,863, filed on Mar. 14, 2012, now Pat. No. 9,385,328.

(30) Foreign Application Priority Data

Mar. 23, 2011  (JP) ................................ 2011-064629
May 31, 2011   (JP) ................................ 2011-122829

(51) Int. Cl.
| | | |
|---|---|---|
| H01L 51/54 | (2006.01) | |
| C09K 11/06 | (2006.01) | |
| H01L 51/00 | (2006.01) | |
| H05B 33/14 | (2006.01) | |
| C07F 15/00 | (2006.01) | |

(52) U.S. Cl.
CPC ...... *H01L 51/0052* (2013.01); *C07F 15/0033* (2013.01); *C09K 11/06* (2013.01); *H01L 51/0058* (2013.01); *H01L 51/0085* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1092* (2013.01); *H01L 51/0072* (2013.01)

(58) Field of Classification Search
CPC ..... C07F 15/0033; H05B 33/14; C09K 11/06; C09K 2211/00; C09K 2211/10; C09K 2211/1003; C09K 2211/1011; C09K 2211/1014; C09K 2211/1018; C09K 2211/1022; C09K 2211/1029; C09K 2211/1044; C09K 2211/1007; C09K 2211/1092; C09K 2211/18; C09K 2211/185; H01L 51/0032; H01L 51/005; H01L 51/0052; H01L 51/0054; H01L 51/0058; H01L 51/0062; H01L 51/0072; H01L 51/0074; H01L 51/0085; H01L 51/50; H01L 51/5012; H01L 51/5016; H01L 51/5048; H01L 51/5056; H01L 51/5088
USPC ....... 428/690, 691, 917, 411.4, 336; 427/58, 427/66; 313/500–512; 257/40, 88–104, 257/E51.001–E51.052, 500, 519.3; 252/301.16–301.35
See application file for complete search history.

(56) References Cited

U.S. PATENT DOCUMENTS

| | | |
|---|---|---|
| 5,989,737 A | 11/1999 | Xie et al. |
| 6,013,384 A | 1/2000 | Kido et al. |
| 6,361,886 B2 | 3/2002 | Shi et al. |
| 6,423,429 B2 | 7/2002 | Kido et al. |

(Continued)

FOREIGN PATENT DOCUMENTS

| | | |
|---|---|---|
| EP | 1351558 A | 10/2003 |
| EP | 1478025 A | 11/2004 |

(Continued)

OTHER PUBLICATIONS

Tokito.S et al., "Metal Oxides as a Hole-Injecting Layer for an Organic Electroluminescent Device", J. Phys. D: Appl. Phys. (Journal of Physics D: Applied Physics), Nov. 14, 1996, vol. 29, No. 11, pp. 2750-2753.

(Continued)

*Primary Examiner* — Andrew K Bohaty
(74) *Attorney, Agent, or Firm* — Robinson Intellectual Property Law Office; Eric J. Robinson

(57) ABSTRACT

A composite material which includes an organic compound and an inorganic compound and has a high carrier-transport property is provided. A composite material having a good property of carrier injection into an organic compound is provided. A composite material in which light absorption due to charge-transfer interaction is unlikely to occur is provided. A composite material having a high visible-light-transmitting property is provided. A composite material including a hydrocarbon compound and an inorganic compound exhibiting an electron-accepting property with respect to the hydrocarbon compound is provided. The hydrocarbon compound has a substituent bonded to a naphthalene skeleton, a phenanthrene skeleton, or a triphenylene skeleton and has a molecular weight of 350 to 2000, and the substituent has one or more rings selected from a benzene ring, a naphthalene ring, a phenanthrene ring, and a triphenylene ring.

12 Claims, 32 Drawing Sheets

(56) References Cited

U.S. PATENT DOCUMENTS

| | | | |
|---|---|---|---|
| 6,486,601 B1 | 11/2002 | Sakai et al. | |
| 6,589,673 B1 | 7/2003 | Kido et al. | |
| 6,635,364 B1 | 10/2003 | Igarashi | |
| 6,830,829 B2 | 12/2004 | Suzuki et al. | |
| 6,936,961 B2 | 8/2005 | Liao et al. | |
| 6,994,922 B2 | 2/2006 | Suzuki et al. | |
| 7,083,864 B2 | 8/2006 | Igarashi | |
| 7,158,161 B2 | 1/2007 | Gyoutoku et al. | |
| 7,646,010 B2 | 1/2010 | Kawakami et al. | |
| 7,732,808 B2 | 6/2010 | Ikeda et al. | |
| 7,790,296 B2 | 9/2010 | Kawakami et al. | |
| 7,883,788 B2 | 2/2011 | Kawakami et al. | |
| 7,893,427 B2 | 2/2011 | Kumaki et al. | |
| 7,902,374 B2 | 3/2011 | Lin et al. | |
| 8,007,927 B2 | 8/2011 | Lin et al. | |
| 8,017,252 B2 | 9/2011 | Iwaki et al. | |
| 8,048,543 B2 | 11/2011 | Kawakami et al. | |
| 8,080,934 B2 | 12/2011 | Kido et al. | |
| 8,221,905 B2 | 7/2012 | Lin et al. | |
| 8,227,982 B2 | 7/2012 | Iwaki et al. | |
| 8,252,434 B2 | 8/2012 | Iwaki et al. | |
| 8,314,545 B2 | 11/2012 | Tsuji et al. | |
| 8,367,850 B2 | 2/2013 | Ma et al. | |
| 8,421,346 B2 | 4/2013 | Osaka et al. | |
| 8,541,114 B2 | 9/2013 | Iwaki et al. | |
| 8,580,402 B2 | 11/2013 | Lin et al. | |
| 8,586,204 B2 | 11/2013 | Xia et al. | |
| 8,603,644 B2 | 12/2013 | Osaka et al. | |
| 8,614,334 B2 | 12/2013 | Osaka et al. | |
| 8,652,652 B2 | 2/2014 | Brooks et al. | |
| 8,815,419 B2 | 8/2014 | Iwaki et al. | |
| 8,822,708 B2 | 9/2014 | Ma et al. | |
| 8,866,377 B2 | 10/2014 | Adamovich et al. | |
| 8,912,531 B2 | 12/2014 | Ogiwara et al. | |
| 8,921,548 B2 | 12/2014 | Inoue et al. | |
| 9,040,720 B2 | 5/2015 | Osaka et al. | |
| 9,051,344 B2 | 6/2015 | Lin et al. | |
| 9,123,903 B2 | 9/2015 | Lin et al. | |
| 9,133,118 B2 | 9/2015 | Kitamura et al. | |
| 9,153,786 B2 | 10/2015 | Ma et al. | |
| 9,224,968 B2 | 12/2015 | Iwaki et al. | |
| 9,224,976 B2 | 12/2015 | Sugisawa et al. | |
| 9,496,505 B2 | 11/2016 | Nowatari et al. | |
| 9,577,200 B2 | 2/2017 | Ma et al. | |
| 9,590,180 B2 | 3/2017 | Brooks et al. | |
| 9,608,206 B2 | 3/2017 | Brooks et al. | |
| 9,676,717 B2 | 6/2017 | Kitamura et al. | |
| 9,735,377 B2 | 8/2017 | Xia et al. | |
| 9,831,435 B2 * | 11/2017 | Ogita | C09K 11/06 |
| 10,121,972 B2 * | 11/2018 | Ogita | C09K 11/06 |
| 2002/0180349 A1 | 12/2002 | Aziz et al. | |
| 2003/0189401 A1 | 10/2003 | Kido et al. | |
| 2004/0227460 A1 | 11/2004 | Liao et al. | |
| 2005/0025993 A1 | 2/2005 | Thompson et al. | |
| 2005/0064240 A1 | 3/2005 | Mishima et al. | |
| 2005/0084712 A1 | 4/2005 | Kido et al. | |
| 2005/0084713 A1 | 4/2005 | Kido et al. | |
| 2005/0098207 A1 | 5/2005 | Matsumoto et al. | |
| 2005/0106419 A1 | 5/2005 | Endoh et al. | |
| 2005/0170208 A1 | 8/2005 | Yatsunami et al. | |
| 2005/0218396 A1 | 10/2005 | Tsuchiya et al. | |
| 2006/0008740 A1 | 1/2006 | Kido et al. | |
| 2006/0292394 A1 | 12/2006 | Iwaki et al. | |
| 2007/0007516 A1 | 1/2007 | Seo et al. | |
| 2007/0049778 A1 | 3/2007 | Nomura et al. | |
| 2007/0172699 A1 | 7/2007 | Nakashima et al. | |
| 2007/0182317 A1 | 8/2007 | Kido et al. | |
| 2007/0194306 A1 | 8/2007 | Yamazaki et al. | |
| 2007/0200125 A1 | 8/2007 | Ikeda et al. | |
| 2008/0309222 A1 | 12/2008 | Thompson et al. | |
| 2008/0314965 A1 | 12/2008 | Roberts et al. | |
| 2009/0026922 A1 | 1/2009 | Iwaki et al. | |
| 2009/0153034 A1 | 6/2009 | Lin et al. | |
| 2009/0230847 A1 | 9/2009 | Iwaki et al. | |
| 2009/0242877 A1 | 10/2009 | Kondakov | |
| 2009/0317539 A1 | 12/2009 | Shitagaki et al. |
| 2010/0096627 A1 | 4/2010 | Ikeda et al. |
| 2010/0123152 A1 | 5/2010 | Sugisawa et al. |
| 2010/0207518 A1 | 8/2010 | Ikeda et al. |
| 2010/0301382 A1 | 12/2010 | Shitagaki et al. |
| 2011/0210316 A1 | 9/2011 | Kadoma et al. |
| 2011/0253991 A1 | 10/2011 | Oyamada et al. |
| 2012/0132895 A1 | 5/2012 | Kido et al. |
| 2012/0133276 A1 | 5/2012 | Thompson et al. |
| 2012/0194062 A1 | 8/2012 | Osaka et al. |
| 2012/0280218 A1 | 11/2012 | Watanabe et al. |
| 2014/0042413 A1 | 2/2014 | Xia et al. |
| 2015/0221875 A1 | 8/2015 | Osaka et al. |
| 2015/0249225 A1 | 9/2015 | Lin et al. |
| 2016/0372685 A1 | 12/2016 | Lin et al. |
| 2017/0117489 A1 | 4/2017 | Ma et al. |
| 2017/0179394 A1 | 6/2017 | Brooks et al. |

FOREIGN PATENT DOCUMENTS

| | | |
|---|---|---|
| EP | 1524706 A | 4/2005 |
| EP | 1617493 A | 1/2006 |
| EP | 1351558 B | 7/2006 |
| EP | 1821579 A | 8/2007 |
| EP | 1881543 A | 1/2008 |
| EP | 2378584 A | 10/2011 |
| EP | 2511254 A | 10/2012 |
| EP | 3112336 A | 1/2017 |
| EP | 3159333 A | 4/2017 |
| JP | 02-288092 A | 11/1990 |
| JP | 03-274695 A | 12/1991 |
| JP | 09-063771 A | 3/1997 |
| JP | 11-307259 A | 11/1999 |
| JP | 11-307264 A | 11/1999 |
| JP | 2001-192651 A | 7/2001 |
| JP | 2002-329580 A | 11/2002 |
| JP | 2002-338957 A | 11/2002 |
| JP | 2002-343576 A | 11/2002 |
| JP | 2003-272860 A | 9/2003 |
| JP | 2004-253298 A | 9/2004 |
| JP | 2005-026121 A | 1/2005 |
| JP | 2005-071983 A | 3/2005 |
| JP | 2005-123164 A | 5/2005 |
| JP | 2005-222751 A | 8/2005 |
| JP | 2005-251587 A | 9/2005 |
| JP | 2006-319070 A | 11/2006 |
| JP | 2007-073932 A | 3/2007 |
| JP | 2007-251148 A | 9/2007 |
| JP | 2008-021665 A | 1/2008 |
| JP | 2009-046615 A | 3/2009 |
| JP | 2009-272144 A | 11/2009 |
| JP | 2010-114312 A | 5/2010 |
| JP | 2010-153365 A | 7/2010 |
| JP | 2010-171363 A | 8/2010 |
| JP | 2010-535806 | 11/2010 |
| JP | 4637271 | 2/2011 |
| JP | 2011-166102 A | 8/2011 |
| JP | 2011-166103 A | 8/2011 |
| JP | 2011-166105 A | 8/2011 |
| JP | 2012-019174 A | 1/2012 |
| JP | 2012-169613 A | 9/2012 |
| WO | WO-2006/121811 | 11/2006 |
| WO | WO-2007/013478 | 2/2007 |
| WO | WO-2008/054584 | 5/2008 |
| WO | WO-2009/021107 | 2/2009 |
| WO | WO-2009/021126 | 2/2009 |
| WO | WO-2009/030981 | 3/2009 |
| WO | WO-2009/085344 | 7/2009 |
| WO | WO-2009/086028 | 7/2009 |
| WO | WO-2010/073864 | 7/2010 |

OTHER PUBLICATIONS

Tao.S et al., "Anthracene Derivative for a Non-Doped Blue-Emitting Organic Electroluminescence Device With Both Excellent Color Purity and High Efficiency", Chem. Phys. Lett. (Chemical Physics Letters), 2004, vol. 397, pp. 1-4.

(56) References Cited

OTHER PUBLICATIONS

European Search Report (Application No. 12159023.6) dated Jul. 18, 2012.
Yang.Y et al., "Polyaniline as a Transparent Electrode for Polymer Light-Emitting Diodes:Lower Operating Voltage and Higher Efficiency", Appl. Phys. Lett. (Applied Physics Letters) , Mar. 7, 1994, vol. 64, No. 10, pp. 1245-1247.
Korean Office Action (Application No. 2012-0029221) dated Aug. 17, 2018.

* cited by examiner

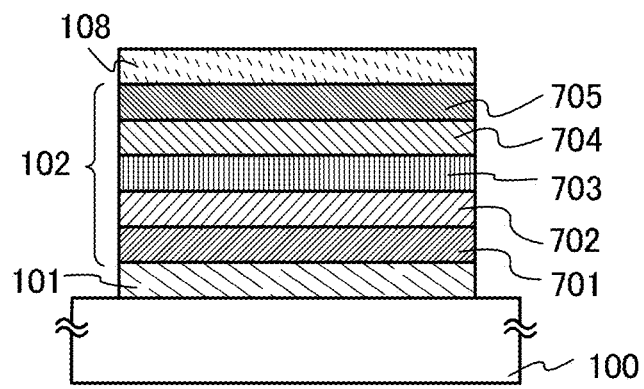
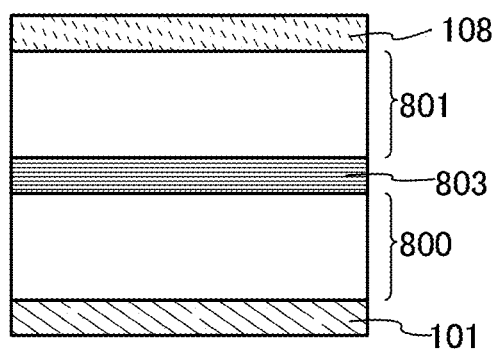
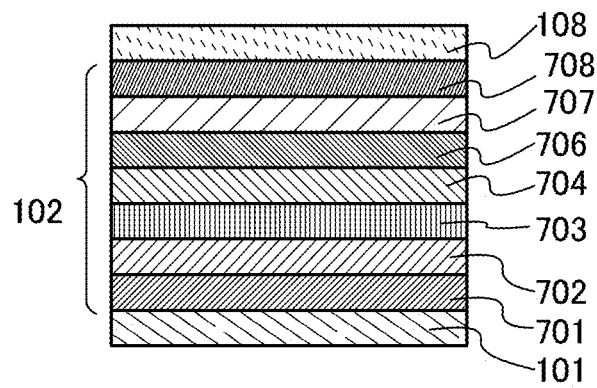

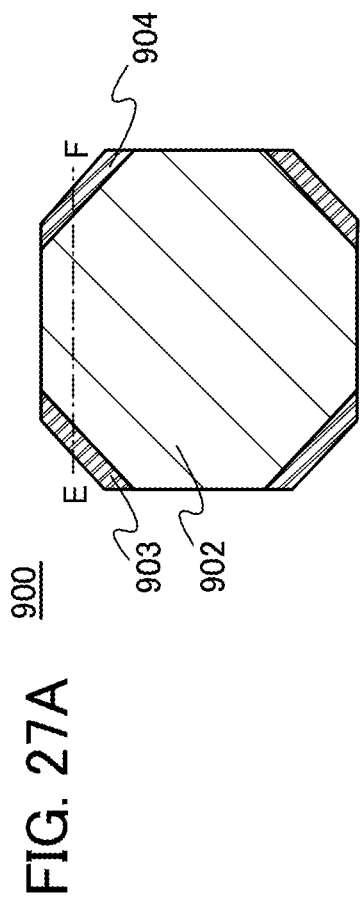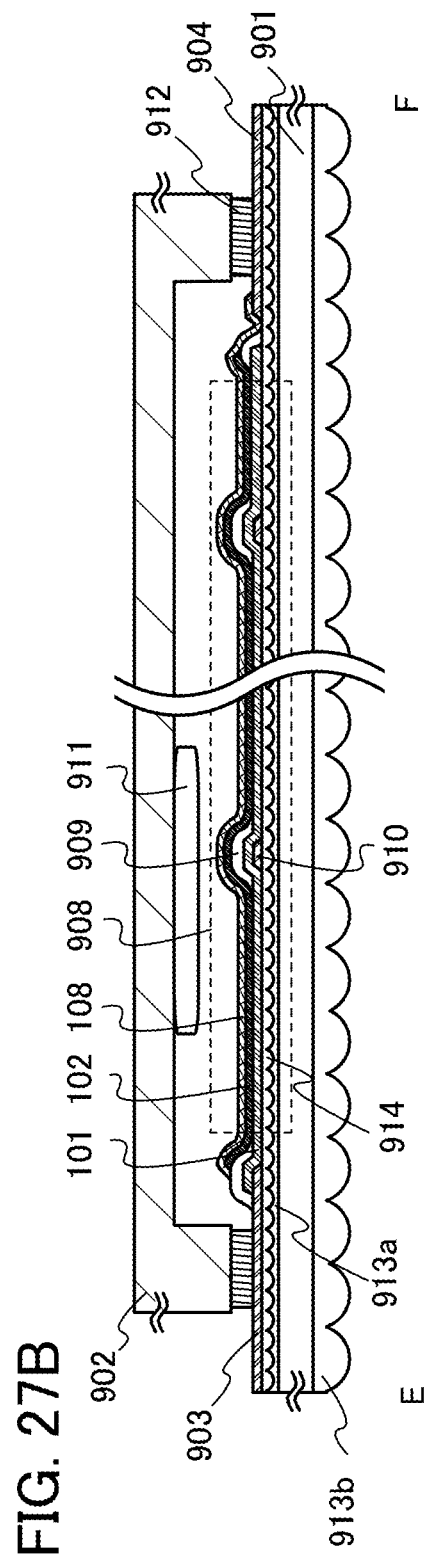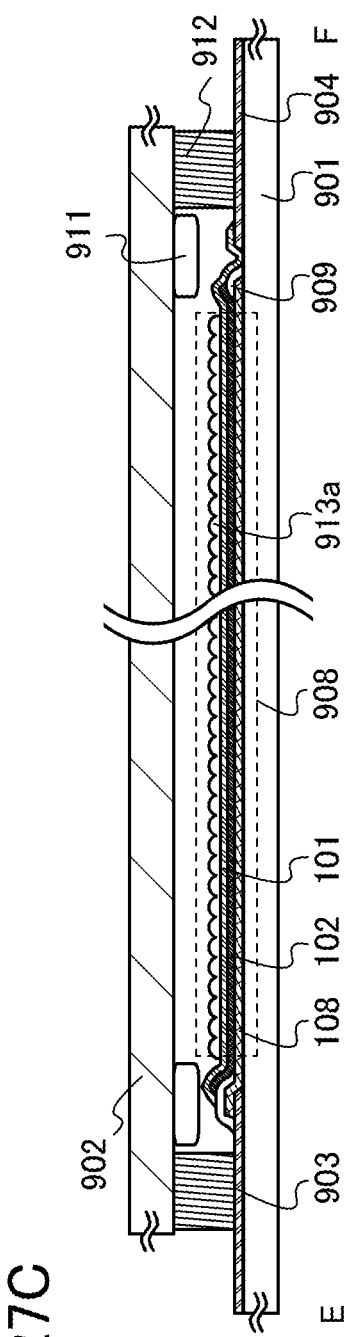
FIG. 27A
FIG. 27B
FIG. 27C

COMPOSITE MATERIAL, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a composite material including an organic compound and an inorganic compound, a light-emitting element, a light-emitting device, an electronic device, and a lighting device.

2. Description of the Related Art

In recent years, research and development have been extensively conducted on light-emitting elements using organic electroluminescence (EL). In a basic structure of such a light-emitting element, a layer containing a light-emitting organic compound is interposed between a pair of electrodes. By application of a voltage to this element, light emission from the light-emitting organic compound can be obtained.

Since such light-emitting elements are of self-light-emitting type, it is considered that the light-emitting elements have advantages over liquid crystal displays in that visibility of pixels is high, backlights are not required, and so on and are therefore suitable as flat panel display elements. In addition, it is also a great advantage that the light-emitting elements can be manufactured as thin and lightweight elements. Furthermore, very high speed response is also one of the features of such elements.

Furthermore, since such light-emitting elements can be formed in a film form, they make it possible to easily form large-area elements. This feature is difficult to obtain with point light sources typified by incandescent lamps and LEDs or linear light sources typified by fluorescent lamps. Thus, light-emitting elements also have great potential as planar light sources applicable to lighting devices and the like.

As described above, application of light-emitting elements using organic EL to light-emitting devices, lighting devices, or the like is expected. At the same time, there are many issues regarding light-emitting elements using organic EL. One of the issues is a reduction in power consumption. In order to reduce power consumption, it is important to reduce driving voltage for the light-emitting element. Further, in order to reduce the driving voltage, it is necessary to feed a large amount of current at a low voltage because the emission intensity of the light-emitting element using organic EL is determined by the amount of electric current flowing therein.

Previously, as a method for reducing driving voltage, an approach of providing a buffer layer between an electrode and the layer containing a light-emitting organic compound, has been attempted. For example, it is known that driving voltage can be reduced by providing a buffer layer which includes polyaniline (PANI) doped with camphorsulfonic acid, between indium tin oxide (ITO) and a light-emitting layer (see Non-Patent Document 1, for example). It is explained that this is because PANI has a property of excellent carrier injection into the light-emitting layer. Note that in Non-Patent Document 1, PANI, which is used for the buffer layer, is also regarded as part of the electrode.

However, as described in Non-Patent Document 1, PANI has a problem that transmittance becomes poor when a film thickness becomes thick. Specifically, it is reported that at a film thickness of about 250 nm, the transmittance is less than 70%. In other words, since the problem lies in the transparency of the material itself used for the buffer layer, light generated within the element cannot be extracted efficiently.

Also, according to Patent Document 1, an approach of serially connecting light-emitting elements (called light-emitting units in Patent Document 1) to improve luminance per a certain current density, namely, current efficiency, has been attempted. In Patent Document 1, for a connecting portion of serially connected light-emitting elements, a mixed layer of an organic compound and a metal oxide (specifically, vanadium oxide or rhenium oxide) is used, and this layer is considered capable of injecting holes and electrons into light-emitting units.

However, as apparent by looking at an embodiment, for the mixed layer of an organic compound and a metal oxide which is disclosed in Patent Document 1, not only a high absorption peak in the infrared region but also a high absorption peak in the visible light region (around 500 nm) are observed, and a problem in transparency occurs. This is due to the effect of an absorption band generated by charge-transfer interaction. Therefore, as expected, light generated within the element cannot be extracted efficiently, and the light emission efficiency of the element is degraded.

REFERENCES

[Patent Document 1] Japanese Published Patent Application No. 2003-272860

[Non-Patent Document 1] Y Yang et al., *Applied Physics Letters*, Vol. 64 (10), 1245-1247 (1994)

SUMMARY OF THE INVENTION

In view of the above description, an object of one embodiment of the present invention is to provide a composite material which includes an organic compound and an inorganic compound and which has a high carrier-transport property. Another object of one embodiment of the present invention is to provide a composite material having a good property of carrier injection into an organic compound. Another object of one embodiment of the present invention is to provide a composite material in which light absorption due to charge-transfer interaction is unlikely to occur. Another object of one embodiment of the present invention is to provide a composite material having a high visible-light-transmitting property.

An object of one embodiment of the present invention is to provide a light-emitting element having high emission efficiency by applying the above-described composite material to the light-emitting element. Another object of one embodiment of the present invention is to provide a light-emitting element having a low driving voltage. Another object of one embodiment of the present invention is to provide a light-emitting element having a long lifetime. Another object of one embodiment of the present invention is to provide a light-emitting device including the light-emitting element, an electronic device including the light-emitting device, or a lighting device including the light-emitting device.

Note that an object of the invention to be disclosed below is to achieve at least one of the above-described objects.

One embodiment of the present invention is a composite material including a hydrocarbon compound which has a substituent bonded to a naphthalene skeleton, a phenanthrene skeleton, or a triphenylene skeleton and which has a molecular weight greater than or equal to 350 and less than or equal to 2000, and an inorganic compound exhibiting an electron-accepting property with respect to the hydrocarbon compound. In the hydrocarbon compound, the substituent has one or more rings selected from a benzene ring, a naphthalene ring, a phenanthrene ring, and a triphenylene ring. Note that unless otherwise specified, the ring of the hydrocarbon compound in the composite material of one embodiment of the present invention may be a substituted or unsubstituted ring. For example, the substituent may have one or more rings selected from a substituted or unsubstituted benzene ring, a substituted or unsubstituted naphthalene ring, a substituted or unsubstituted phenanthrene ring, and a substituted or unsubstituted triphenylene ring.

The above-described composite material has a high carrier-transport property. The above-described composite material also has a good property of carrier injection into an organic compound. Further, in the composite material, light absorption due to charge-transfer interaction is unlikely to occur. Furthermore, the composite material has a high visible-light-transmitting property (hereinafter simply referred to as light-transmitting property).

The hydrocarbon compound included in the composite material of one embodiment of the present invention, which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000, exhibits an absorption peak at a shorter wavelength than visible-light wavelengths (380 nm to 760 nm).

In the above composite material, the occurrence of light absorption due to charge-transfer interaction can be suppressed and an absorption peak of the hydrocarbon compound itself can also be controlled so as to appear at a shorter wavelength than visible-light wavelengths (380 nm to 760 nm). Accordingly, the composite material can have a high light-transmitting property.

A naphthalene skeleton, a phenanthrene skeleton, and a triphenylene skeleton each have a rigid structure; therefore, the molecular weight of the hydrocarbon compound is preferably 350 or more because the film quality of the composite material is stable with such a molecular weight. More preferably, the molecular weight is 450 or more. Although there is no limitation on the maximum molecular weight, the molecular weight is preferably 2000 or less in consideration of evaporativity when the composite material is subjected to heating evaporation.

One embodiment of the present invention is a composite material including a hydrocarbon compound which has a molecular weight greater than or equal to 350 and less than or equal to 2000 and which exhibits an absorption peak at a shorter wavelength than visible-light wavelengths, and an inorganic compound exhibiting an electron-accepting property with respect to the hydrocarbon compound. In the hydrocarbon compound, a substituent is bonded to a naphthalene skeleton, a phenanthrene skeleton, or a triphenylene skeleton, and the substituent has one or more rings selected from a benzene ring, a naphthalene ring, a phenanthrene ring, and a triphenylene ring.

Another embodiment of the present invention is a composite material including a hydrocarbon compound which has a substituent bonded to the α- or β-position of a naphthalene skeleton, the 9-position of a phenanthrene skeleton, or the 2-position of a triphenylene skeleton and which has a molecular weight greater than or equal to 350 and less than or equal to 2000, and an inorganic compound exhibiting an electron-accepting property with respect to the hydrocarbon compound. In the hydrocarbon compound, the substituent has one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and an inorganic compound exhibiting an electron-accepting property with respect to the hydrocarbon compound. In the hydrocarbon compound, a substituent is bonded to the α- or β-position of a naphthalene skeleton, the 9-position of a phenanthrene skeleton, or the 2-position of a triphenylene skeleton, and the substituent has one or more rings selected from a benzene ring, a naphthalene ring, a phenanthrene ring, and a triphenylene ring.

In the composite material, the occurrence of light absorption due to charge-transfer interaction can be suppressed by use of the hydrocarbon compound having a substituent at the α- or β-position of a naphthalene skeleton, the 9-position of a phenanthrene skeleton, or the 2-position of a triphenylene skeleton.

Another embodiment of the present invention is a composite material including a hydrocarbon compound which has a phenyl group bonded to a naphthalene skeleton, a phenanthrene skeleton, or a triphenylene skeleton and which has a molecular weight greater than or equal to 350 and less than or equal to 2000, and an inorganic compound exhibiting an electron-accepting property with respect to the hydrocarbon compound. In the hydrocarbon compound, the phenyl group has one or more substituents, and the substituent or substituents have one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and an inorganic compound exhibiting an electron-accepting property with respect to the hydrocarbon compound. In the hydrocarbon compound, a phenyl group is bonded to a naphthalene skeleton, a phenanthrene skeleton, or a triphenylene skeleton; the phenyl group has one or more substituents; and the substituent or substituents have one or more rings selected from a benzene ring, a naphthalene ring, a phenanthrene ring, and a triphenylene ring.

The hydrocarbon compound in which a phenyl group with small conjugation is bonded to a naphthalene skeleton, a phenanthrene skeleton, or a triphenylene skeleton is preferred because, even when a substituent is further bonded to the phenyl group, the conjugation is difficult to extend and accordingly a light-transmitting property can be maintained. Further, in the composite material, use of the hydrocarbon compound is preferred because such use can suppress the occurrence of light absorption due to charge-transfer interaction and can also provide the stable film quality of the composite material. Furthermore, since the conjugation becomes difficult to extend, such use is effective also in terms of improving the light-transmitting property.

Another embodiment of the present invention is a composite material including a hydrocarbon compound which has a phenyl group bonded to the α- or β-position of a naphthalene skeleton, the 9-position of a phenanthrene skeleton, or the 2-position of a triphenylene skeleton and which has a molecular weight greater than or equal to 350 and less than or equal to 2000, and an inorganic compound exhibiting an electron-accepting property with respect to the hydrocarbon compound. In the hydrocarbon compound, the phenyl group has one or more substituents, and the substituent or substituents have one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and an inorganic compound exhibiting an electron-accepting property with respect to the hydrocarbon compound. In the hydrocarbon compound, a phenyl group is bonded to the α- or β-position of a naphthalene skeleton, the 9-position of a phenanthrene skeleton, or the 2-position of a triphenylene skeleton; the phenyl group has one or more substituents; and the substituent or substituents have one or more rings selected from a benzene ring, a naphthalene ring, a phenanthrene ring, and a triphenylene ring.

Another embodiment of the present invention is a composite material including a hydrocarbon compound represented by a general formula (G1) and an inorganic compound exhibiting an electron-accepting property with respect to the hydrocarbon compound.

[Chemical Formula 1]

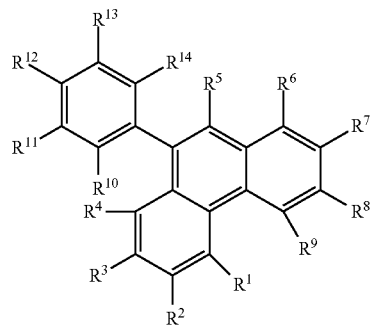

(G1)

In the formula, $R^1$ to $R^9$ independently represent hydrogen, an alkyl group having 1 to 4 carbon atoms, or an aryl group having 6 to 25 carbon atoms in a ring, and $R^{10}$ to $R^{14}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{10}$ to $R^{14}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by a general formula (G2) and an inorganic compound exhibiting an electron-accepting property with respect to the hydrocarbon compound.

[Chemical Formula 2]

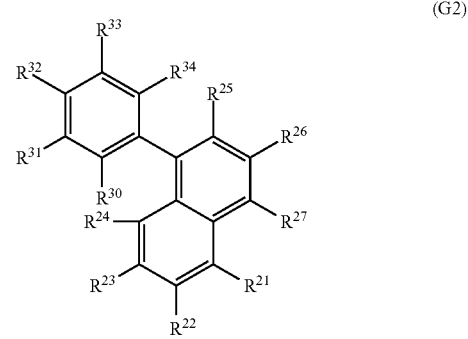

(G2)

In the formula, $R^{21}$ to $R^{27}$ independently represent hydrogen, an alkyl group having 1 to 4 carbon atoms, or an aryl group having 6 to 25 carbon atoms in a ring, and $R^{30}$ to $R^{34}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{30}$ to $R^{34}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by a general formula (G3) and an inorganic compound exhibiting an electron-accepting property with respect to the hydrocarbon compound.

[Chemical Formula 3]

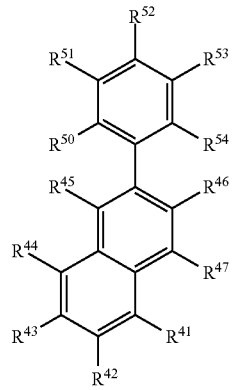

(G3)

In the formula, $R^{41}$ to $R^{47}$ independently represent hydrogen, an alkyl group having 1 to 4 carbon atoms, or an aryl group having 6 to 25 carbon atoms in a ring, and $R^{50}$ to $R^{54}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{50}$ to $R^{54}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by a general formula (G4) and an inorganic compound exhibiting an electron-accepting property with respect to the hydrocarbon compound.

[Chemical Formula 4]

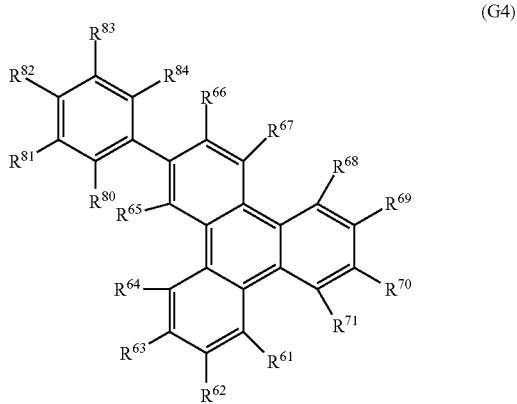

(G4)

In the formula, $R^{61}$ to $R^{71}$ independently represent hydrogen, an alkyl group having 1 to 4 carbon atoms, or an aryl group having 6 to 25 carbon atoms in a ring, and $R^{80}$ to $R^{84}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{80}$ to $R^{84}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by a general formula (G5) and an inorganic compound exhibiting an electron-accepting property with respect to the hydrocarbon compound.

[Chemical Formula 5]

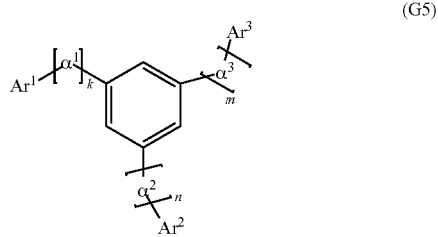

(G5)

In the formula, $\alpha^1$ to $\alpha^3$ independently represent a phenylene group or a biphenylene group, and $Ar^1$ to $Ar^3$ independently represent a substituted or unsubstituted naphthyl group, a substituted or unsubstituted phenanthryl group, or a substituted or unsubstituted triphenylenyl group. In addition, k, n, and m independently represent 0 or 1. Note that the naphthyl group is preferably an α-naphthyl group or a β-naphthyl group. The phenanthryl group is preferably a 9-phenanthryl group. The triphenylenyl group is preferably a triphenylen-2-yl group.

Another embodiment of the present invention is a composite material including a hydrocarbon compound which has a substituent bonded to a naphthalene skeleton, a phenanthrene skeleton, or a triphenylene skeleton and which has a molecular weight greater than or equal to 350 and less than or equal to 2000, and a transition metal oxide. In the hydrocarbon compound, the substituent has one or more rings selected from a benzene ring, a naphthalene ring, a phenanthrene ring, and a triphenylene ring.

The above-described composite material has a high carrier-transport property. The above-described composite material also has a good property of carrier injection into an organic compound. Further, in the composite material, light absorption due to charge-transfer interaction is unlikely to occur. Furthermore, the composite material has a high light-transmitting property.

The hydrocarbon compound included in the composite material of one embodiment of the present invention, which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000, exhibits an absorption peak at a shorter wavelength than visible-light wavelengths (380 nm to 760 nm).

In the above composite material, the occurrence of light absorption due to charge-transfer interaction can be suppressed and an absorption peak of the hydrocarbon compound itself can also be controlled so as to appear at a shorter wavelength than visible-light wavelengths. Accordingly, the composite material can have a high light-transmitting property.

A naphthalene skeleton, a phenanthrene skeleton, and a triphenylene skeleton each have a rigid structure; therefore, the molecular weight of the hydrocarbon compound is preferably 350 or more because the film quality of the composite material is stable with such a molecular weight. More preferably, the molecular weight is 450 or more. Although there is no limitation on the maximum molecular weight, the molecular weight is preferably 2000 or less in consideration of evaporativity when the composite material is subjected to heating evaporation.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and a transition metal oxide. In the hydrocarbon compound, a substituent is bonded to a naphthalene skeleton, a phenanthrene skeleton, or a triphenylene skeleton, and the substituent has one or more rings selected from a benzene ring, a naphthalene ring, a phenanthrene ring, and a triphenylene ring.

Another embodiment of the present invention is a composite material including a hydrocarbon compound which has a substituent bonded to the α- or β-position of a naphthalene skeleton, the 9-position of a phenanthrene skeleton, or the 2-position of a triphenylene skeleton and which has a molecular weight greater than or equal to 350 and less than or equal to 2000, and a transition metal oxide. In the hydrocarbon compound, the substituent has one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and a transition metal oxide. In the hydrocarbon compound, a substituent is bonded to the α- or β-position of a naphthalene skeleton, the 9-position of a phenanthrene skeleton, or the 2-position of a triphenylene skeleton, and the substituent has one or more rings selected from a benzene ring, a naphthalene ring, a phenanthrene ring, and a triphenylene ring.

In the composite material, the occurrence of light absorption due to charge-transfer interaction can be suppressed by use of the hydrocarbon compound having a substituent at the α- or β-position of a naphthalene skeleton, the 9-position of a phenanthrene skeleton, or the 2-position of a triphenylene skeleton.

Another embodiment of the present invention is a composite material including a hydrocarbon compound which has a phenyl group bonded to a naphthalene skeleton, a phenanthrene skeleton, or a triphenylene skeleton and which has a molecular weight greater than or equal to 350 and less than or equal to 2000, and a transition metal oxide. In the hydrocarbon compound, the phenyl group has one or more substituents, and the substituent or substituents have one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and a transition metal oxide. In the hydrocarbon compound, a phenyl group is bonded to a naphthalene skeleton, a phenanthrene skeleton, or a triphenylene skeleton; the phenyl group has one or more substituents; and the substituent or substituents have one or more rings selected from a benzene ring, a naphthalene ring, a phenanthrene ring, and a triphenylene ring.

The hydrocarbon compound in which a phenyl group with small conjugation is bonded to a naphthalene skeleton, a phenanthrene skeleton, or a triphenylene skeleton is preferred because, even when a substituent is further bonded to the phenyl group, the conjugation is difficult to extend and accordingly a light-transmitting property can be maintained. Further, in the composite material, use of the hydrocarbon compound is preferred because such use can suppress the occurrence of light absorption due to charge-transfer interaction and can also provide the stable film quality of the composite material. Furthermore, since the conjugation becomes difficult to extend, such use is effective also in terms of improving the light-transmitting property.

Another embodiment of the present invention is a composite material including a hydrocarbon compound which has a phenyl group bonded to the α- or β-position of a naphthalene skeleton, the 9-position of a phenanthrene skeleton, or the 2-position of a triphenylene skeleton and which has a molecular weight greater than or equal to 350 and less than or equal to 2000, and a transition metal oxide. In the hydrocarbon compound, the phenyl group has one or more substituents, and the substituent or substituents have one or more rings selected from a benzene ring, a naphthalene ring, a phenanthrene ring, and a triphenylene ring.

Another embodiment of the present invention is a composite material including a hydrocarbon compound which has a molecular weight greater than or equal to 350 and less than or equal to 2000 and which exhibits an absorption peak at a shorter wavelength than visible-light wavelengths, and a transition metal oxide. In the hydrocarbon compound, a phenyl group is bonded to the α- or β-position of a naphthalene skeleton, the 9-position of a phenanthrene skeleton, or the 2-position of a triphenylene skeleton; the phenyl group has one or more substituents; and the substituent or substituents have one or more rings selected from a benzene ring, a naphthalene ring, a phenanthrene ring, and a triphenylene ring.

Another embodiment of the present invention is a composite material including a hydrocarbon compound represented by the general formula (G1) and a transition metal oxide.

[Chemical Formula 6]

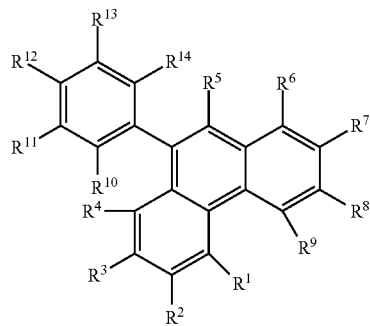

(G1)

In the formula, $R^1$ to $R^9$ independently represent hydrogen, an alkyl group having 1 to 4 carbon atoms, or an aryl group having 6 to 25 carbon atoms in a ring, and $R^{10}$ to $R^{14}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{10}$ to $R^{14}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by the general formula (G2) and a transition metal oxide.

[Chemical Formula 7]

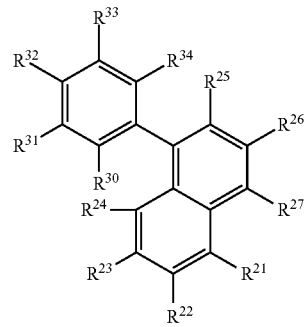

(G2)

In the formula, $R^{21}$ to $R^{27}$ independently represent hydrogen, an alkyl group having 1 to 4 carbon atoms, or an aryl group having 6 to 25 carbon atoms in a ring, and $R^{30}$ to $R^{34}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{30}$ to $R^{34}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by the general formula (G3) and a transition metal oxide.

[Chemical formula 8]

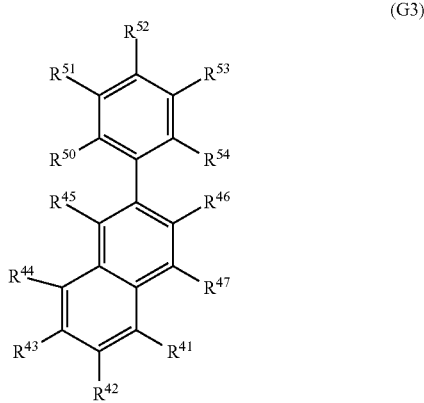

(G3)

In the formula, $R^{41}$ to $R^{47}$ independently represent hydrogen, an alkyl group having 1 to 4 carbon atoms, or an aryl group having 6 to 25 carbon atoms in a ring, and $R^{50}$ to $R^{54}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{50}$ to $R^{54}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by the general formula (G4) and a transition metal oxide.

[Chemical Formula 9]

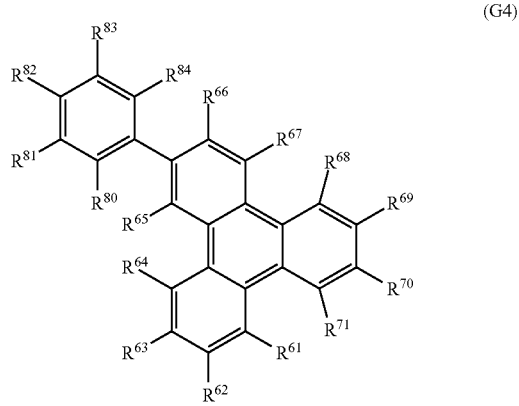

(G4)

In the formula, $R^{61}$ to $R^{71}$ independently represent hydrogen, an alkyl group having 1 to 4 carbon atoms, or an aryl group having 6 to 25 carbon atoms in a ring, and $R^{80}$ to $R^{84}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{80}$ to $R^{84}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by the general formula (G5) and a transition metal oxide.

[Chemical Formula 10]

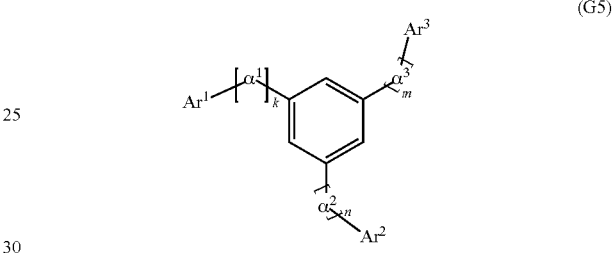

(G5)

In the formula, $\alpha^1$ to $\alpha^3$ independently represent a phenylene group or a biphenylene group, and $Ar^1$ to $Ar^3$ independently represent a substituted or unsubstituted naphthyl group, a substituted or unsubstituted phenanthryl group, or a substituted or unsubstituted triphenylenyl group. In addition, k, n, and m independently represent 0 or 1. Note that the naphthyl group is preferably an α-naphthyl group or a β-naphthyl group. The phenanthryl group is preferably a 9-phenanthryl group. The triphenylenyl group is preferably a triphenylen-2-yl group.

The transition metal oxide included in the above-described composite material is preferably one or more types of oxides selected from titanium oxide, vanadium oxide, tantalum oxide, molybdenum oxide, tungsten oxide, rhenium oxide, ruthenium oxide, chromium oxide, zirconium oxide, hafnium oxide, and silver oxide.

Although there is no particular limitation on the highest occupied molecular orbital level (HOMO level) of the hydrocarbon compound used in the above composite material, the hydrocarbon compound used in one embodiment of the present invention has a relatively deep HOMO level (specifically, lower than or equal to −5.7 eV). Accordingly, the occurrence of light absorption due to charge-transfer interaction can be suppressed. Therefore, the HOMO level of the hydrocarbon compound used in the above composite material is preferably lower than or equal to −5.7 eV when measured by photoelectron spectroscopy.

Another embodiment of the present invention is a light-emitting element including a layer containing a light-emitting substance (hereinafter also referred to as EL layer) between a pair of electrodes. The layer containing a light-emitting substance includes a layer containing the above-described composite material.

In the above-described light-emitting element, it is preferable that the layer containing the composite material be in contact with one of the pair of electrodes which functions as an anode. It is also preferable that the layer containing the composite material be in contact with one of the pair of electrodes which functions as a cathode.

The above-described light-emitting element may include two layers containing the composite material, and it is preferable that one of the two layers containing the composite material be in contact with one of the pair of electrodes which functions as an anode and the other of the two layers be in contact with the other of the pair of electrodes which functions as a cathode.

As described above, the hydrocarbon compound used in one embodiment of the present invention has a relatively deep HOMO level (specifically, lower than or equal to −5.7 eV). Accordingly, even when an organic compound used in a layer, which is in contact with a surface of the layer containing the above composite material and closer than the surface to the cathode, (an organic compound used in a hole-transport layer, a light-emitting layer, or the like) has a relatively deep HOMO level (e.g., −6.0 eV), hole injection from the above composite material into the organic compound can be efficient. Needless to say, even when the organic compound has a shallow HOMO level (e.g., −5.0 eV), hole injection from the above composite material into the organic compound can be efficient. Therefore, the HOMO level of the organic compound contained in the layer (hereinafter, referred to as first layer), which is in contact with a surface of the layer containing the above composite material and closer than the surface to the cathode, is preferably higher than or equal to −6.0 eV and lower than or equal to −5.0 eV.

A HOMO level difference between the above composite material and the organic compound is preferably small and preferably within 0.2 eV. On the basis of the view that the HOMO level difference between the organic compound used in the first layer and the hydrocarbon compound used in the above composite material is made small as described above, a hydrocarbon compound which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000, like the hydrocarbon compound used in the above composite material, is preferably used as the organic compound used in the first layer. For example, the same hydrocarbon compound as that used in the above composite material can be used.

From the same view, a light-emitting layer in contact with the first layer also preferably contains (especially, as a host material) a hydrocarbon compound which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000, like the hydrocarbon compound used in the above composite material. For example, the same hydrocarbon compound as that used in the above composite material can be used.

In other words, one embodiment of the present invention is a light-emitting element including a layer containing a light-emitting substance between a pair of electrodes. The layer containing a light-emitting substance includes, on its anode side, a layer containing the above composite material, the first layer, and the light-emitting layer. The layer containing the above composite material, the first layer, and the light-emitting layer each contain a hydrocarbon compound which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000.

The hydrocarbon compounds contained in each of the layer containing the composite material, the first layer, and the light-emitting layer are preferably the same because, in such a case, hole injection through these layers are efficient and synthesis costs can be cut down.

Another embodiment of the present invention is a light-emitting element which includes a plurality of EL layers between a pair of electrodes, and which includes a layer containing the above-described composite material between the plurality of EL layers. In other words, the above-described composite material can be used for an intermediate layer (also referred to as charge-generation layer) in an organic EL light-emitting element including a stack of a plurality of light-emitting units (a tandem organic EL light-emitting element). In this structure, it is preferable to provide a layer containing a hydrocarbon compound which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000, so as to be in contact with a surface of the layer containing the composite material and closer than the surface to the cathode.

Another embodiment of the present invention is a light-emitting device including the above-described light-emitting element. Another embodiment of the present invention is an electronic device including the light-emitting device in a display portion. Another embodiment of the present invention is a lighting device including the light-emitting element in a light-emitting portion.

Of one embodiment of the present invention, it is possible to provide a composite material which includes an organic compound and an inorganic compound and which has a high carrier-transport property. It is also possible to provide a composite material having a good property of carrier injection into an organic compound. It is also possible to provide a composite material in which light absorption due to charge-transfer interaction is unlikely to occur. It is also possible to provide a composite material having a high visible-light-transmitting property.

Of one embodiment of the present invention, it is possible to provide a light-emitting element having high emission efficiency by applying the above-described composite material to the light-emitting element. It is also possible to provide a light-emitting element having a low driving voltage. It is also possible to provide a light-emitting element having a long lifetime. It is possible to provide a light-emitting device including the light-emitting element, an electronic device including the light-emitting device, or a lighting device including the light-emitting device.

BRIEF DESCRIPTION OF THE DRAWINGS

In the accompanying drawings:

FIGS. 1A to 1C each illustrate a light-emitting element of one embodiment of the present invention;

FIGS. 27A to 27C illustrate light-emitting devices of embodiments of the present invention;

DETAILED DESCRIPTION OF THE INVENTION

Figure 2A:
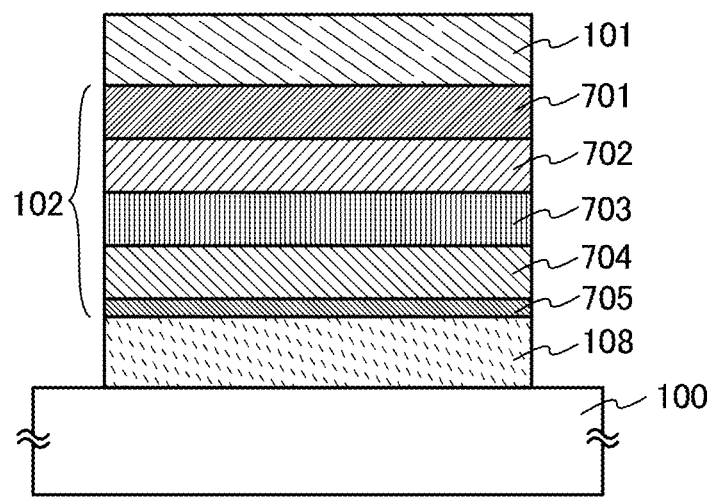
FIGS. 2A and 2B each illustrate a light-emitting element of one embodiment of the present invention.

Embodiments will be described in detail with reference to the drawings. Note that the present invention is not limited to the following description and it will be readily appreciated by those skilled in the art that the modes and details of the present invention can be modified in various ways without departing from the spirit and scope thereof. Therefore, the present invention should not be interpreted as being limited to the description in the following embodiments and examples. Note that the same portions or portions having similar functions are commonly denoted by the same reference numerals in different drawings, and repetitive description thereof is omitted.

First, a difference between the background art of the present invention and the present invention will be briefly described. As disclosed in Patent Document 1, it is interpreted that in a composite material including a mixture of an aromatic amine and an electron-accepting inorganic compound, the electron-accepting inorganic compound takes electrons from the aromatic amine, and accordingly, holes and electrons are generated in the aromatic amine and the inorganic compound, respectively. In other words, it is interpreted that in such a composite material, the aromatic amine and the electron-accepting inorganic compound form a charge-transfer complex. Some composite materials utilizing such a phenomenon and having excellent carrier-transport and/or carrier-injection properties have been reported so far.

However, it is generally known that an absorption band based on charge-transfer interaction is generated in such composite materials. This absorption band is said to be generated in the deep-red to near-infrared regions; actually, in many cases, an absorption band is also generated in the visible light region. For example, a composite material including a mixture of 4,4'-bis[N-(1-naphthyl)-N-phenylamino]biphenyl (abbreviation: NPB or α-NPB) and vanadium oxide or a mixture of NPB and molybdenum oxide has an absorption band at around 500 nm, in addition to an absorption band at around 1300 nm. This is a great disadvantage for optical devices such as light-emitting elements.

The present inventors have found that, despite the fact that no light absorption due to charge-transfer interaction can be observed (light absorption hardly occurs), excellent carrier-transport and/or carrier-injection properties can be exhibited by a composite material of an inorganic compound exhibiting an electron-accepting property and a hydrocarbon compound which has a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) and which has a molecular weight greater than or equal to 350 and less than or equal to 2000 or by a composite material of a transition metal oxide and the hydrocarbon compound. It has been considered that holes and electrons generated due to charge-transfer interaction are factors for exhibiting carrier-transport and/or carrier-injection properties. Therefore, it can be said that the present invention, which can provide excellent carrier-transport and/or carrier-injection properties despite the fact that no clear light absorption due to charge-transfer interaction is observed, contradicts the general theory and provides a remarkable and unexpected function.

As described above, the hydrocarbon compound used in one embodiment of the present invention has a naphthalene skeleton, a phenanthrene skeleton, or a triphenylene skeleton. In addition, the one or more substituents bonded to the skeleton have one or more rings selected from a benzene ring, a naphthalene ring, a phenanthrene ring, and a triphenylene ring. Benzene, naphthalene, phenanthrene, and triphenylene each have a large energy gap of its own. Therefore, when the ring selected from the above is used for the hydrocarbon compound, the hydrocarbon compound can be designed so as not to have an absorption peak in the visible light region (so as to have little absorption in the visible light region). Accordingly, there is a great advantage in terms of improving the light-transmitting property.

Further, cyclic voltammetry (CV) shows that the HOMO levels of naphthalene, phenanthrene, and triphenylene are very low. Therefore, it can be considered that the hydrocarbon compound, which is used in one embodiment of the present invention, by itself is excellent in hole injection into another organic compound, but has difficulty receiving holes from an electrically conductive material typified by Al or ITO (having a work function of approximately 3 eV to 5 eV). However, formation of such a composite material as in one embodiment of the present invention enables the problem in hole injection from an electrode to be overcome while maintaining an excellent property of hole injection into another organic compound. When the composite material is used for a light-emitting element, such a property of the composite material contributes to a reduction in driving voltage. Further, the high light-transmitting property leads to an increase in emission efficiency. Furthermore, the deep HOMO level is considered to prevent carrier accumulation in a light-emitting element carrier accumulation in a light-emitting element, leading to a longer lifetime.

Embodiments of the present invention will be described below with specific examples.

Embodiment 1

In this embodiment, a composite material of one embodiment of the present invention is described.

The composite material of one embodiment of the present invention is a composite material of an organic compound having a particular skeleton and an inorganic compound. There is no limitation on a method of preparing the composite material of one embodiment of the present invention; for example, it can be formed by a co-evaporation method in which the organic compound and the inorganic compound are deposited at the same time. The mixing ratio of the organic compound to the inorganic compound in the composite material of one embodiment of the present invention is preferably approximately 8:1 to 1:2 (=organic compound: inorganic compound) and more desirably 4:1 to 1:1 (=organic compound:inorganic compound) in mass ratio. When the composite material is formed by a co-evaporation method, the mixing ratio can be controlled by separately adjusting the deposition rates for the organic compound and the inorganic compound.

First, an organic compound that can be used for the composite material of one embodiment of the present invention is a hydrocarbon compound which has a substituent bonded to a naphthalene skeleton, a phenanthrene skeleton, or a triphenylene skeleton and which has a molecular weight greater than or equal to 350 and less than or equal to 2000. Note that the substituent has one or more rings selected from a benzene ring, a naphthalene ring, a phenanthrene ring, and a triphenylene ring.

The composite material including the hydrocarbon compound has a high carrier-transport property. The composite material also has a good property of carrier injection into an organic compound. Further, in the composite material, light absorption due to charge-transfer interaction with an inorganic compound is unlikely to occur. Furthermore, the composite material has a high light-transmitting property.

In the composite material including the hydrocarbon compound, the occurrence of light absorption due to charge-transfer interaction can be suppressed and an absorption peak of the hydrocarbon compound itself can also be controlled so as to appear at a shorter wavelength than visible-light wavelengths. Accordingly, the composite material can have a high light-transmitting property.

Naphthalene, phenanthrene, and triphenylene are condensed rings, and are therefore important conjugated rings for exhibiting a carrier-transport property (especially a hole-transport property). Further, the ring of the above substituent (one or more rings selected from a benzene ring, a naphthalene ring, a phenanthrene ring, and a triphenylene ring) is an important conjugated ring for enhancing a carrier-transport property (especially a hole-transport property), and is at the same time a conjugated ring having a wide energy gap. Accordingly, when the ring of the above substituent is limited to these rings, the occurrence of light absorption due to charge-transfer interaction can be suppressed and an absorption peak of the hydrocarbon compound itself can also be controlled so as to appear; thus, with the use of the hydrocarbon compound, the composite material can have a high light-transmitting property.

Although there is no particular limitation on a method of preparing the composite material, co-evaporation of the hydrocarbon compound and an inorganic compound is preferred, in which case the hydrocarbon compound is expected to vaporize readily. Therefore, in terms of molecular weight, the molecular weight of the hydrocarbon compound is preferably less than or equal to 2000. When an alkyl chain or the like is bonded to the hydrocarbon compound and the composite material is prepared through a wet process (a method in which a solution is used to form a film) or the like, the molecular weight may be greater than or equal to 2000.

The results of experiments and studies conducted by the present inventors have shown that a composite material formed by combining an aromatic hydrocarbon compound (e.g., an anthracene compound) and an inorganic compound can be easily crystallized when the mixing ratio of the inorganic compound to the aromatic compound is low (see the results in Comparison Example in Example 1 described later). In contrast, when the mixing ratio of the inorganic compound is high, although such crystallization can be suppressed, slight absorption peaks, which result from charge-transfer interaction between a skeleton of the aromatic hydrocarbon compound (e.g., an anthracene skeleton) and the inorganic compound increase in the visible light region. On the other hand, in the case where a hydrocarbon compound having a substituent bonded to a naphthalene skeleton, a phenanthrene skeleton, or a triphenylene skeleton (the substituent has one or more rings selected from a benzene ring, a naphthalene ring, a phenanthrene ring, and a triphenylene ring) is used as illustrated in one embodiment of the present invention, crystallization of the composite material is suppressed and the film quality thereof is stable. Therefore, in the case of the composite material of one embodiment of the present invention, it is not necessary to increase the proportion of the inorganic compound for the purpose of suppressing the crystallization, and it is possible to prevent an absorption peak resulting from charge-transfer interaction from being observed in the visible light region.

It is especially preferable to use a hydrocarbon compound having a substituent bonded to the α- or β-position of a naphthalene skeleton, the 9-position of a phenanthrene skeleton, or the 2-position of a triphenylene skeleton. Note that the substituent has one or more rings selected from a benzene ring, a naphthalene ring, a phenanthrene ring, and a triphenylene ring. In the composite material, use of such a hydrocarbon compound can suppress the occurrence of light absorption due to charge-transfer interaction.

With a bulky substituent (having 6 or more carbon atoms, for example) at the α- or β-position of a naphthalene skeleton, the 9-position of a phenanthrene skeleton, or the 2-position of a triphenylene skeleton, the molecule as a whole is a steric structure due to steric hindrance between the skeleton and the substituent. Consequently, the film quality of the composite material is stable.

It is preferable that a phenyl group be bonded to a naphthalene skeleton, a phenanthrene skeleton, or a triphenylene skeleton and the phenyl group have one or more substituents. Note that the substituent has one or more rings selected from a benzene ring, a naphthalene ring, a phenanthrene ring, and a triphenylene ring.

Since the phenyl group has small conjugation, even when the molecular weight is increased by bonding an additional substituent to the phenyl group, the hydrocarbon compound can maintain a wide energy gap, which is also effective in terms of improving a light-transmitting property. Further, in the composite material, use of the hydrocarbon compound is preferred because such use can suppress the occurrence of light absorption due to charge-transfer interaction.

Furthermore, with a bulky site (for example, a skeleton having a total of 12 or more carbon atoms including the above phenyl group) at the α- or β-position of a naphthalene skeleton, the 9-position of a phenanthrene skeleton, or the 2-position of a triphenylene skeleton, the molecule as a whole is a steric structure due to steric hindrance between the bulky site and the naphthalene skeleton, phenanthrene skeleton, or triphenylene skeleton. Consequently, the film quality of the composite material is stable.

To make the structure of the hydrocarbon compound bulkier, it is preferable that the hydrocarbon compound used for the above composite material be a compound to which three or more hydrocarbon skeletons are bonded, and particularly preferable that two of the hydrocarbon skeletons be any of a naphthalene skeleton, a phenanthrene skeleton, and a triphenylene skeleton.

When the composite material is prepared, co-evaporation of the hydrocarbon compound and an inorganic compound is preferred, in which case the hydrocarbon compound is expected to vaporize readily. Thus, the molecular weight of the hydrocarbon compound is preferably approximately less than or equal to 2000.

Naphthalene, phenanthrene, and triphenylene are condensed rings, and are therefore important conjugated rings for exhibiting a carrier-transport property (especially a hole-transport property). Further, the ring of the above substituent (one or more rings selected from a benzene ring, a naphthalene ring, a phenanthrene ring, and a triphenylene ring) is an important conjugated ring for enhancing a carrier-transport property (especially a hole-transport property), and is at the same time a conjugated ring having a wide energy gap. Accordingly, when the ring of the above substituent is limited to these rings, the occurrence of light absorption due to charge-transfer interaction can be suppressed and an absorption peak of the hydrocarbon compound itself can also be controlled so as to appear; thus, with the use of the hydrocarbon compound, the composite material can have a high light-transmitting property.

The phenyl group preferably has the substituent at the meta-position, in which case the band gap of the hydrocarbon compound can be kept wide, and a more steric structure can be formed to make crystallization more difficult. The phenyl group preferably has the substituent at the para-position, in which case the carrier-transport property of the hydrocarbon compound is excellent.

In one embodiment of the present invention, by including a phenanthrene skeleton, the hydrocarbon compound can be designed so as to have a high molecular weight while maintaining a high light-transmitting property. The hydrocarbon compound has good thermophysical properties and is therefore preferred. In addition, by use of the composite material including the hydrocarbon compound, a light-emitting element having a low driving voltage can be obtained.

One embodiment of the present invention is therefore a composite material including a hydrocarbon compound represented by the general formula (G1) and an inorganic compound exhibiting an electron-accepting property with respect to the hydrocarbon compound.

[Chemical Formula 11]

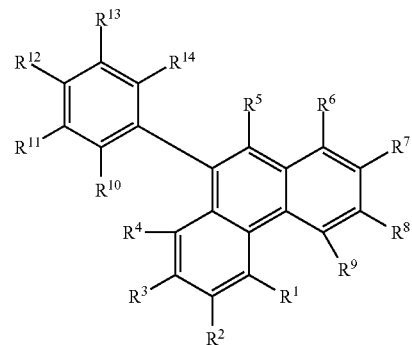

(G1)

In the formula, $R^1$ to $R^9$ independently represent hydrogen, an alkyl group having 1 to 4 carbon atoms, or an aryl group having 6 to 25 carbon atoms in a ring, $R^{10}$ to $R^{14}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{10}$ to $R^{14}$ represents a substituted or unsubstituted phenyl group, a substituted or unsubstituted naphthyl group, a substituted or unsubstituted phenanthryl group, or a substituted or unsubstituted triphenylenyl group.

In one embodiment of the present invention, the hydrocarbon compound can be designed so as to have a wide energy gap by including a naphthalene skeleton. The hydrocarbon compound does not exhibit an absorption peak in the visible light region and is therefore preferred. In addition, by use of the composite material including the hydrocarbon compound, a light-emitting element having high emission efficiency can be obtained.

One embodiment of the present invention is therefore a composite material including a hydrocarbon compound represented by the general formula (G2) and an inorganic compound exhibiting an electron-accepting property with respect to the hydrocarbon compound.

[Chemical Formula 12]

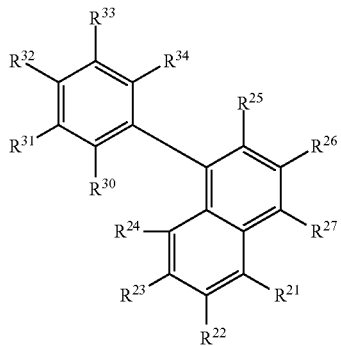

(G2)

In the formula, $R^{21}$ to $R^{27}$ independently represent hydrogen, an alkyl group having 1 to 4 carbon atoms, or an aryl group having 6 to 25 carbon atoms in a ring, and $R^{30}$ to $R^{34}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{30}$ to $R^{34}$ represents a substituted or unsubstituted phenyl group, a substituted or unsubstituted naphthyl group, a substituted or unsubstituted phenanthryl group, or a substituted or unsubstituted triphenylenyl group.

The β-position is preferable to the α-position as the position of a naphthalene skeleton at which the phenyl group is bonded because, in the case of the β-position, steric hindrance with another substituent can be reduced and accordingly synthesis can be facilitated. The α-position is preferable because, in the case of the α-position, the molecular structure becomes steric and intermolecular interaction is reduced and accordingly crystallization is made difficult, and also because rotation of the substituent (naphthyl group) in the molecule is suppressed and accordingly the thermophysical properties (glass transition temperature) can be improved.

One embodiment of the present invention is therefore a composite material including a hydrocarbon compound represented by the general formula (G3) and an inorganic compound exhibiting an electron-accepting property with respect to the hydrocarbon compound.

[Chemical Formula 13]

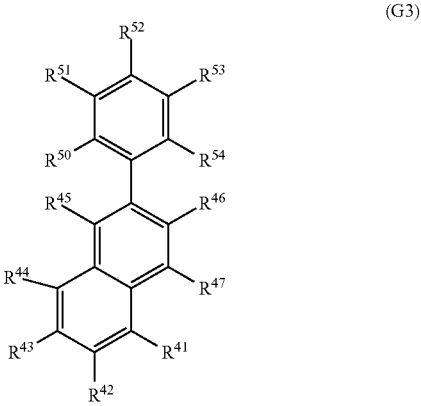

(G3)

In the formula, $R^{41}$ to $R^{47}$ independently represent hydrogen, an alkyl group having 1 to 4 carbon atoms, or an aryl group having 6 to 25 carbon atoms in a ring, and $R^{50}$ to $R^{54}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{50}$ to $R^{54}$ represents a substituted or unsubstituted phenyl group, a substituted or unsubstituted naphthyl group, a substituted or unsubstituted phenanthryl group, or a substituted or unsubstituted triphenylenyl group.

In one embodiment of the present invention, by including a triphenylene skeleton, the hydrocarbon compound can be designed so as to have a high molecular weight while maintaining a high light-transmitting property. The hydrocarbon compound has good thermophysical properties and is therefore preferred. The hydrocarbon compound is preferable because it makes the molecular structure steric and reduces intermolecular interaction and accordingly crystallization is made difficult.

Another embodiment of the present invention is a composite material including a hydrocarbon compound represented by the general formula (G4) and an inorganic compound exhibiting an electron-accepting property with respect to the hydrocarbon compound.

[Chemical Formula 14]

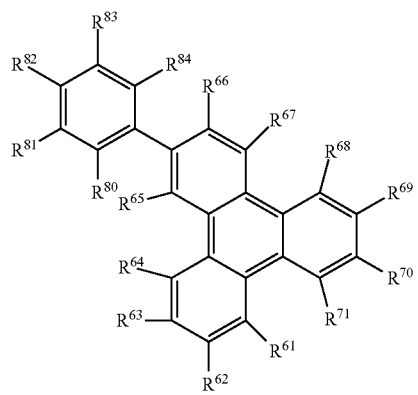

(G4)

In the formula, $R^{61}$ to $R^{71}$ independently represent hydrogen, an alkyl group having 1 to 4 carbon atoms, or an aryl group having 6 to 25 carbon atoms in a ring, and $R^{80}$ to $R^{84}$ independently represent hydrogen, an alkyl group having 1 to 6 carbon atoms, a substituted or unsubstituted phenyl group, a substituted or unsubstituted naphthyl group, a substituted or unsubstituted phenanthryl group, or a substituted or unsubstituted triphenylenyl group. Note that at least one of $R^{80}$ to $R^{84}$ represents a substituted or unsubstituted phenyl group, a substituted or unsubstituted naphthyl group, a substituted or unsubstituted phenanthryl group, or a substituted or unsubstituted triphenylenyl group.

Another embodiment of the present invention is a composite material including a hydrocarbon compound represented by the general formula (G5) and an inorganic compound exhibiting an electron-accepting property with respect to the hydrocarbon compound.

[Chemical Formula 15]

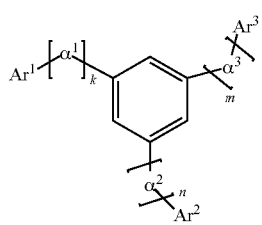

(G5)

In the formula, $\alpha^1$ to $\alpha^3$ independently represent a phenylene group or a biphenylene group, and $Ar^1$ to $Ar^3$ independently represent a substituted or unsubstituted naphthyl group, a substituted or unsubstituted phenanthryl group, or a substituted or unsubstituted triphenylenyl group. In addition, k, n, and m independently represent 0 or 1.

When the naphthyl group, phenanthryl group, or triphenylenyl group in $Ar^1$ to $Ar^3$ has a substituent or substituents, the substituent or substituents are separately an alkyl group having 1 to 6 carbon atoms or a substituted or unsubstituted phenyl group.

Examples of preferred structures of $\alpha^1$ to $\alpha^3$ include substituents represented by a general formula (α-1) to a general formula (α-5).

[Chemical Formula 16]

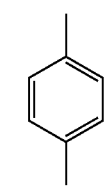

(α-1)

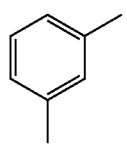

(α-2)

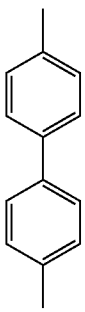

(α-3)

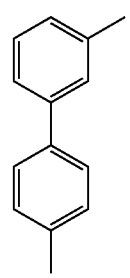

(α-4)

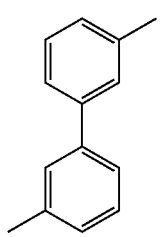

(α-5)

In the case where $\alpha^1$ to $\alpha^3$ are independently represented by the general formula (α-1) or the general formula (α-3) (i.e., the case where, in the general formula (G5), $Ar^1$ to $Ar^3$ are separately bonded to the central benzene ring at the para-position through a phenylene group or a biphenylene group), the hydrocarbon compound has an excellent carrier-transport property; thus, this case is preferable. In the case where $\alpha^1$ to $\alpha^3$ are independently represented by the general formula (α-2), the general formula (α-4), or the general formula (α-5) (i.e., the case where $Ar^1$ to $Ar^3$ are each bonded to the central benzene ring at the meta-position through a phenylene group or a biphenylene group), the molecular structure of the hydrocarbon compound is steric and crystallization is difficult; thus, this case is preferable. In the case where $\alpha^1$ to $\alpha^3$ are biphenylene groups as in the general formulae (α-3) to (α-5), the thermophysical properties of the hydrocarbon compound are improved; thus, this case is preferable.

For simplification of synthesis, all of $\alpha^1$ to $\alpha^3$ are preferably phenylene groups or biphenylene groups. At the same time, all of $Ar^1$ to $Ar^3$ are preferably substituted or unsubstituted naphthyl groups, substituted or unsubstituted phenanthryl groups, or substituted or unsubstituted triphenylenyl groups. In addition, k, n, and m are preferably the same number and especially preferably 0. More preferably, all of $Ar^1$ to $Ar^3$ are unsubstituted naphthyl groups, unsubstituted phenanthryl groups, or unsubstituted triphenylenyl groups and k, n, and m are each 0. In this case, the step in which the same three substituents are bonded to benzene at once is sufficient for synthesis, and consequently, a hydrocarbon compound having a high molecular weight can be obtained simply and inexpensively. In addition, rigid substituents are bonded to benzene in the propeller form to form a steric structure, so that a hydrocarbon compound having good thermophysical properties can be obtained.

Examples of the organic compound that can be used for the composite material of one embodiment of the present invention are represented by the following structural formulae (100) to (127) and (130) to (145).

[Chemical Formula 17]

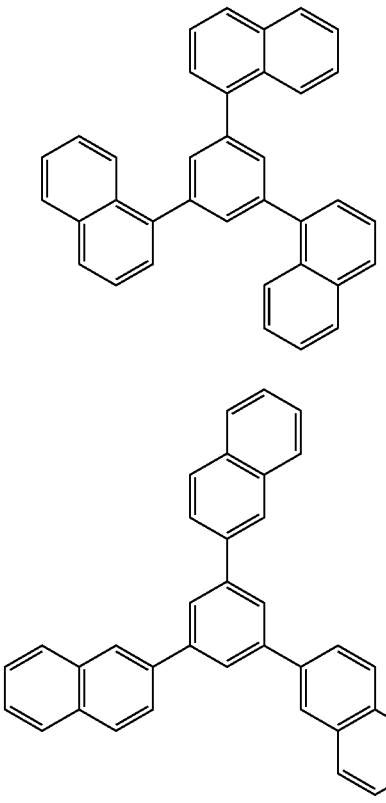

(100)

(101)

(102)

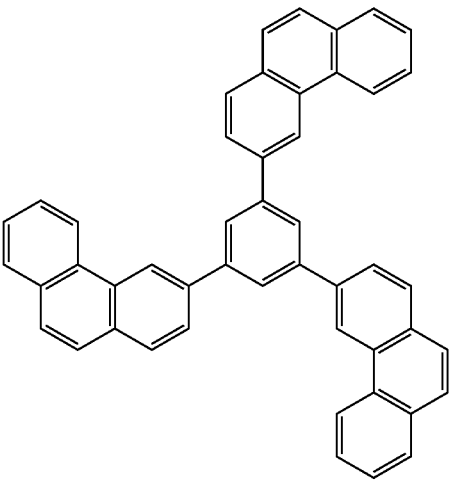

(103)

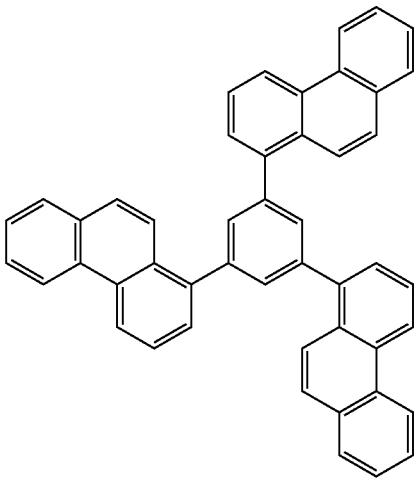

(104)

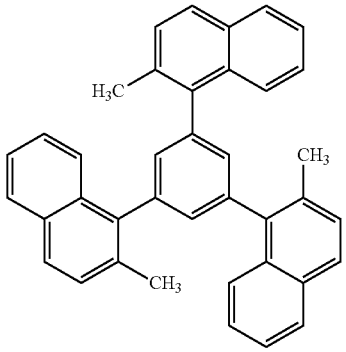

(105)

(106)
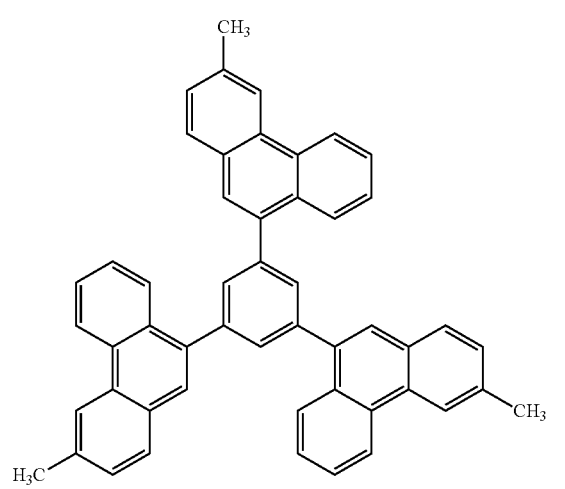
(107)
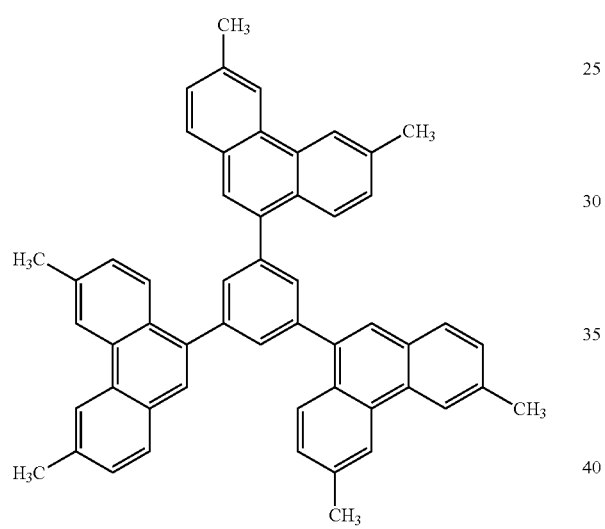
[Chemical Formula 18]
(108)
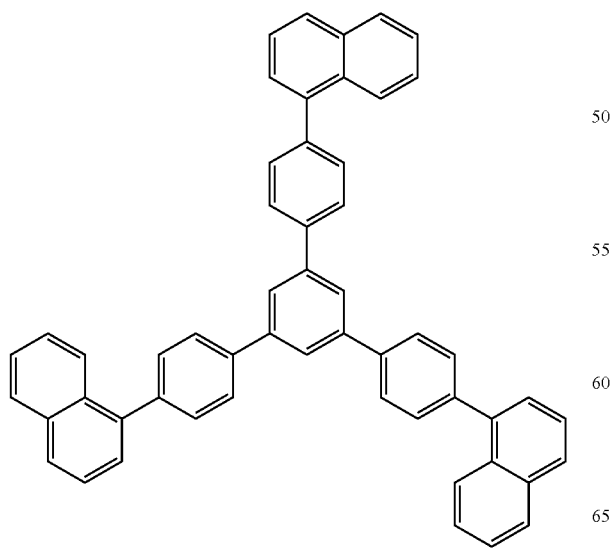
(109)
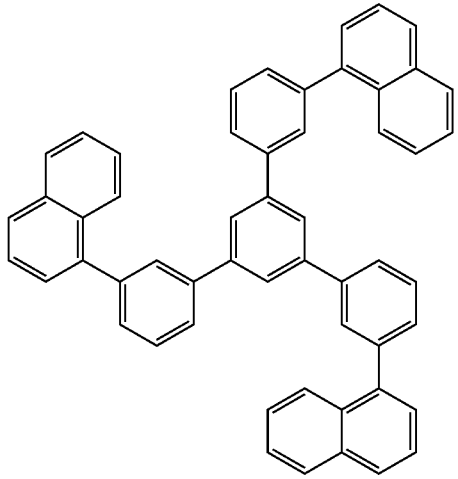
(110)
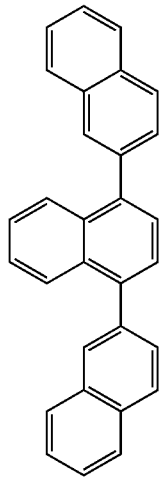
(111)
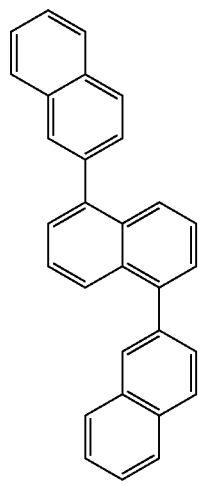

[Chemical Formula 19]
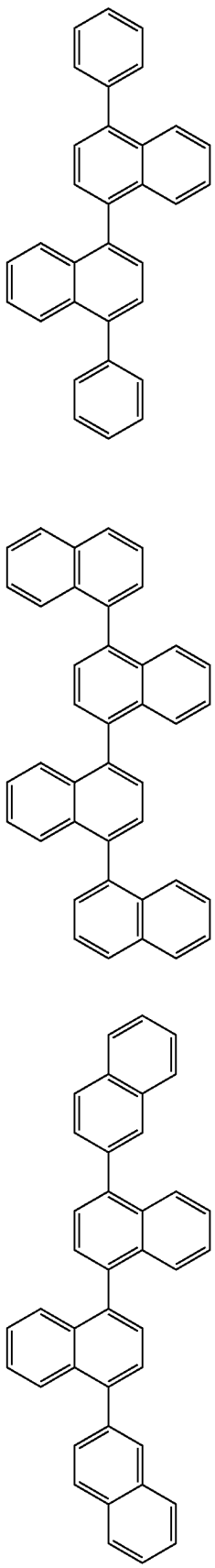
(112)
(113)
(114)
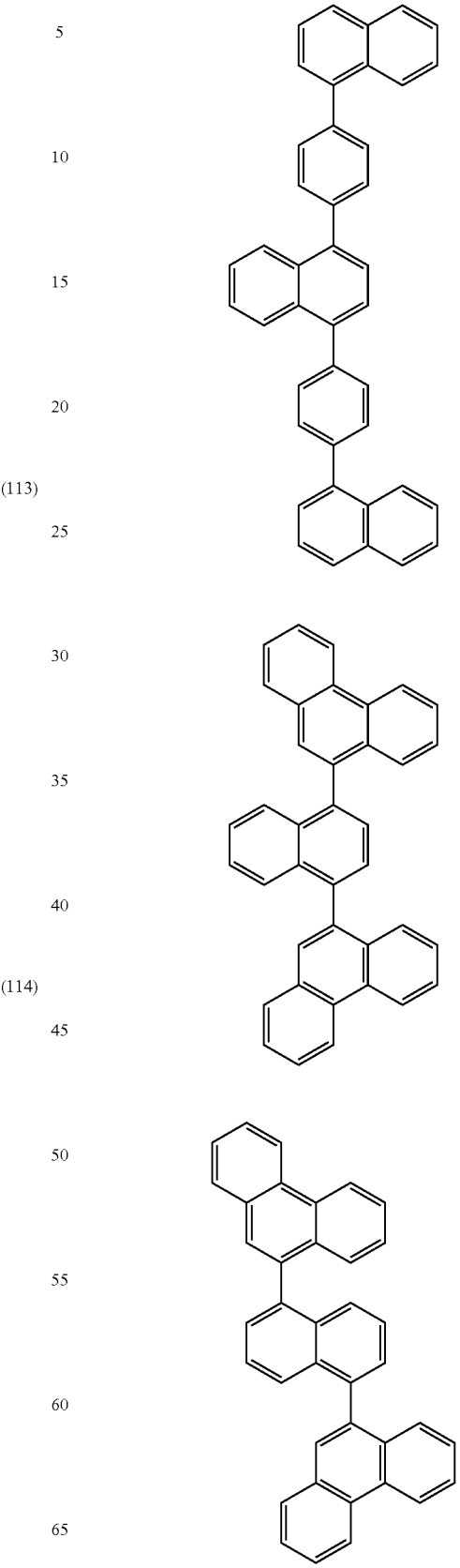
(115)
(116)
(117)

(118) 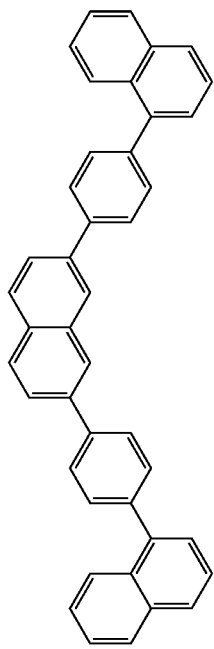
(119) 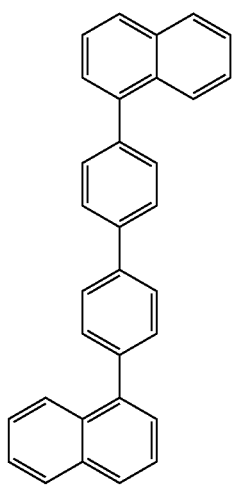
(120) 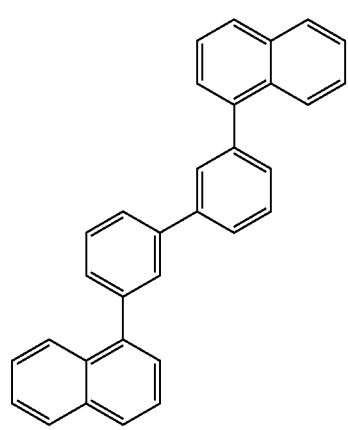
(121) 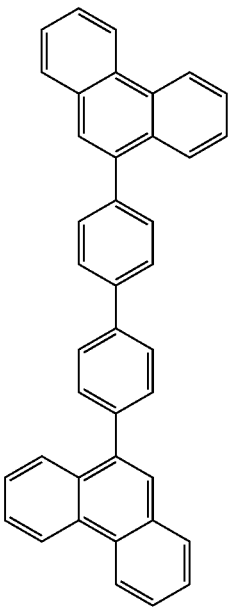
(122) 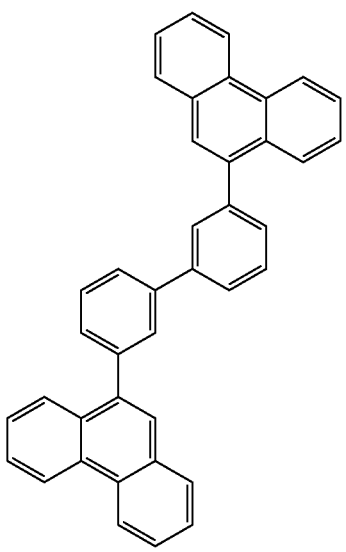
[Chemical Formula 20]
(123) 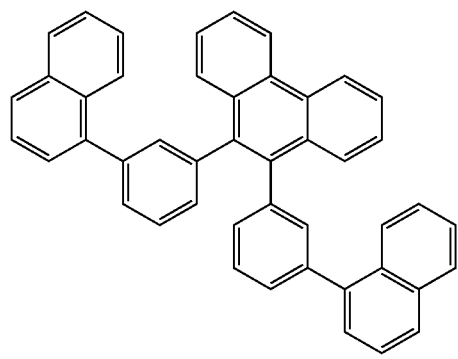

-continued
(124)
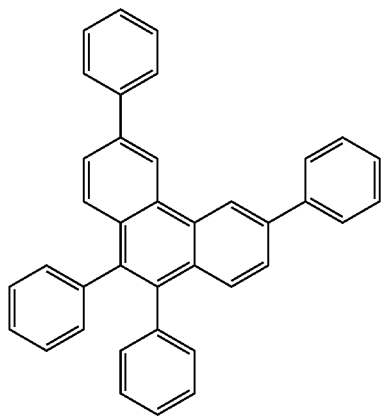
(125)
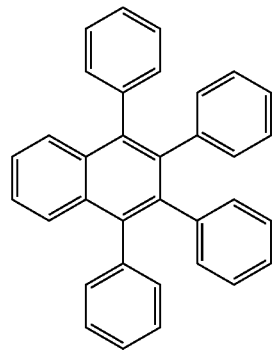
(126)
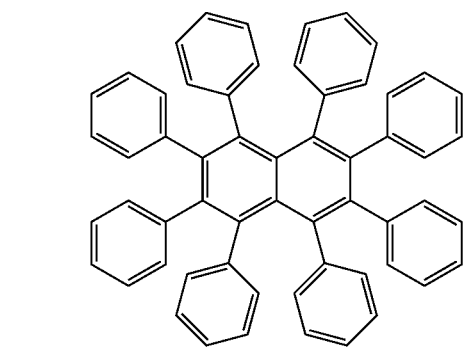
(127)
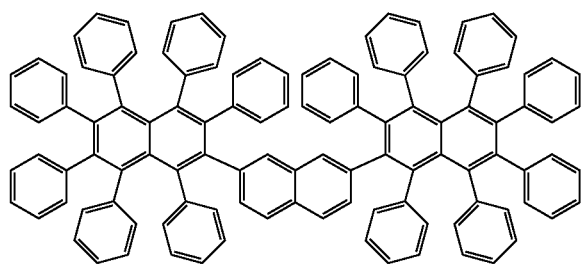
-continued
[Chemical Formula 21]
(130)
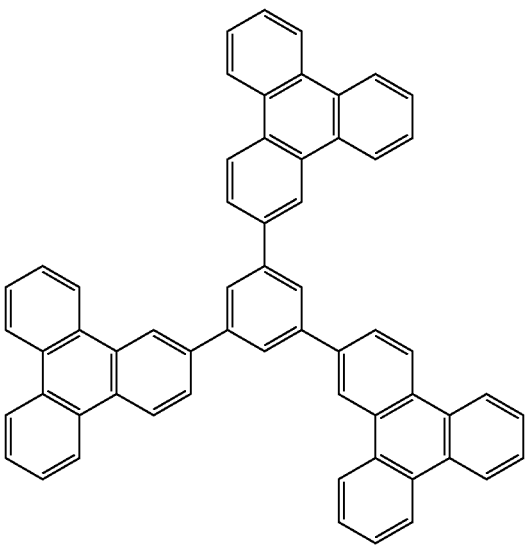
(131)
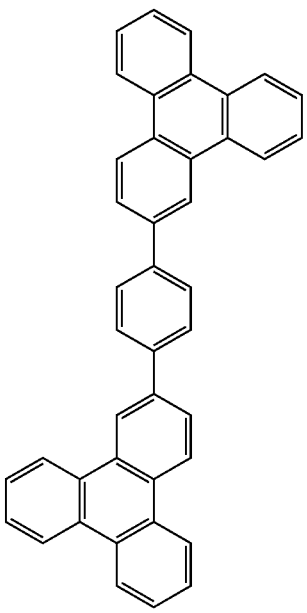

(132)
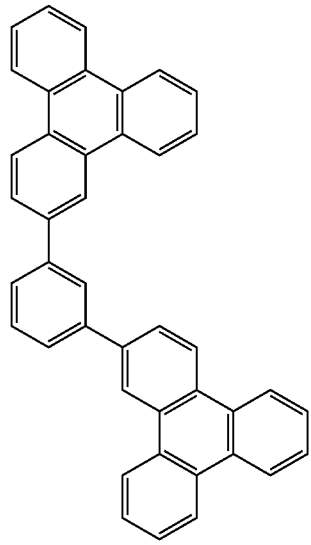
(134)
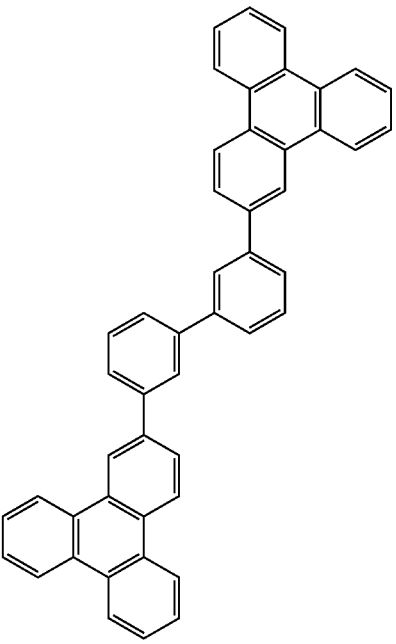
(133)
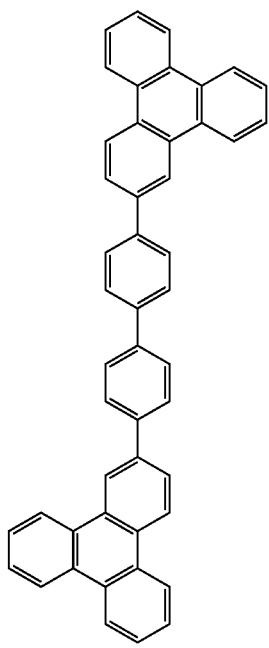
(135)
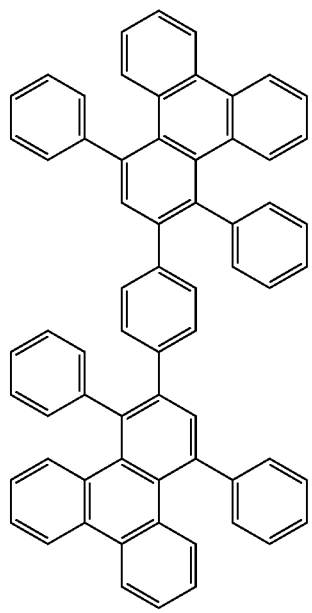

[Chemical Formula 22]
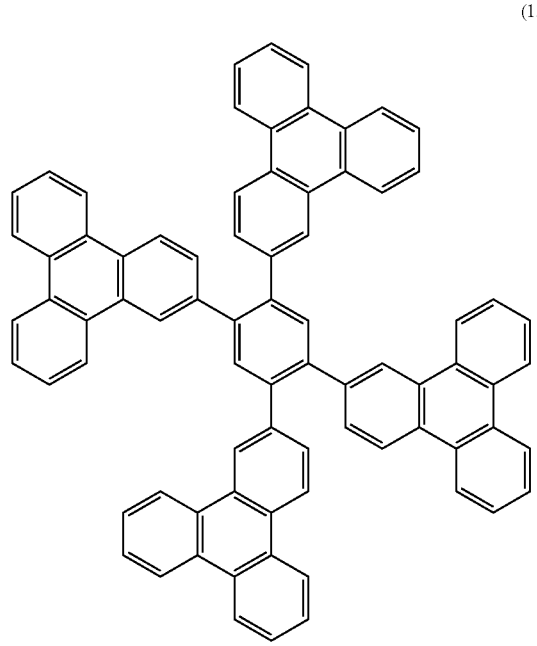
(136)
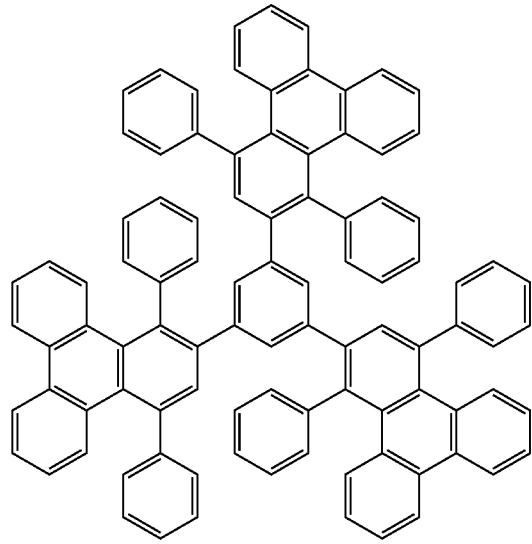
(137)
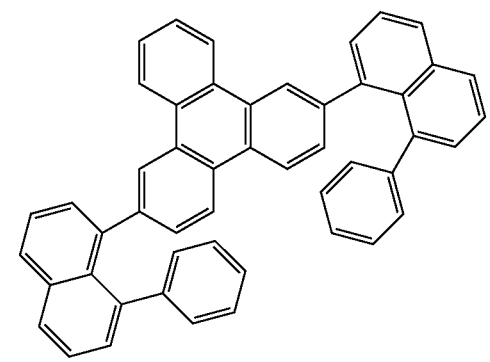
(138)
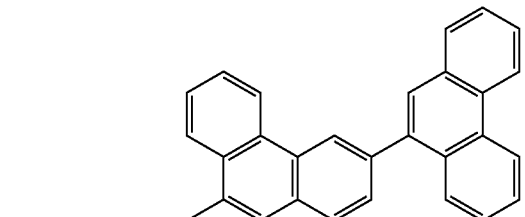
(139)
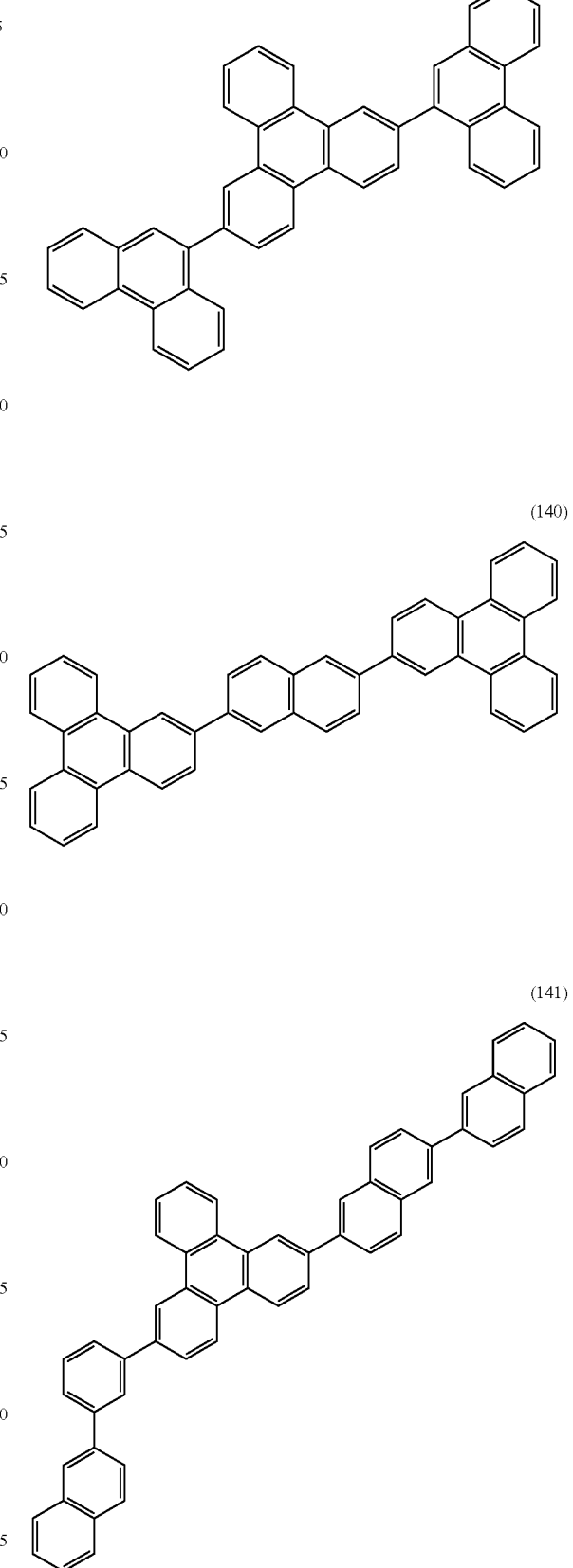
(140)
(141)

[Chemical Formula 23]

(142)
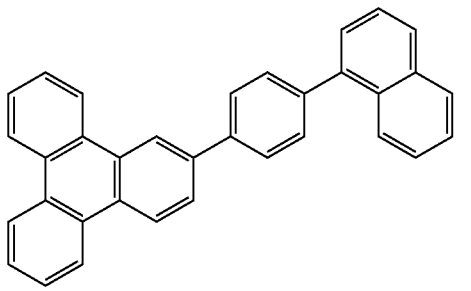

(143)
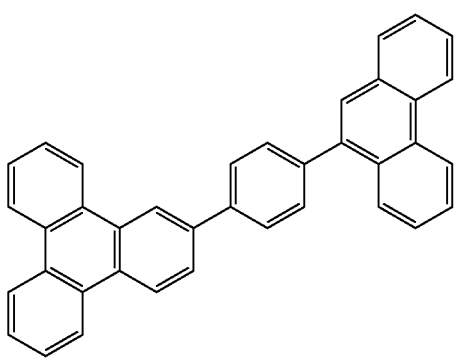

(144)
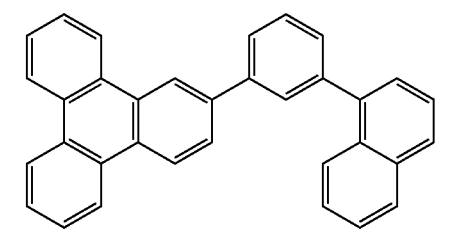

(145)
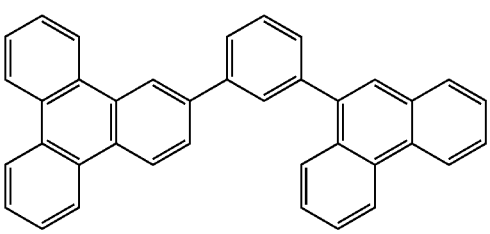

Next, the inorganic compound that can be used for the composite material of one embodiment of the present invention is described.

It is possible to use an inorganic compound exhibiting an electron-accepting property with respect to the hydrocarbon compound used for the composite material of one embodiment of the present invention. Iron(III) chloride, aluminum chloride, and the like are examples of inorganic compounds having a high electron-accepting property.

Alternatively, a transition metal oxide can be used as the inorganic compound for the composite material of one embodiment of the present invention. It is preferable to use an oxide of a metal belonging to any of Groups 4 to 8 of the periodic table. It is particularly preferable to use titanium oxide, vanadium oxide, tantalum oxide, molybdenum oxide, tungsten oxide, rhenium oxide, ruthenium oxide, chromium oxide, zirconium oxide, hafnium oxide, or silver oxide. Molybdenum oxide is particularly easy to handle among them, because it is easily deposited by evaporation, has a low hygroscopic property, and is stable.

A transition metal oxide is considered not to have a very high electron-accepting property (considered to have low reactivity), as compared to a strong Lewis acid such as iron(III) chloride mentioned above. In the composite material of one embodiment of the present invention, as described above, absorption due to charge-transfer interaction less occurs (or light absorption hardly occurs). It is difficult to prove from these that a transition metal oxide acts as an electron acceptor in a general sense in the present invention. On the other hand, as described in the following examples, there is an experimental fact that the composite material of one embodiment of the present invention conducts a larger amount of current than the hydrocarbon compound alone can do, when an electric field is applied. Thus, it is probable that in the composite material of one embodiment of the present invention, use of a transition metal oxide facilitates carrier generation at least with an assistance of application of an electric field. Therefore, in this specification, an inorganic compound (such as a transition metal oxide mentioned above) in the composite material is considered to have an electron-accepting property as long as carriers are generated at least with an assistance of application of an electric field.

It is preferable that the HOMO level of the hydrocarbon compound included in the above-described composite material of one embodiment of the present invention is lower than or equal to −5.7 eV when measured by photoelectron spectroscopy. As described above, naphthalene, phenanthrene, and triphenylene have very low HOMO levels. Therefore, the hydrocarbon compound including a naphthalene skeleton, a phenanthrene skeleton, or a triphenylene skeleton, which is used in one embodiment of the present invention, can by itself have a HOMO level as low as or lower than −5.7 eV with ease.

In the case where the hydrocarbon compound has a low HOMO level, it can be considered that the hydrocarbon compound is excellent in hole injection into another organic compound, but has difficulty receiving holes from an electrically conductive material typified by Al or ITO (having a work function of approximately 3 eV to 5 eV). However, formation of such a composite material as in one embodiment of the present invention enables the problem in hole injection from an electrode to be overcome while maintaining an excellent property of hole injection into another organic compound. When the composite material is used for a light-emitting element, such a property of the composite material contributes to a reduction in driving voltage. Further, the high light-transmitting property leads to an increase in emission efficiency. Furthermore, the deep HOMO level is considered to prevent carrier accumulation in a light-emitting element, leading to a longer lifetime.

As described above, the composite material of one embodiment of the present invention is a material having a low HOMO level and a high carrier-transport property. In addition, the composite material of one embodiment of the present invention is a material having an excellent property of carrier injection into an organic compound. Further, the composite material of one embodiment of the present invention is a material in which absorption due to charge-transfer interaction is unlikely to occur. Furthermore, the composite material of one embodiment of the present invention is a material having a high light-transmitting property.

Therefore, the composite material of one embodiment of the present invention can be used for a light-emitting element or a semiconductor element such as a photoelectric conversion element or a transistor.

Furthermore, the composite material of one embodiment of the present invention has excellent properties of carrier-transport and carrier injection into an organic compound and can accordingly realize a low driving voltage when used for a light-emitting element or the like.

The composite material of one embodiment of the present invention has a light-transmitting property and can accordingly realize high emission efficiency when used for a light-emitting element or the like.

The composite material of one embodiment of the present invention suppresses charge accumulation and can accordingly realize an element having a long lifetime when used for a light-emitting element or the like.

Note that this embodiment can be implemented in appropriate combination with any of the other embodiments.

Embodiment 2

In this embodiment, a light-emitting element of one embodiment of the present invention is described with reference to FIGS. 1A to 1C.

In a light-emitting element of this embodiment, an EL layer (a layer containing a light-emitting substance) is interposed between a pair of electrodes. The EL layer includes at least a layer containing the composite material of one embodiment of the present invention described in Embodiment 1 and a light-emitting layer. The EL layer may additionally include another layer. For example, the EL layer may include a layer containing a substance having a high carrier-injection property or a layer containing a substance having a high carrier-transport property so that a light-emitting region is formed in a region away from the electrodes, that is, so that carriers recombine in a region away from the electrodes. In this specification, the layer containing a substance having a high carrier-injection or a high carrier-transport property is also referred to as functional layer which functions, for instance, to inject or transport carriers. As a functional layer, a hole-injection layer, a hole-transport layer, an electron-injection layer, an electron-transport layer, or the like can be used. Note that in this embodiment, the layer containing the composite material of one embodiment of the present invention is used as a hole-injection layer.

It is preferable that one or more layers (such as a hole-transport layer) be provided between the layer containing the composite material of one embodiment of the present invention and the light-emitting layer. Accordingly, it is possible to suppress quenching (an efficiency decrease) caused by transfer of excitation energy generated in the light-emitting layer to the layer containing the composite material, and it is possible to obtain a more efficient element.

In the light-emitting element illustrated in FIG. 1A, an EL layer 102 is provided between a first electrode 101 and a second electrode 108. In the EL layer 102, a hole-injection layer 701, a hole-transport layer 702, a light-emitting layer 703, an electron-transport layer 704, and an electron-injection layer 705 are stacked in this order over the first electrode 101. Note that, in the light-emitting element described in this embodiment, the first electrode 101 functions as an anode and the second electrode 108 functions as a cathode.

As a support of the light-emitting element (see a substrate 100 in FIG. 1A), a glass substrate, a quartz substrate, a plastic substrate, or the like can be used, for example. Furthermore, a flexible substrate may be used. The flexible substrate is a substrate that can be bent, such as a plastic substrate made of polycarbonate, polyarylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as long as they can function as a support of the light-emitting element.

For the first electrode 101, any of a variety of metals, alloys, electrically conductive compounds, mixtures thereof, and the like can be used. Examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering, but may be formed by application of a sol-gel method or the like. For example, a film of indium oxide-zinc oxide can be formed by a sputtering method using a target obtained by adding 1 wt % to 20 wt % of zinc oxide to indium oxide. Further, an IWZO film can be formed by a sputtering method using a target obtained by adding 0.5 wt % to 5 wt % of tungsten oxide and 0.1 wt % to 1 wt % of zinc oxide to indium oxide. Other examples are gold, platinum, nickel, tungsten, chromium, molybdenum, iron, cobalt, copper, palladium, nitrides of metal materials (e.g., titanium nitride), and the like.

As a material of the first electrode 101, it is preferable to use a material having a high work function (a work function higher than or equal to 4.0 eV). Note that in a light-emitting element having a structure where the first electrode 101 and the layer containing the composite material of one embodiment of the present invention are in contact with each other, a material used for the first electrode 101 is not limited to a material having a high work function and can be a material having a low work function. For example, aluminum, silver, an alloy including aluminum (e.g., Al—Si), or the like can also be used.

The hole-injection layer 701 is a layer that contains the composite material of one embodiment of the present invention.

The hydrocarbon compound (see Embodiment 1) used for the composite material of one embodiment of the present invention has a low HOMO level and an excellent property of hole injection into the hole-transport layer 702 and the light-emitting layer 703. On the other hand, an injection barrier is generated between the first electrode 101 and the hydrocarbon compound, and holes are not easily injected from the first electrode 101.

However, in the light-emitting element of one embodiment of the present invention, the composite material of one embodiment of the present invention is used for the hole-injection layer 701; thus, the injection barrier between the first electrode 101 and the hole-injection layer 701 can be reduced. Therefore, it is possible to realize an element having a low injection barrier from the first electrode 101 to the light-emitting layer 703 and a high carrier-injection property, and it is possible to provide a light-emitting element having a low driving voltage.

Furthermore, the composite material of one embodiment of the present invention has high carrier-generation efficiency and a high carrier-transport property. Therefore, with the use of the composite material of one embodiment of the present invention, it is possible to realize a light-emitting element having high emission efficiency.

In addition, the hydrocarbon compound does not exhibit high absorption peak in the visible light region. Furthermore, the hydrocarbon compound has a low HOMO level, and absorption due to charge-transfer interaction with the inorganic compound is unlikely to occur. Thus, the composite material of one embodiment of the present invention is unlikely to exhibit an absorption peak in the visible light region, and has a high light-transmitting property. Therefore, this also shows that with the use of the composite material of one embodiment of the present invention, it is possible to realize a light-emitting element having high emission efficiency.

The composite material of one embodiment of the present invention can suppress charge accumulation; therefore, a light-emitting element having a long lifetime can be provided.

There is no limitation on the emission color of a light-emitting element to which the composite material of one embodiment of the present invention is applied. In addition, it does not matter whether a light-emitting element to which the composite material of one embodiment of the present invention is applied exhibits fluorescence or phosphorescence. In any light-emitting element, the composite material of one embodiment of the present invention hardly causes absorption of emission energy and reduction of efficiency, and thus can be suitably used for a hole-injection layer.

The hole-transport layer 702 is a layer that contains a substance having a high hole-transport property. As a material of the hole-transport layer 702, the hydrocarbon compound used for the composite material of one embodiment of the present invention may be used. Other examples of the substance having a high hole-transport property are aromatic amine compounds such as 4,4'-bis[N-(1-naphthyl)-N-phenylamino]biphenyl (abbreviation: NPB or α-NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm$^2$/Vs or more. Note that other than these substances, any substance that has a property of transporting more holes than electrons may be used. Note that the layer containing a substance having a high hole-transport property is not limited to a single layer, and may be a stack of two or more layers containing any of the above substances.

For the hole-transport layer 702, a carbazole derivative such as 4,4'-di(N-carbazolyl)biphenyl (abbreviation: CBP), 9-[4-(10-phenyl-9-anthryl)phenyl]-9H-carbazole (abbreviation: CzPA), or 9-phenyl-3-[4-(10-phenyl-9-anthryl)phenyl]-9H-carbazole (abbreviation: PCzPA) or an anthracene derivative such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth) may be used.

In particular, the hydrocarbon compound in the composite material of one embodiment of the present invention has a low HOMO level; therefore, a material having a low HOMO level can be used also for the hole-transport layer. With such a structure, it is possible to prevent charge accumulation at the interface between the light-emitting layer and the hole-transport layer, and it is possible to extend the lifetime of the light-emitting element. Specifically, for the hole-transport layer, a HOMO level lower than or equal to −5.6 eV is preferred. From such a point of view, as a compound that is used for the hole-transport layer, a carbazole derivative, a dibenzothiophene derivative, a dibenzofuran derivative, an anthracene derivative, or the like is preferable. Alternatively, the hydrocarbon compound used for the composite material of one embodiment of the present invention may be used. In this structure, the hydrocarbon compound used for the composite material of one embodiment of the present invention is preferably used for the hole-injection layer and the hole-transport layer, in which case the HOMO levels are close to each other to reduce carrier injection barrier. The hydrocarbon compound used for the composite material of one embodiment of the present invention which is used for the hole-injection layer and the hydrocarbon compound used for the hole-transport layer are particularly preferably the same materials. Preferably, the hydrocarbon compound used for the composite material of one embodiment of the present invention is used for the hole-transport layer and the light-emitting layer is provided in contact with the hole-transport layer, in which case an element with high reliability can be obtained.

Note that for the hole-transport layer 702, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

The light-emitting layer 703 is a layer that contains a light-emitting organic compound. As the light-emitting organic compound, for example, a fluorescent compound which emits fluorescence or a phosphorescent compound which emits phosphorescence can be used.

Examples of a fluorescent compound that can be used for the light-emitting layer 703 are the following light-emitting materials, for example: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

The hydrocarbon compound used for the composite material of one embodiment of the present invention exhibits purple to blue fluorescence. Therefore, the hydrocarbon compound used for the composite material of one embodiment of the present invention can be used as a fluorescent compound in the light-emitting layer 703.

Examples of a phosphorescent compound that can be used for the light-emitting layer 703 are the following light-emitting materials: materials that emit blue light, such as bis[2-(4',6'-difluorophenyl)pyridinato-N,C$^{2'}$]iridium(III)tetrakis(1-pyrazolyl)borate (abbreviation: FIr6), bis[2-(4',6'- difluorophenyl)pyridinato-N,C$^{2'}$]iridium(III)picolinate (abbreviation: FIrpic), bis {2-[3',5'-bis(trifluoromethyl)phenyl]pyridinato-N,C$^{2'}$}iridium(III)picolinate (abbreviation: [Ir(CF$_3$ppy)$_2$(pic)], and bis[2-(4',6'-difluorophenyl)pyridinato-N,C$^{2'}$]iridium(III)acetylacetonate (abbreviation: FIr(acac)]; materials that emit green light, such as tris(2-phenylpyridinato-N,C$^{2'}$)iridium(III) (abbreviation: [Ir(ppy)$_3$]), bis(2-phenylpyridinato-N,C$^{2'}$)iridium(III)acetylacetonate (abbreviation: [Ir(ppy)$_2$(acac)]), bis(1,2-diphenyl-1H-benzimidazolato)iridium(III)acetylacetonate (abbreviation: [Ir(pbi)$_2$(acac)]), bis(benzo[h]quinolinato)iridium(III)acetylacetonate (abbreviation: [Ir(bzq)$_2$(acac)], and tris(benzo[h]quinolinato)iridium(III) (abbreviation: [Ir(bzq)$_3$]); materials that emit yellow light, such as bis(2,4-diphenyl-1,3-oxazolato-N,C$^{2'}$)iridium(III)acetylacetonate (abbreviation: [Ir(dpo)$_2$(acac)]), bis[2-(4'-(perfluorophenylphenyl)pyridinato]iridium(III)acetylacetonate (abbreviation: [Ir(p-PF-ph)$_2$(acac)], bis(2-phenylbenzothiazolato-N,C$^{2'}$)iridium(III)acetylacetonate (abbreviation: [Ir(bt)$_2$(acac)], (acetylacetonato)bis[2,3-bis(4-fluorophenyl)-5-methylpyrazinato]iridium(III) (abbreviation: [Ir(Fdppr-Me)$_2$(acac)], and (acetylacetonato)bis {2-(4-methoxyphenyl)-3,5-dimethylpyrazinato}iridium(III) (abbreviation: [Ir(dmmoppr)$_2$(acac)]; materials that emit orange light, such as tris(2-phenylquinolinato-N,C$^{2'}$)iridium(III) (abbreviation: [Ir(pq)$_3$]), bis(2-phenylquinolinato-N,C$^{2'}$)iridium(III)acetylacetonate (abbreviation: [Ir(pq)$_2$(acac)], (acetylacetonato)bis(3,5-dimethyl-2-phenylpyrazinato)iridium(III) (abbreviation: [Ir(mppr-Me)$_2$(acac)], and (acetylacetonato)bis(5-isopropyl-3-methyl-2-phenylpyrazinato)iridium(III) (abbreviation: [Ir(mppr-iPr)$_2$(acac)]; and materials that emit red light, for example, organometallic complexes, such as bis[2-(2'-benzo[4,5-a]thienyl)pyridinato-N,C$^{3'}$)iridium(III)acetylacetonate (abbreviation: [Ir(btp)$_2$(acac)], bis(1-phenylisoquinolinato-N,C$^{2'}$)iridium(III)acetylacetonate (abbreviation: [Ir(piq)$_2$(acac), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)], (dipivaloylmethanato)bis(2,3,5-triphenylpyrazinato)iridium(III) (abbreviation: [Ir(tppr)$_2$(dpm)], and (2,3,7,8,12,13,17,18-octaethyl-21H,23H-porphyrin)platinum(II) (abbreviation: PtOEP). Any of the following rare earth metal complexes can be used as a phosphorescent compound: tris(acetylacetonato)(monophenanthroline)terbium(III) (abbreviation: Tb(acac)$_3$(Phen)); tris(1,3-diphenyl-1,3-propanedionato)(monophenanthroline)europium(III) (abbreviation: Eu(DBM)$_3$(Phen)]; and tris[1-(2-thenoyl)-3,3,3-trifluoroacetonato](monophenanthroline)europium(III) (abbreviation: Eu(TTA)$_3$(Phen)), because their light emission is from a rare earth metal ion (electronic transition between different multiplicities) in such a rare earth metal complex.

Note that the light-emitting layer 703 may have a structure in which any of the above-described light-emitting organic compounds (a guest material) is dispersed into another substance (a host material). A variety of substances can be used as the host material, and it is preferable to use a substance that has a lowest unoccupied molecular orbital level (LUMO level) higher than that of a guest material and has a HOMO level lower than that of the guest material. In the case where the guest material is a fluorescent compound, the host material preferably has a high singlet excitation energy level (S1 level). In the case where the guest material is a phosphorescent compound, the host material preferably has a high triplet excitation energy level (T1 level).

The hydrocarbon compound used for the composite material of one embodiment of the present invention has a high LUMO level, a low HOMO level, a high S1 level, and a high T1 level. Therefore, the hydrocarbon compound can be used as the host material, and specifically as a host material for a fluorescent compound which emits visible light or a phosphorescent compound which emits yellow light or light having a longer wavelength than yellow light.

Specific examples of the host material that can be used are the following materials: metal complexes, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds, such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like.

Plural kinds of host materials can also be used. For example, in order to suppress crystallization, a substance such as rubrene which suppresses crystallization, may be further added. In addition, in order to transfer energy or transport carriers to the guest material more efficiently, a material having a high hole mobility (e.g., a material having an amine skeleton, such as NPB, or a material having a carbazole skeleton, such as CBP) or a material having a high electron mobility (e.g., a material having a heterocyclic skeleton, such as Alq) may be further added.

With a structure in which a guest material is dispersed in a host material, crystallization of the light-emitting layer 703 can be suppressed. In addition, concentration quenching due to high concentration of the guest material can also be suppressed.

For the light-emitting layer 703, a high molecular compound can be used. Specific examples of materials that emit blue light are poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. Specific examples of materials that emit green light are poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyloxy)-1,4-phenylene)], and the like. Specific examples of materials that emit orange to red light are poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

Further, by providing a plurality of light-emitting layers and making emission colors of the light-emitting layers different, light emission of a desired color can be obtained from the light-emitting element as a whole. For example, the emission colors of first and second light-emitting layers are complementary in a light-emitting element having the two light-emitting layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three or more light-emitting layers.

The electron-transport layer 704 is a layer that contains a substance having a high electron-transport property. Examples of the substance having a high electron-transport property are metal complexes having a quinoline skeleton or a benzoquinoline skeleton, such as tris(8-quinolinolato)aluminum (abbreviation: Alq), tris(4-methyl-8-quinolinolato) aluminum (abbreviation: Almq$_3$), bis(10-hydroxybenzo[h]quinolinato)beryllium (abbreviation: BeBq$_2$), and bis(2-methyl-8-quinolinolato)(4-phenylphenolato)aluminum (abbreviation: BAlq). Other examples are metal complexes having an oxazole-based or thiazole-based ligand, such as bis[2-(2-hydroxyphenyl)benzoxazolato]zinc (abbreviation: Zn(BOX)$_2$) and bis[2-(2-hydroxyphenyl)benzothiazolato]zinc (abbreviation: Zn(BTZ)$_2$). Other than metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly substances having an electron mobility of $10^{-6}$ cm$^2$/Vs or more. Further, the electron-transport layer is not limited to a single layer, and may be a stack of two or more layers containing any of the above substances.

The electron-injection layer 705 is a layer that contains a substance having a high electron-injection property. Examples of the substance that can be used for the electron-injection layer 705 are alkali metals, alkaline earth metals, and compounds thereof, such as lithium, cesium, calcium, lithium fluoride, cesium fluoride, calcium fluoride, and lithium oxide, rare earth metal compounds, such as erbium fluoride, and the above-mentioned substances for forming the electron-transport layer 704.

Note that the hole-injection layer 701, the hole-transport layer 702, the light-emitting layer 703, the electron-transport layer 704, and the electron-injection layer 705 which are described above can each be formed by a method, such as an evaporation method (e.g., a vacuum evaporation method), an inkjet method, or a coating method.

In a light-emitting element illustrated in FIG. 2A, the EL layer 102 is provided between a pair of electrodes, the first electrode 101 and the second electrode 108, over the substrate 100. The EL layer 102 includes the hole-injection layer 701, the hole-transport layer 702, the light-emitting layer 703, the electron-transport layer 704, and the electron-injection layer 705. The light-emitting element in FIG. 2A includes the second electrode 108 functioning as a cathode over the substrate 100, the electron-injection layer 705, the electron-transport layer 704, the light-emitting layer 703, the hole-transport layer 702, and the hole-injection layer 701 which are stacked over the second electrode 108 in this order, and the first electrode 101 provided thereover which functions as an anode.

Furthermore, by making emission colors of EL layers different, light of a desired color can be obtained from the light-emitting element as a whole. For example, the emission colors of first and second EL layers are complementary in a light-emitting element having the two EL layers, so that the light-emitting element can be made to emit white light as a whole. Further, the same applies to a light-emitting element having three or more EL layers.

A plurality of EL layers may be stacked between the first electrode 101 and the second electrode 108, as illustrated in FIG. 1B. In that case, a charge-generation layer 803 is preferably provided between a first EL layer 800 and a second EL layer 801 which are stacked. The charge-generation layer 803 can be formed using the composite material of one embodiment of the present invention. The composite material of one embodiment of the present invention has high carrier generation efficiency and a high hole-transport property at the time of voltage application. Therefore, with the use of the composite material of one embodiment of the present invention, it is possible to realize a light-emitting element having a low driving voltage. In addition, it is possible to realize a light-emitting element having high emission efficiency.

Also in this case, the hydrocarbon compound used for the composite material of one embodiment of the present invention can be suitably used for the hole-transport layer in contact with the layer containing the composite material of one embodiment of the present invention or for the light-emitting layer in contact with the hole-transport layer.

In addition, the hydrocarbon compound exhibits no absorption peak in the visible light region. Furthermore, the hydrocarbon compound has a low HOMO level, and absorption due to charge-transfer interaction with the inorganic compound is unlikely to occur. Thus, the composite material of one embodiment of the present invention is unlikely to exhibit an absorption peak in the visible light region, and has a high light-transmitting property. Therefore, this also shows that with the use of the composite material of one embodiment of the present invention, it is possible to realize a light-emitting element having high emission efficiency.

Further, the charge-generation layer 803 may have a stacked structure including a layer containing the composite material of one embodiment of the present invention and a layer containing another material. In that case, as the layer containing another material, a layer containing an electron-donating substance and a substance with a high electron-transport property, a layer formed of a transparent conductive film, or the like can be used. As for a light-emitting element having such a structure, problems such as energy transfer and quenching hardly occur, and a light-emitting element which has both high emission efficiency and a long lifetime can be easily obtained due to expansion in the choice of materials. Moreover, a light-emitting element which provides phosphorescence from one of the EL layers and fluorescence from the other of the EL layers can be readily obtained. Note that this structure can be combined with the above-described structures of the EL layer.

Figure 2B:
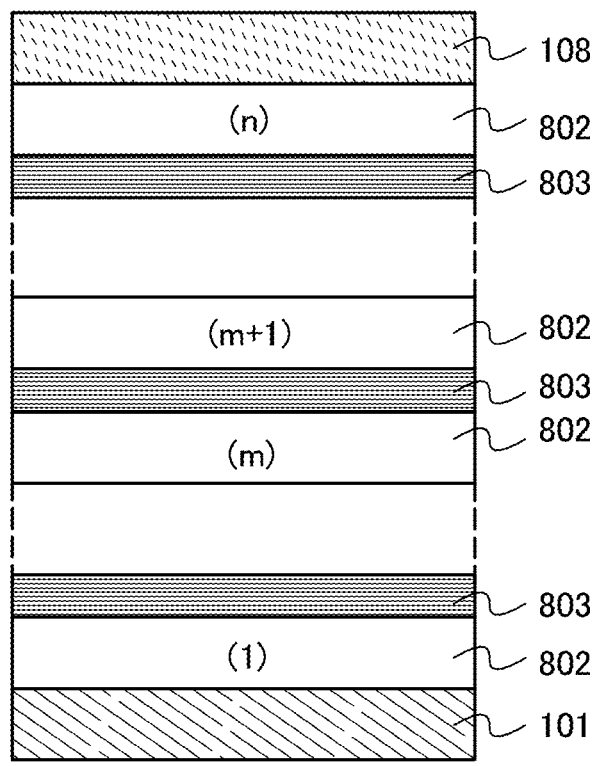

Similarly, a light-emitting element in which three or more EL layers 802 are stacked as illustrated in FIG. 2B can also be employed. As in the light-emitting element according to this embodiment, when a plurality of EL layers with a charge-generation layer interposed therebetween is provided between a pair of electrodes, it is possible to realize an element having a long lifetime which can emit light at a high luminance while current density is kept low.

As illustrated in FIG. 1C, the EL layer may include the hole-injection layer 701, the hole-transport layer 702, the light-emitting layer 703, the electron-transport layer 704, an electron-injection buffer layer 706, an electron-relay layer 707, and a composite material layer 708 which is in contact with the second electrode 108, between the first electrode 101 and the second electrode 108.

It is preferable to provide the composite material layer 708 which is in contact with the second electrode 108, in which case damage caused to the EL layer 102 particularly when the second electrode 108 is formed by a sputtering method can be reduced. The composite material layer 708 can be formed using the composite material of one embodiment of the present invention.

Further, since the above composite material layer 708 functions as a charge generation layer, carriers can be favorably injected from the second electrode 108 into the electron-relay layer 707 by passing through the composite material layer 708.

Further, by providing the electron-injection buffer layer 706, an injection barrier between the composite material layer 708 and the electron-transport layer 704 can be reduced; thus, electrons generated in the composite material layer 708 can be easily injected into the electron-transport layer 704.

A substance having a high electron-injection property, such as an alkali metal, an alkaline earth metal, a rare earth metal, a compound of the above metal (e.g., an alkali metal compound (e.g., an oxide such as lithium oxide, a halide, and a carbonate such as lithium carbonate or cesium carbonate), an alkaline earth metal compound (e.g., an oxide, a halide, and a carbonate), or a rare earth metal compound (e.g., an oxide, a halide, and a carbonate), can be used for the electron-injection buffer layer 706.

Further, in the case where the electron-injection buffer layer 706 contains a substance having a high electron-transport property and a donor substance, the donor substance is preferably added so that the mass ratio of the donor substance to the substance having a high electron-transport property ranges from 0.001:1 to 0.1:1. Note that as the donor substance, an organic compound such as tetrathianaphthacene (abbreviation: TTN), nickelocene, or decamethylnickelocene can be used as well as an alkali metal, an alkaline earth metal, a rare earth metal, a compound of the above metal (e.g., an alkali metal compound (including an oxide of lithium oxide or the like, a halide, and a carbonate such as lithium carbonate or cesium carbonate), an alkaline earth metal compound (including an oxide, a halide, and a carbonate), and a rare earth metal compound (including an oxide, a halide, and a carbonate). Note that as the substance having a high electron-transport property, any of the same materials as the electron-transport layer 704 described above can be used.

Furthermore, it is preferable that the electron-relay layer 707 be formed between the electron-injection buffer layer 706 and the composite material layer 708. The electron-relay layer 707 is not necessarily provided; however, by providing the electron-relay layer 707 having a high electron-transport property, electrons can be rapidly transported to the electron-injection buffer layer 706.

The structure in which the electron-relay layer 707 is interposed between the composite material layer 708 and the electron-injection buffer layer 706 is a structure in which the acceptor substance contained in the composite material layer 708 and the donor substance contained in the electron-injection buffer layer 706 are less likely to interact with each other, and thus their functions hardly interfere with each other. Therefore, an increase in driving voltage can be suppressed.

The electron-relay layer 707 contains a substance having a high electron-transport property and is formed so that the LUMO level of the substance having a high electron-transport property is located between the LUMO level of the acceptor substance contained in the composite material layer 708 and the LUMO level of the substance having a high electron-transport property contained in the electron-transport layer 704. In the case where the electron-relay layer 707 contains a donor substance, the donor level of the donor substance is controlled so as to be located between the LUMO level of the acceptor substance contained in the composite material layer 708 and the LUMO level of the substance having a high electron-transport property contained in the electron-transport layer 704. As a specific value of the energy level, the LUMO level of the substance having a high electron-transport property contained in the electron-relay layer 707 is preferably higher than or equal to −5.0 eV, more preferably higher than or equal to −5.0 eV and lower than or equal to −3.0 eV.

As the substance having a high electron-transport property contained in the electron-relay layer 707, a phthalocyanine-based material or a metal complex having a metal-oxygen bond and an aromatic ligand is preferably used.

As the phthalocyanine-based material contained in the electron-relay layer 707, for example, any of CuPc, a phthalocyanine tin(II) complex (SnPc), a phthalocyanine zinc complex (ZnPc), cobalt(II) phthalocyanine, β-form (CoPc), phthalocyanine iron (FePc), and vanadyl 2,9,16,23-tetraphenoxy-29H,31H-phthalocyanine (PhO-VOPc), is preferably used.

As the metal complex having a metal-oxygen bond and an aromatic ligand, which is contained in the electron-relay layer 707, a metal complex having a metal-oxygen double bond is preferably used. The metal-oxygen double bond has an acceptor property (a property of easily accepting electrons); thus, electrons can be transferred (donated and accepted) more easily. Further, the metal complex having a metal-oxygen double bond is considered stable. Thus, the use of the metal complex having the metal-oxygen double bond enables the light-emitting element to be driven more stably at low voltage.

As the metal complex having a metal-oxygen bond and an aromatic ligand, a phthalocyanine-based material is preferable. Specifically, any of vanadyl phthalocyanine (VOPc), a phthalocyanine tin(IV) oxide complex (SnOPc), and a phthalocyanine titanium oxide complex (TiOPc) is preferable because a metal-oxygen double bond is likely to act on another molecular in terms of a molecular structure and an acceptor property is high.

Note that as the phthalocyanine-based materials described above, a phthalocyanine-based material having a phenoxy group is preferable. Specifically, a phthalocyanine derivative having a phenoxy group, such as PhO-VOPc, is preferable. The phthalocyanine derivative having a phenoxy group is soluble in a solvent; thus, the phthalocyanine derivative has an advantage of being easily handled during formation of a light-emitting element and an advantage of facilitating maintenance of an apparatus used for film formation.

The electron-relay layer 707 may further contain a donor substance. As the donor substance, an organic compound such as tetrathianaphthacene (abbreviation: TTN), nickelocene, or decamethylnickelocene can be used as well as an alkali metal, an alkaline earth metal, a rare earth metal, and a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). When such a donor substance is contained in the electron-relay layer 707, electrons can be transferred easily and the light-emitting element can be driven at lower voltage.

In the case where a donor substance is contained in the electron-relay layer 707, other than the materials described above as the substance having a high electron-transport property, a substance having a LUMO level higher than the acceptor level of the acceptor substance contained in the composite material layer 708 can be used. Specifically, it is preferable to use a substance having a LUMO level higher than or equal to −5.0 eV, preferably higher than or equal to −5.0 eV and lower than or equal to −3.0 eV. As examples of such a substance, a perylene derivative, a nitrogen-containing condensed aromatic compound, and the like are given. Note that a nitrogen-containing condensed aromatic compound is preferably used for the electron-relay layer 707 because of its stability.

Specific examples of the perylene derivative are 3,4,9,10-perylenetetracarboxylic dianhydride (abbreviation: PTCDA), 3,4,9,10-perylenetetracarboxylic-bis-benzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like.

Specific examples of the nitrogen-containing condensed aromatic compound are pyrazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT(CN)$_6$), 2,3-diphenylpyrido[2,3-b]pyrazine (abbreviation: 2PYPR), 2,3-bis(4-fluorophenyl)pyrido[2,3-b]pyrazine (abbreviation: F2PYPR), and the like.

Besides, 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8-pentadecafluorooctyl)-1,4,5,8-naphthalenetetracarboxylic diimide (abbreviation: NTCDI-C8F), 3',4'-dibutyl-5,5"-bis(dicyanomethylene)-5,5"-dihydro-2,2':5',2"-terthiophen (abbreviation: DCMT), methanofullerene (e.g., [6,6]-phenyl C$_{61}$ butyric acid methyl ester), or the like can be used.

Note that in the case where a donor substance is contained in the electron-relay layer 707, the electron-relay layer 707 may be formed by a method such as co-evaporation of the substance having a high electron-transport property and the donor substance.

The hole-injection layer 701, the hole-transport layer 702, the light-emitting layer 703, and the electron-transport layer 704 can each be formed using any of the above-described materials. In particular, the hole-injection layer 701 can be formed using the composite material of one embodiment of the present invention. Further, the hydrocarbon compound used for the composite material of one embodiment of the present invention can be suitably used for each of the hole-transport layer 702 and the light-emitting layer 703.

Note that this embodiment can be implemented in appropriate combination with any of the other embodiments.

Embodiment 3

In this embodiment, a light-emitting device including a light-emitting element of one embodiment of the present invention is described with reference to FIGS. 3A and 3B. Note that FIG. 3A is a top view illustrating the light-emitting device, and FIG. 3B is a cross-sectional view taken along lines A-B and C-D of FIG. 3A.

The light-emitting device of this embodiment includes a source side driver circuit 401 and a gate side driver circuit 403 which are driver circuit portions, a pixel portion 402, a sealing substrate 404, a sealing material 405, a flexible printed circuit (FPC) 409, and an element substrate 410. A portion enclosed by the sealing material 405 is a space.

A lead wiring 408 is a wiring for transmitting signals that are to be input to the source side driver circuit 401 and the gate side driver circuit 403, and receives a video signal, a clock signal, a start signal, a reset signal, and the like from the FPC 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Figure 3A:
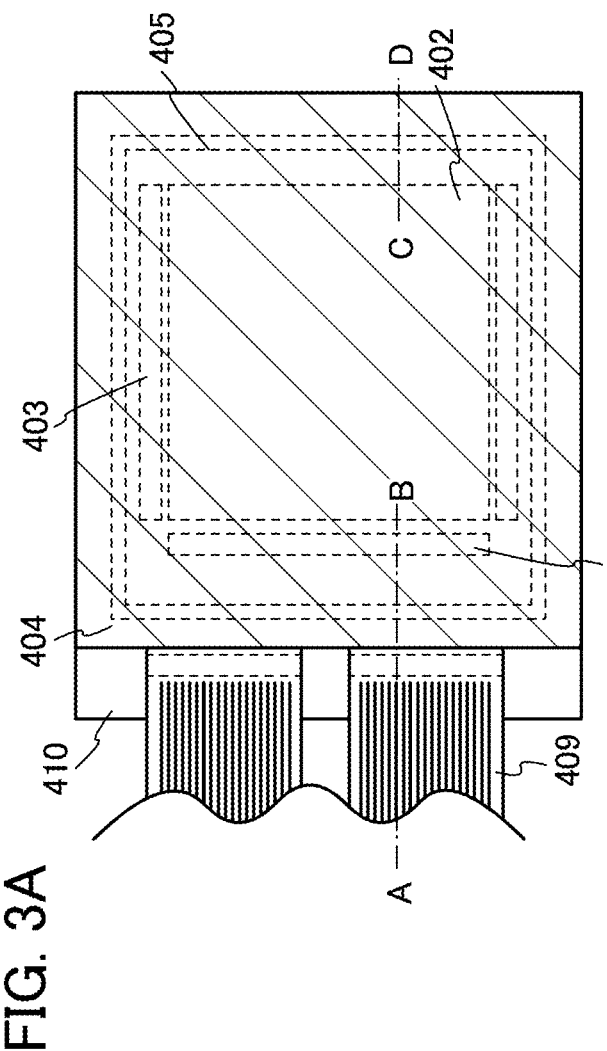
FIGS. 3A and 3B illustrate a light-emitting device of one embodiment of the present invention.
Figure 3B:
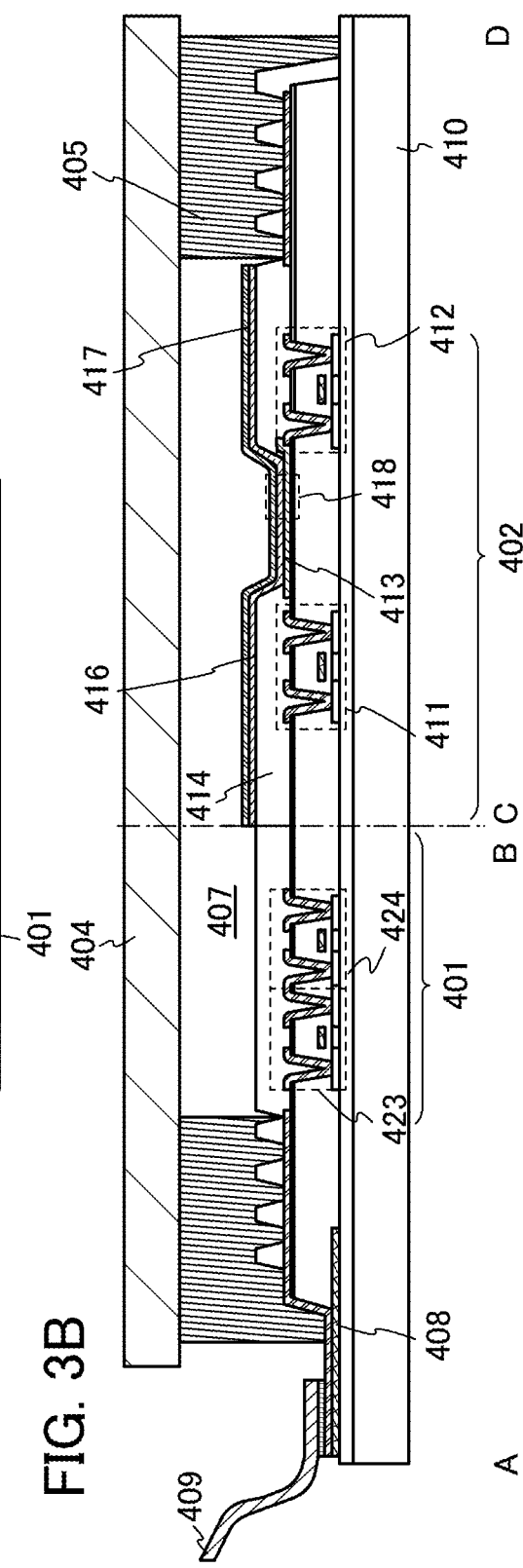

The driver circuit portion and the pixel portion are formed over the element substrate 410 illustrated in FIG. 3A. In FIG. 3B, the source side driver circuit 401 which is the driver circuit portion and one pixel in the pixel portion 402 are illustrated.

Note that as the source side driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 µm to 3 μm). For the insulator 414, it is also possible to use either a negative type that becomes insoluble in an etchant by light irradiation or a positive type that becomes soluble in an etchant by light irradiation.

An EL layer 416 and a second electrode 417 are formed over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum, and a titanium nitride film, or the like. Note that, when a stacked layer structure is employed, resistance of a wiring is low and an excellent ohmic contact is obtained.

In addition, the EL layer 416 is formed by any of various methods such as an evaporation method using an evaporation mask, a droplet discharging method like an inkjet method, a printing method, and a spin coating method. The EL layer 416 includes the composite material of one embodiment of the present invention which is described in Embodiment 1. Further, another material contained in the EL layer 416 may be a low molecular material, an oligomer, a dendrimer, a high molecular material, or the like.

As a material used for the second electrode 417 which is formed over the EL layer 416 and functions as a cathode, it is preferable to use a material having a low work function (e.g., Al, Mg, Li, Ca, or an alloy or a compound thereof such as Mg—Ag, Mg—In, or Al—Li). In order that light generated in the EL layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

Further, the sealing substrate 404 is bonded to the element substrate 410 with the sealing material 405, so that a light-emitting element 418 is provided in the space 407 enclosed by the element substrate 410, the sealing substrate 404, and the sealing material 405. The space 407 is filled with a filler, and may be filled with an inert gas (such as nitrogen or argon) or the sealing material 405.

Note that an epoxy-based resin is preferably used as the sealing material 405. Such a material preferably allows as little moisture and oxygen as possible to penetrate. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element of one embodiment of the present invention can be obtained.

Figure 4A:
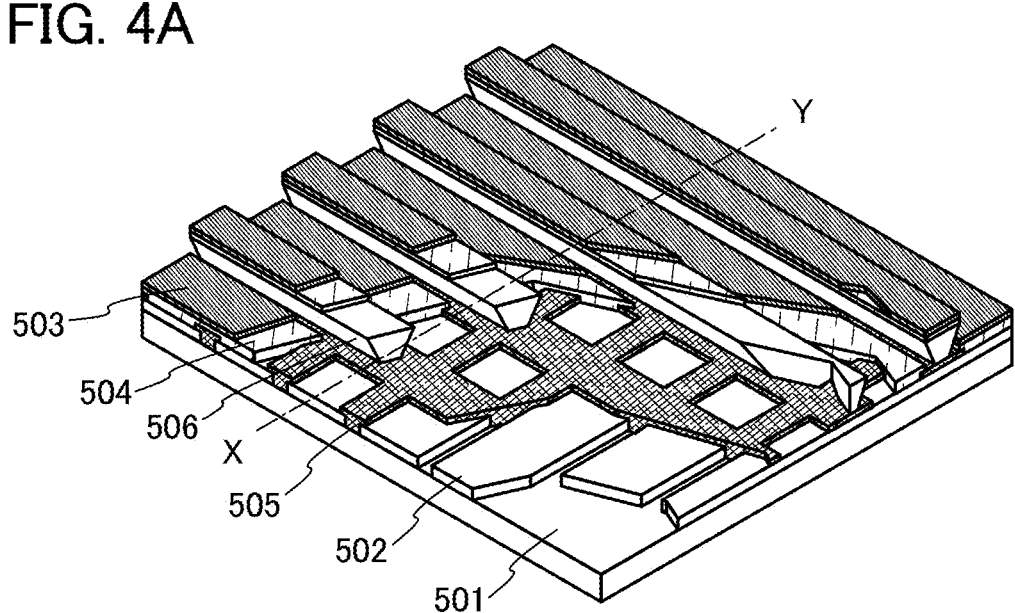
FIGS. 4A and 4B illustrate a light-emitting device of one embodiment of the present invention.
Figure 4B:
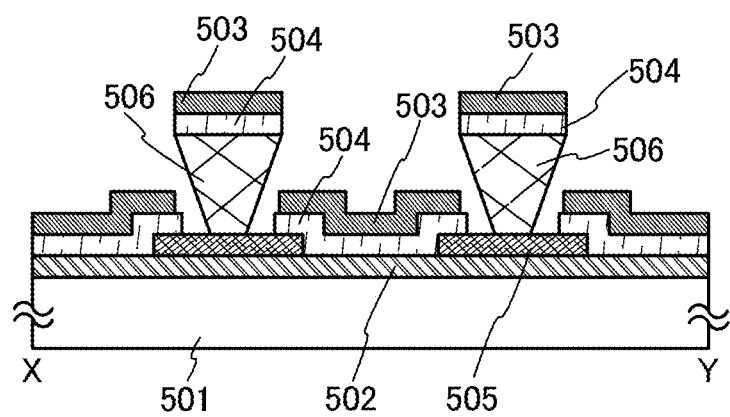

Further, a light-emitting element of the present invention can be used for a passive matrix light-emitting device as well as the above active matrix light-emitting device. FIGS. 4A and 4B illustrate a perspective view and a cross-sectional view of a passive matrix light-emitting device including a light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (a side parallel to the plane of the insulating layer 505 and in contact with the insulating layer 505) is shorter than the upper side (a side parallel to the plane of the insulating layer 505 and not being in contact with the insulating layer 505). With the partition layer 506 provided in such a way, a defect of a light-emitting element due to crosstalk or the like can be prevented.

Thus, the passive matrix light-emitting device including a light-emitting element of one embodiment of the present invention can be obtained.

Examples of light-emitting devices to which one embodiment of the present invention is applied are illustrated in FIGS. 27A to 27C. FIG. 27A is a top view illustrating the light-emitting devices, and FIGS. 27B and 27C are cross-sectional views taken along the line E-F of FIG. 27A.

Light-emitting devices 900 illustrated in FIGS. 27A to 27C include a light-emitting element 908 (a first electrode 101, an EL layer 102, and a second electrode 108) over a first substrate 901. The light-emitting element 908 can be formed using any of the materials described in Embodiment 2. The EL layer 102 includes any of the composition materials of embodiments of the present invention.

To the light-emitting devices of this embodiment, any of the following structures can be applied: a structure in which a light-emitting element emits light upward (such a structure is also referred to as top emission structure); a structure in which a light-emitting element emits light upward and downward (such a structure is also referred to as dual emission structure); and a structure in which a light-emitting element emits light downward (such a structure is also referred to as bottom emission structure).

A light-emitting device having a bottom emission structure is illustrated in FIG. 27B.

The light-emitting device illustrated in FIG. 27B has the first electrode 101 over the first substrate 901, the EL layer 102 over the first electrode 101, and the second electrode 108 over the EL layer 102.

A first terminal 903 is electrically connected to an auxiliary wiring 910 and the first electrode 101, and a second terminal 904 is electrically connected to the second electrode 108. Further, an insulating layer 909 is formed between end portions of the first electrode 101 and the second electrode 108 and between the auxiliary wiring 910 and the EL layer 102. Note that although a structure in which the first electrode 101 is formed over the auxiliary wiring 910 is illustrated in FIG. 27B, a structure in which the auxiliary wiring 910 is formed over the first electrode 101 may be possible.

In addition, the first substrate 901 and the second substrate 902 are bonded together by a sealing material 912. Further, a desiccant 911 may be included between the first substrate 901 and the second substrate 902.

Further, the upper and/or lower portions of the first substrate 901 may be provided with a light extraction structure. As the light extraction structure, an uneven structure can be provided at an interface through which light is transmitted from the side having a high refractive index to the side having a low refractive index. A specific example is as follows: as illustrated in FIG. 27B, a light extraction structure 913a with minute unevenness is provided between the light-emitting element 908 having a high refractive index and the first substrate 901 having a lower refractive index, and a light extraction structure 913b with unevenness is provided between the first substrate 901 and the air.

However, in the light-emitting element, unevenness of the first electrode 101 might cause leakage current generation in the EL layer 102 formed over the first electrode 101. Therefore, in this embodiment, a planarization layer 914 having a refractive index higher than or equal to that of the EL layer 102 is provided in contact with the light extraction structure 913a. Accordingly, the first electrode 101 can be a flat film, and the leakage current generation in the EL layer due to the unevenness of the first electrode 101 can be suppressed. Further, because of the light extraction structure 913a at an interface between the planarization layer 914 and the first substrate 901, light which cannot be extracted to the air due to total reflection can be reduced, so that the light extraction efficiency of the light-emitting device can be increased.

The present invention is not limited to the structure in which the first substrate 901, the light extraction structure 913a, and the light extraction structure 913b are different components as in FIG. 27B. Two or all of these may be formed as one component. The light extraction structure 913a may be all formed inside a sealing region.

A light-emitting device having a top emission structure is illustrated in FIG. 27C.

The light-emitting device illustrated in FIG. 27C has the second electrode 108 over the first substrate 901, the EL layer 102 over the second electrode 108, and the first electrode 101 over the EL layer 102.

The first terminal 903 is electrically connected to the second electrode 108, and the second terminal 904 is electrically connected to the first electrode 101. Further, the insulating layer 909 is formed between end portions of the first electrode 101 and the second electrode 108.

In addition, the first substrate 901 and the second substrate 902 are bonded together by the sealing material 912. Further, an auxiliary wiring may be formed over the first electrode 101. Furthermore, the desiccant 911 may be included between the first substrate 901 and the second substrate 902. The desiccant 911 is preferably provided at a position that does not overlap a light-emitting region of a light-emitting element. Alternatively, a desiccant that transmits light from the light-emitting element is preferably used.

Although the light-emitting device 900 illustrated in FIG. 27A is octagonal, the present invention is not limited to this shape. The light-emitting device 900 and the light-emitting element 908 may have other polygonal shapes or a shape having a curve. As the shape of the light-emitting device 900, a triangle, a quadrangle, a hexagon, or the like is particularly preferred. The reason for this is that such a shape allows a plurality of light-emitting devices 900 to be provided in a limited area without a space therebetween, and also because such a shape enables effective use of the limited substrate area for formation of the light-emitting device 900. Further, the number of elements formed over the substrate is not limited to one and a plurality of elements may be provided.

As materials of the first substrate 901 and the second substrate 902, a material having a light-transmitting property, such as glass, quartz, or an organic resin can be used. At least one of the first substrate 901 and the second substrate 902 transmits light emitted from the light-emitting element.

In the case where an organic resin is used for the substrates, for example, any of the following can be used as the organic resin: polyester resins such as polyethylene terephthalate (PET) and polyethylene naphthalate (PEN), a polyacrylonitrile resin, a polyimide resin, a polymethylmethacrylate resin, a polycarbonate (PC) resin, a polyethersulfone (PES) resin, a polyamide resin, a cycloolefin resin, a polystyrene resin, a polyamide imide resin, a polyvinylchloride resin, and the like. A substrate in which a glass fiber is impregnated with an organic resin or a substrate in which an inorganic filler is mixed with an organic resin can also be used.

The light-emitting devices described in this embodiment (the active matrix light-emitting device and the passive matrix light-emitting device) are both formed using a light-emitting element of one embodiment of the present invention, and accordingly, the light-emitting devices have low power consumption.

Note that this embodiment can be implemented in appropriate combination with any of the other embodiments.

Embodiment 4

In this embodiment, with reference to FIGS. 5A to 5E and FIG. 6, description is given of examples of a variety of electronic devices and lighting devices that are each completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like. Specific examples of these electronic devices and a lighting device are illustrated in FIGS. 5A to 5E.

Figure 5A:
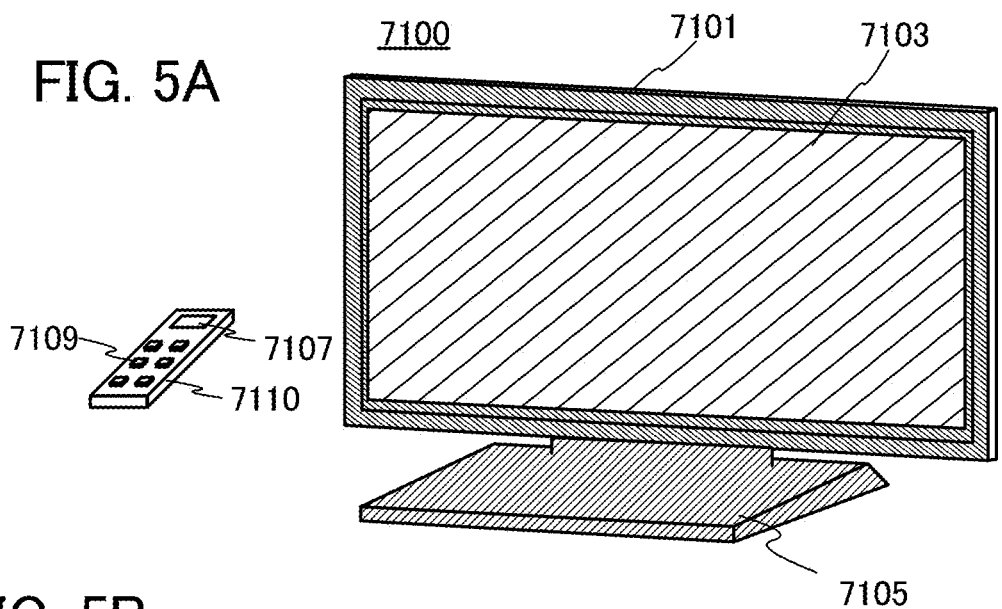
FIGS. 5A to 5E each illustrate an electronic device of one embodiment of the present invention.

FIG. 5A illustrates an example of a television device. In the television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
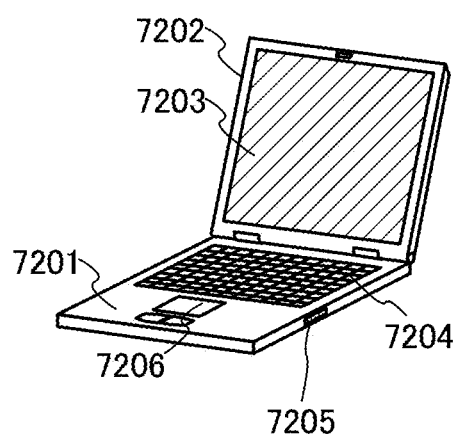

FIG. 5B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 5C:
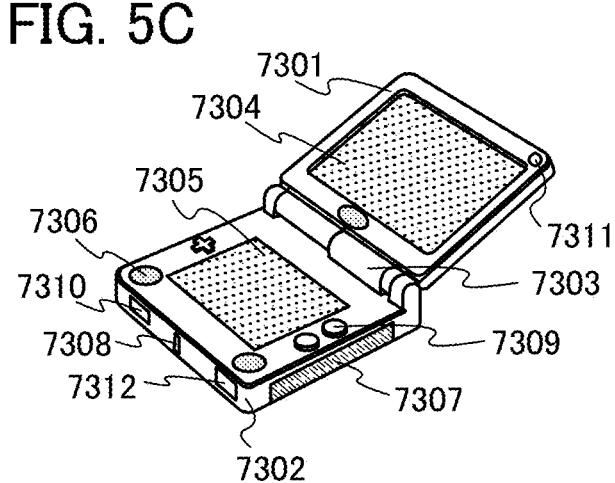

FIG. 5C illustrates a portable game machine, which includes two housings, a housing 7301 and a housing 7302, connected with a joint portion 7303 so that the portable game machine can be opened or closed. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
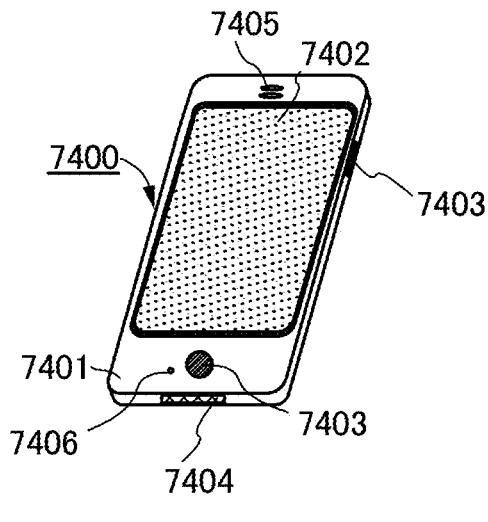

FIG. 5D illustrates an example of a cellular phone. The cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 5D is touched with a finger or the like, data can be input to the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image to be displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, so that personal identification can be performed. Furthermore, by provision of a backlight or a sensing light source emitting near-infrared light for the display portion, an image of a finger vein, a palm vein, or the like can also be taken.

Figure 5E:
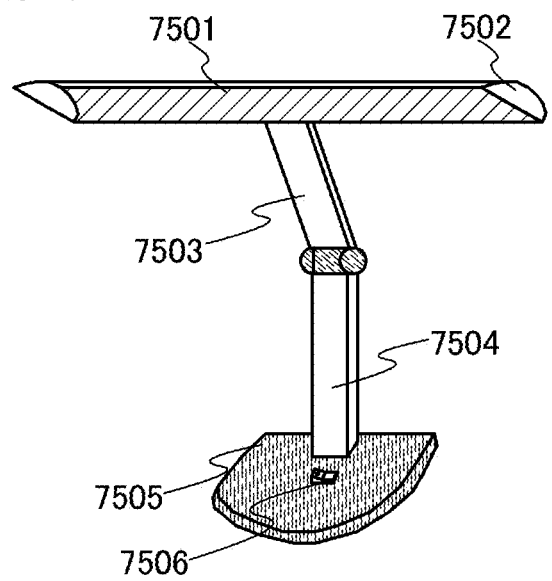

FIG. 5E illustrates a desk lamp, which includes a lighting portion 7501, a shade 7502, an adjustable arm 7503, a support 7504, a base 7505, and a power switch 7506. The desk lamp is manufactured using a light-emitting device for the lighting portion 7501. Note that the "lighting device" also includes ceiling lights, wall lights, and the like.

Figure 6:
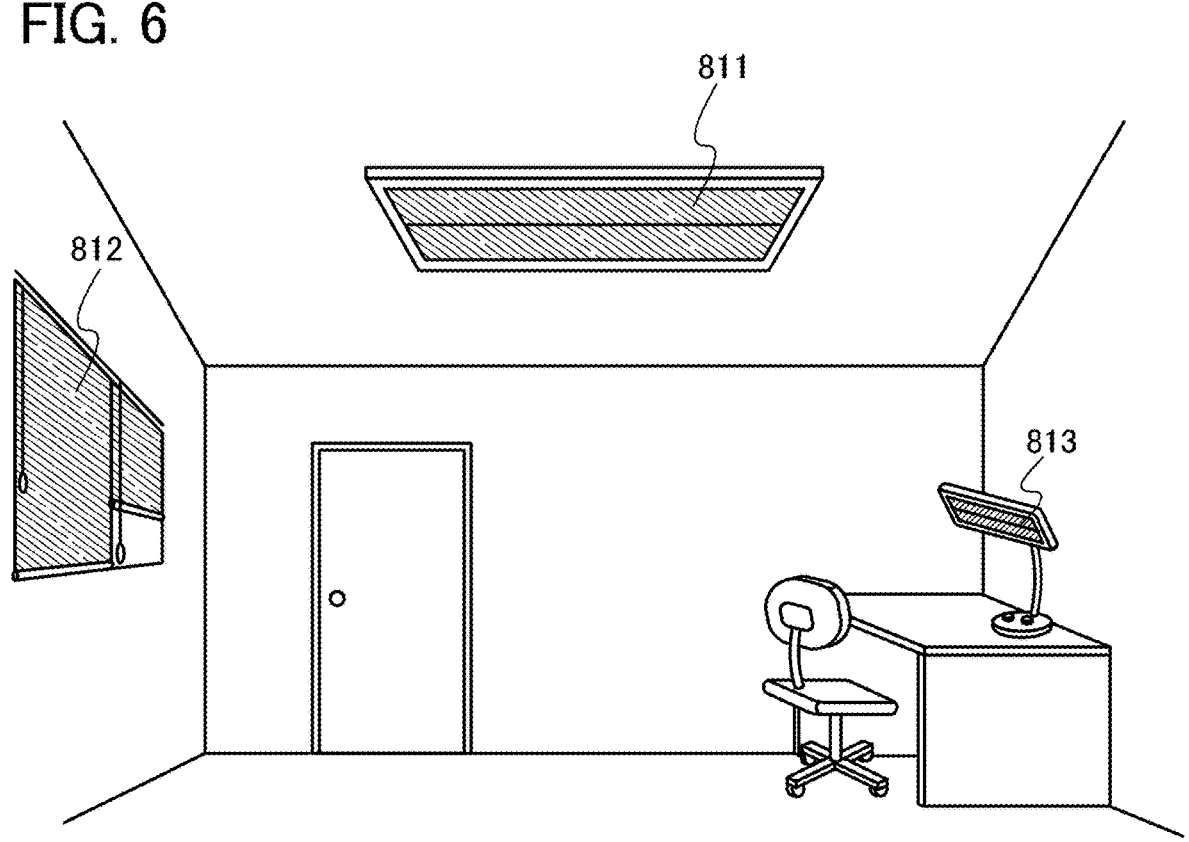
FIG. 6 illustrates a lighting device of one embodiment of the present invention.

FIG. 6 illustrates an example in which a light-emitting device is used for an interior lighting device 811. Since the light-emitting device can have a larger area, it can be used as a lighting device having a large area. Furthermore, the light-emitting device can be used as a roll-type lighting device 812. As illustrated in FIG. 6, a desk lamp 813 described with reference to FIG. 5E may also be used in a room provided with the interior lighting device 811.

In the above-described manner, electronic devices or lighting devices can be obtained by application of a light-emitting device. Application range of the light-emitting device is so wide that the light-emitting device can be applied to electronic devices in a variety of fields.

Note that the structure described in this embodiment can be combined with the structure described in any of the above embodiments as appropriate.

Example 1

In this example, composite materials of one embodiment of the present invention are specifically exemplified. The composite materials of one embodiment of the present invention each include a hydrocarbon compound which has a substituent bonded to a naphthalene skeleton, a phenanthrene skeleton, or a triphenylene skeleton and which has a molecular weight greater than or equal to 350 and less than or equal to 2000 and an inorganic compound exhibiting an electron-accepting property with respect to the hydrocarbon compound, in which the substituent has one or more rings selected from a benzene ring, a naphthalene ring, a phenanthrene ring, and a triphenylene ring.

Table 1 shows the hydrocarbon compounds used in Composition Examples 1 to 3 and Comparison Example in this example and the HOMO levels (eV) of the hydrocarbon compounds. Note that the HOMO levels are measured by photoelectron spectroscopy. In addition, structural formulae of the hydrocarbon compounds are illustrated below.

TABLE 1

|  | Hydrocarbon compound | HOMO level (eV) |
| --- | --- | --- |
| Composition Example 1 | N3P | −5.8 |
| Composition Example 2 | Pn3P | −5.9 |

TABLE 1-continued

| | Hydrocarbon compound | HOMO level (eV) |
|---|---|---|
| Composition Example 3 | P4N | −6.0 |
| Comparison Example | DPAnth | −5.7 |

[Chemical Formula 24]

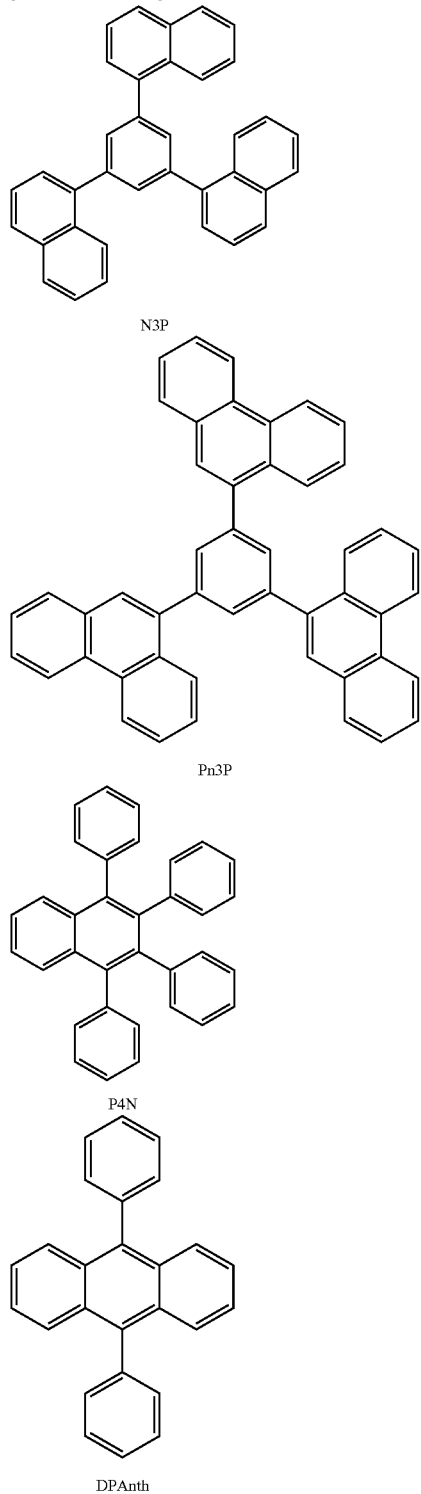

N3P

Pn3P

P4N

DPAnth

Figure 32A:
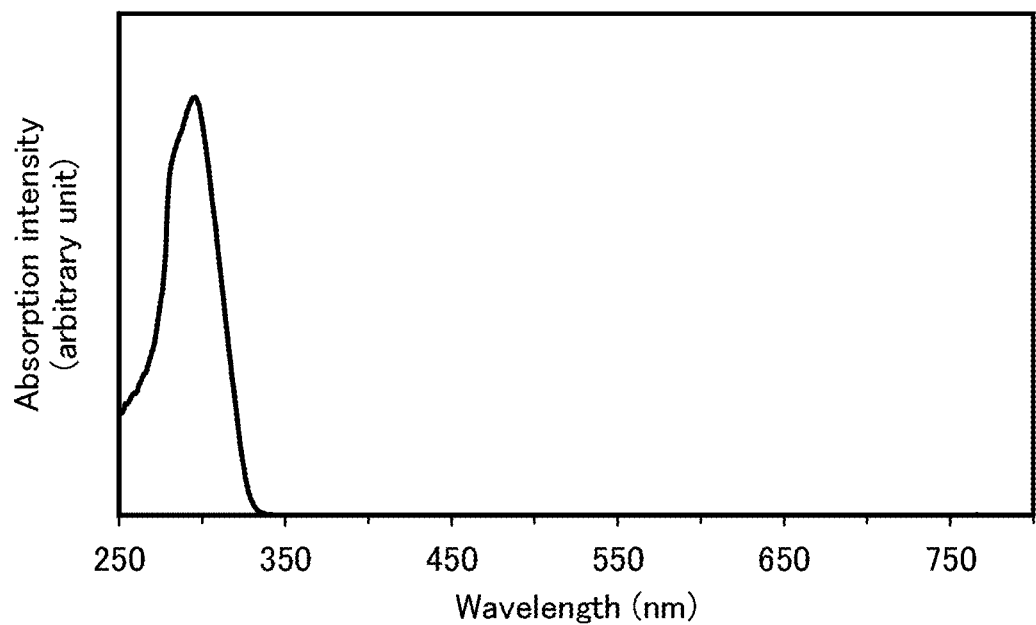
FIGS. 32A and 32B show an absorption and emission spectra of N3P in a toluene solution of N3P.
Figure 32B:
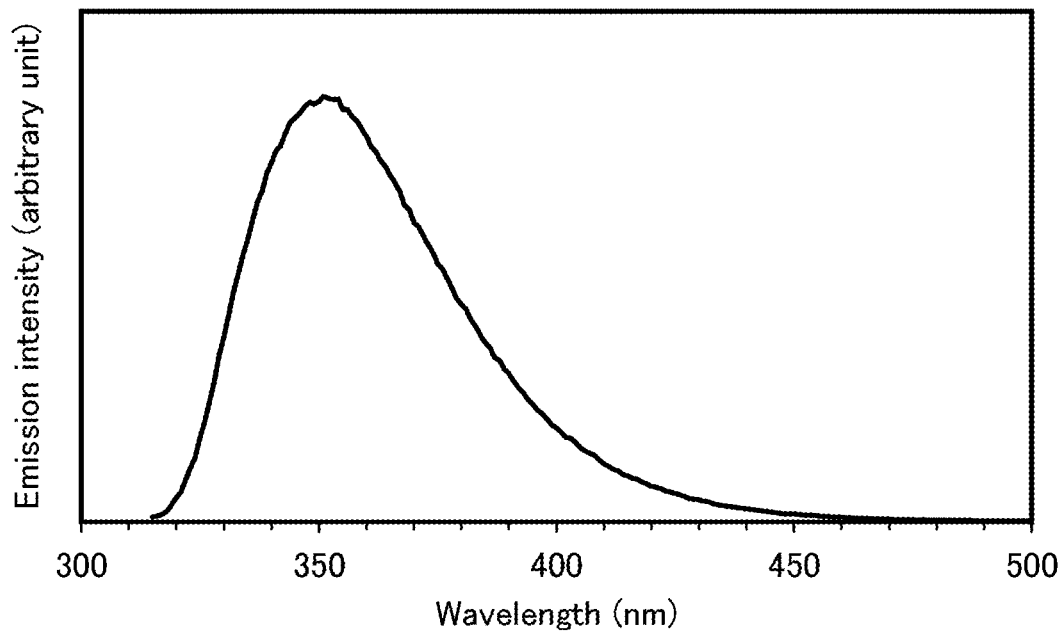
Figure 33A:
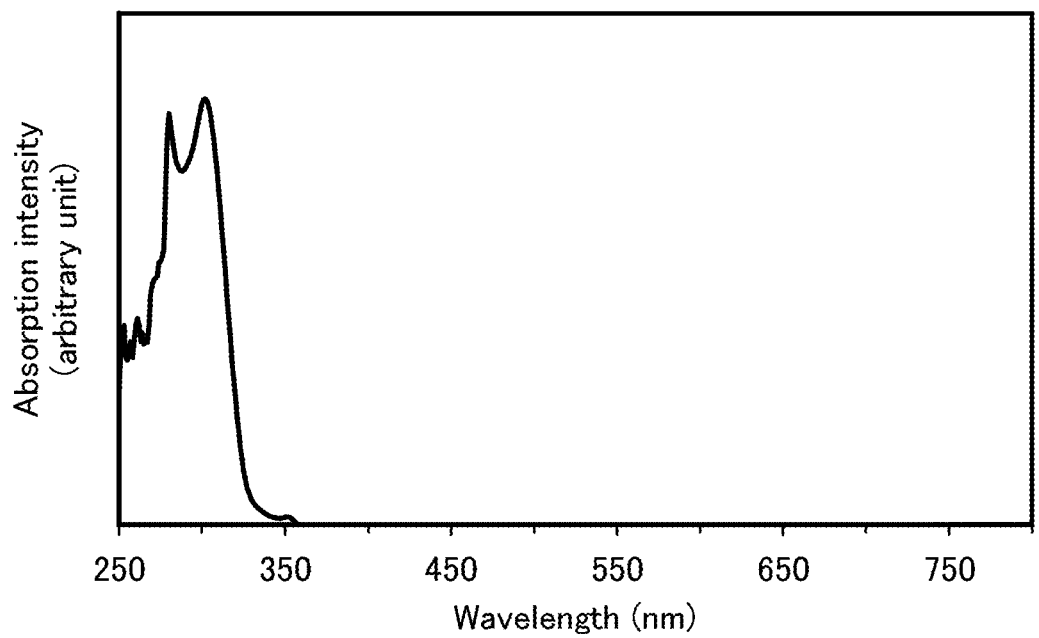
FIGS. 33A and 33B show an absorption and emission spectra of Pn3P in a toluene solution of Pn3P.
Figure 33B:
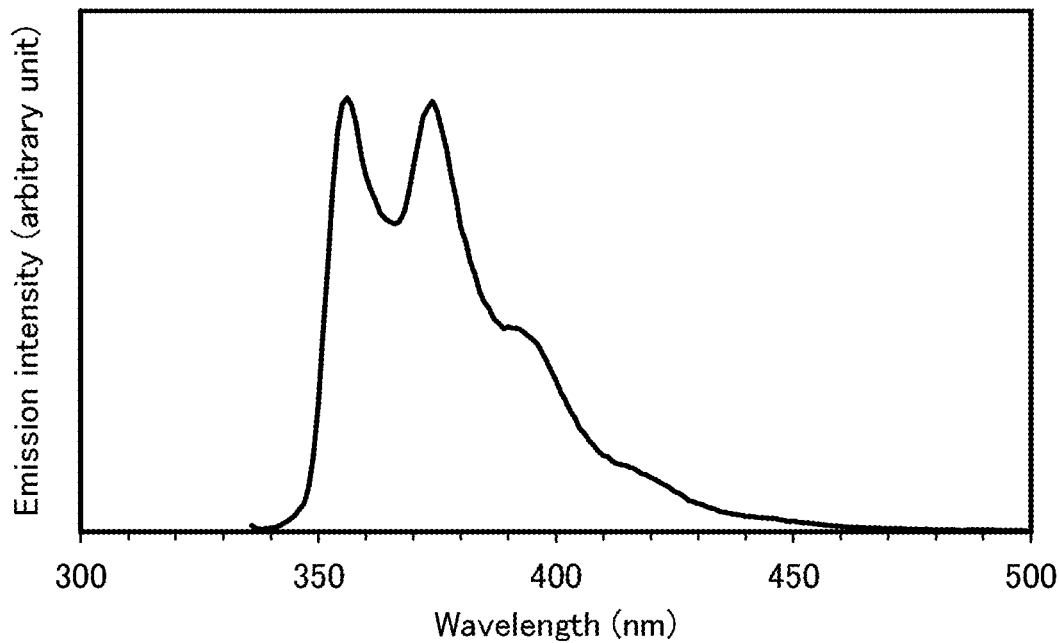

Further, FIG. 32A shows an absorption spectrum of N3P in a toluene solution of N3P, and FIG. 32B shows an emission spectrum thereof. Furthermore, FIG. 33A shows an absorption spectrum of Pn3P in a toluene solution of Pn3P, and FIG. 33B shows an emission spectrum thereof. The absorption spectrum was measured using an ultraviolet-visible spectrophotometer (V-550, produced by JASCO Corporation). The measurements were performed in such a way that each solution was put in a quartz cell. Here is shown the absorption spectrum which was obtained by subtraction of the absorption spectra of quartz and toluene from those of quartz and the solution. In each of FIG. 32A and FIG. 33A, the horizontal axis represents wavelength (nm) and the vertical axis represents absorption intensity (arbitrary unit). In each of FIG. 32B and FIG. 33B, the horizontal axis represents wavelength (nm) and the vertical axis represents emission intensity (arbitrary unit). While N3P exhibits an absorption peak at around 295 nm and an emission wavelength peak at 351 nm (at an excitation wavelength of 300 nm), Pn3P exhibits an absorption peak at around 302 nm and an emission wavelength peak at 356 nm and 374 nm (at an excitation wavelength of 303 nm).

It is thus found from the absorption spectra of the hydrocarbon compounds in the toluene solutions, each of which is used for the composite material of one embodiment of the present invention, that absorption in the visible light region is hardly observed. In addition, since the emission peaks are located at the shorter wavelengths, the hydrocarbon compounds are each found suitable for a material of the hole-transport layer in contact with a light-emitting layer and for a host material of a light-emitting layer.

The thin films of the hydrocarbon compounds, each of which is used for the composite material of one embodiment of the present invention, also exhibit almost no absorption spectrum in the visible light region, as described later (see FIGS. 7A and 7B, FIGS. 8A and 8B, FIGS. 9A and 9B, and FIGS. 10A and 10B). The fact that both the solution and the thin film exhibit almost no absorption in the visible light region indicates each hydrocarbon compound is suitable for both a film of a single substance and for a film of a mixture with another organic compound. Thus, the hydrocarbon compounds can each be suitably used for any of the composite material of one embodiment of the present invention, a hole-transport layer, and a light-emitting layer.

Further, thermophysical properties were measured with a differential scanning calorimeter (DSC) (Pyris 1 DSC, manufactured by PerkinElmer, Inc.). The glass transition temperature of Pn3P was found to be 202° C. Thus, Pn3P is found to have good thermophysical properties. Therefore, the composite material of one embodiment of the present invention in which this material is used is found to have good thermophysical properties.

In each of Composition Examples 1 to 3 and Comparison Example, molybdenum oxide was used as the inorganic compound.

The way how the composite materials of embodiments of the present invention were prepared are described.

Composition Example 1

First, a glass substrate was fixed to a substrate holder inside a vacuum evaporation apparatus. Then, 1-[3,5-di(naphthalen-1-yl)phenyl]naphthalene (abbreviation: N3P) and molybdenum(VI) oxide were separately put in respective resistance-heating evaporation sources, and under reduced pressure, films containing N3P and molybdenum oxide were formed by a co-evaporation method. At this time, N3P and molybdenum(VI) oxide were co-evaporated such that the mass ratios of N3P to molybdenum oxide were 4:2, 4:1, and 4:0.5 (=N3P:molybdenum oxide). Further, the thickness of each film was set to 50 nm.

Figure 7A:
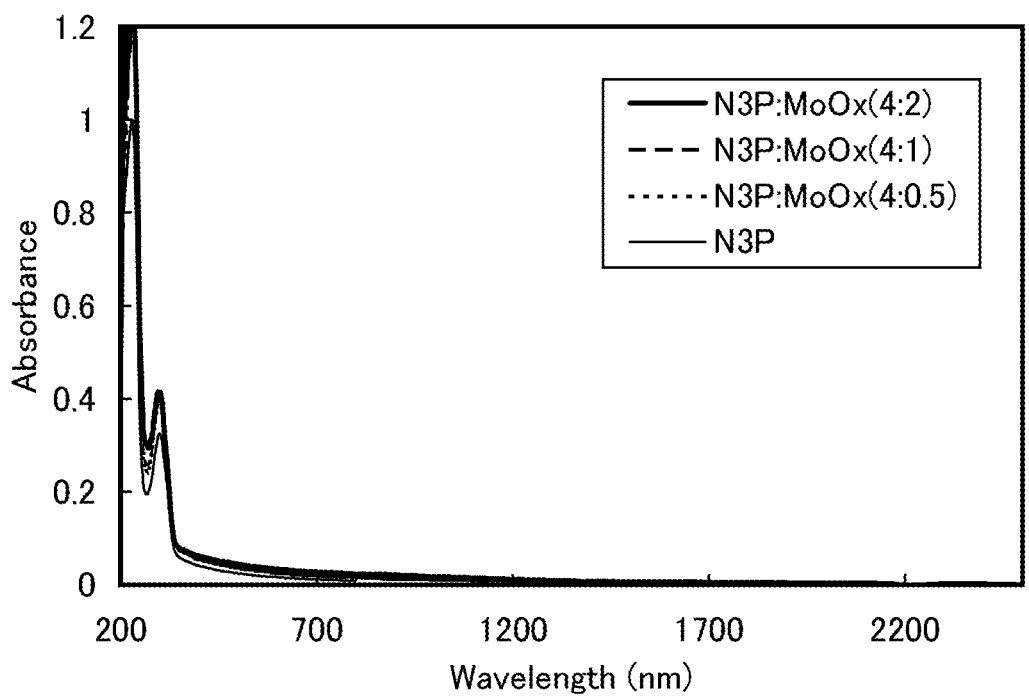
FIGS. 7A and 7B show absorbances of N3P and a composite material thereof according to Example 1.
Figure 7B:
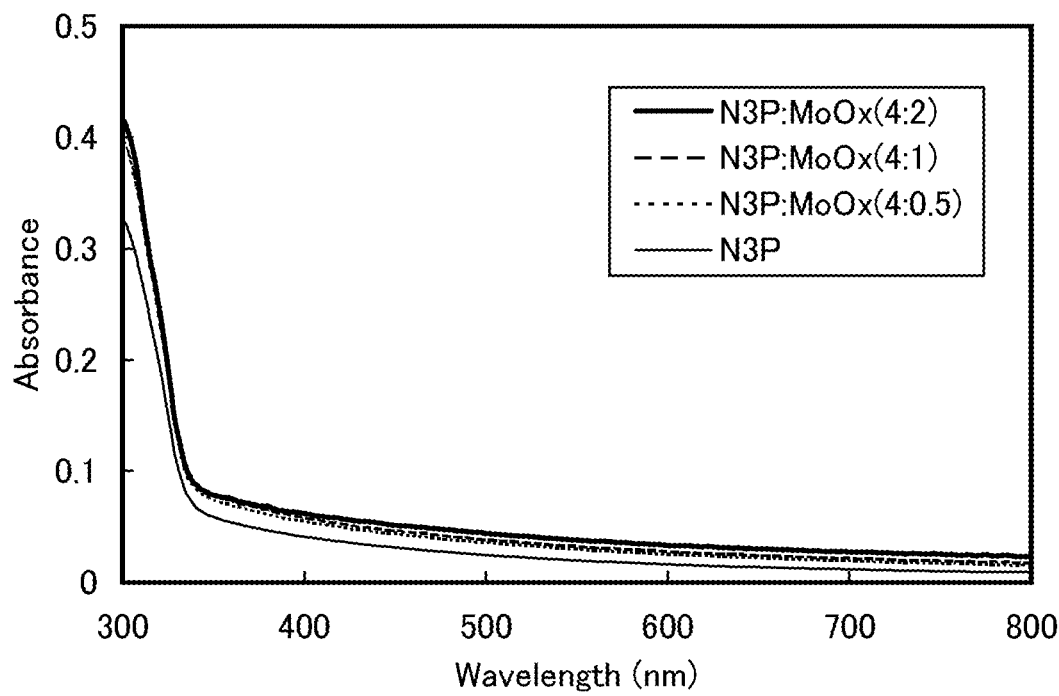

FIGS. 7A and 7B show measurement results of absorption spectra of the thus formed composite films of N3P and molybdenum oxide (Composition Example 1). In addition, for comparison, an absorption spectrum of a film of only N3P (50 nm thick) is also shown in the drawings.

Composition Example 2

First, a glass substrate was fixed to a substrate holder inside a vacuum evaporation apparatus. Then, 9-[3,5-di(phenanthren-9-yl)phenyl]phenanthrene (abbreviation: Pn3P) and molybdenum(VI) oxide were separately put in respective resistance-heating evaporation sources, and under reduced pressure, films containing Pn3P and molybdenum oxide were formed by a co-evaporation method. At this time, Pn3P and molybdenum(VI) oxide were co-evaporated such that the mass ratios of Pn3P to molybdenum oxide were 4:2, 4:1, and 4:0.5 (=Pn3P:molybdenum oxide). Further, the thickness of each film was set to 50 nm.

Figure 8A:
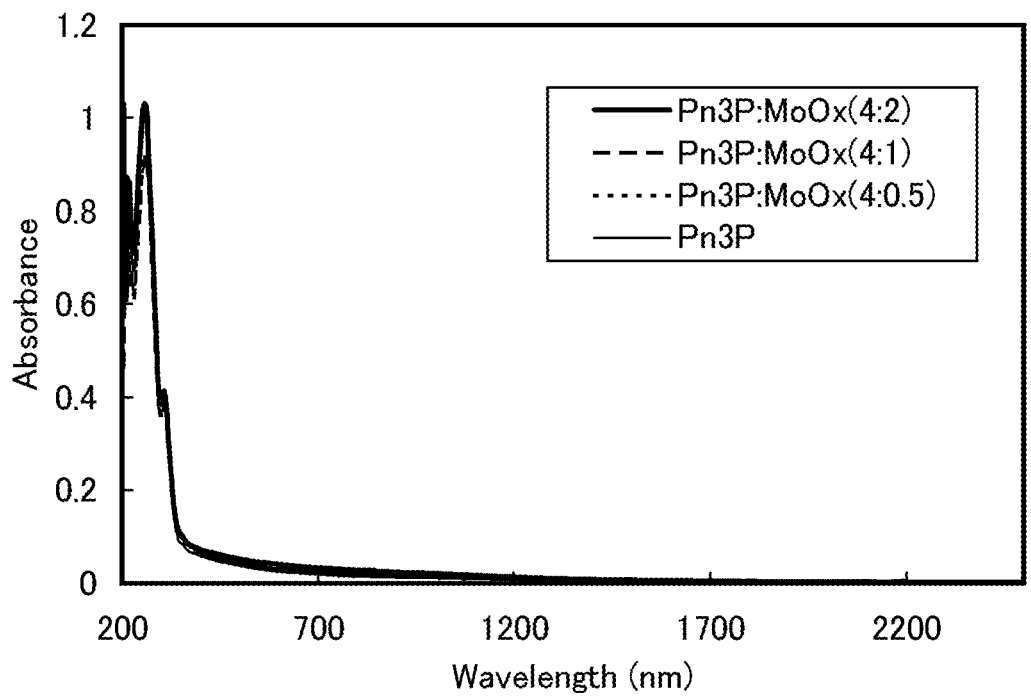
FIGS. 8A and 8B show absorbances of Pn3P and a composite material thereof according to Example 1.
Figure 8B:
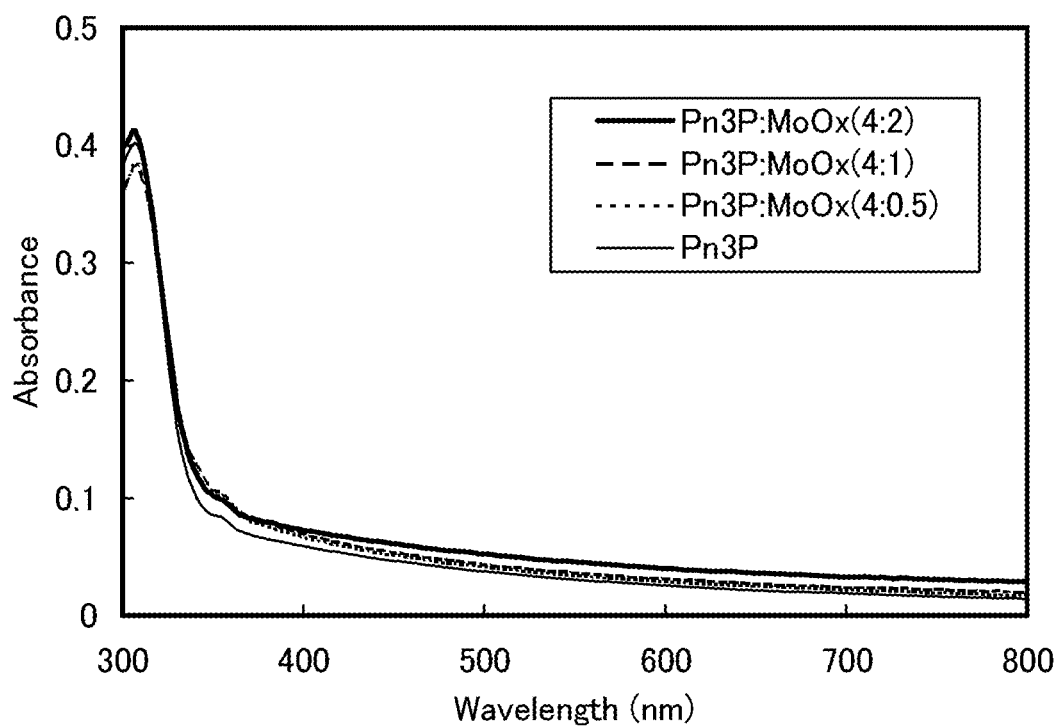

FIGS. 8A and 8B show measurement results of absorption spectra of the thus formed composite films of Pn3P and molybdenum oxide (Composition Example 2). In addition, for comparison, an absorption spectrum of a film of only Pn3P (50 nm thick) is also shown in the drawings.

Composition Example 3

First, a glass substrate was fixed to a substrate holder inside a vacuum evaporation apparatus. Then, 1,2,3,4-tetraphenylnaphthalene (abbreviation: P4N) and molybdenum(VI) oxide were separately put in respective resistance-heating evaporation sources, and under reduced pressure, films containing P4N and molybdenum oxide were formed by a co-evaporation method. At this time, P4N and molybdenum(VI) oxide were co-evaporated such that the mass ratios of P4N to molybdenum oxide were 4:4, 4:2, and 4:0.5 (=P4N:molybdenum oxide). Further, the thickness of each film was set to 50 nm.

Figure 9A:
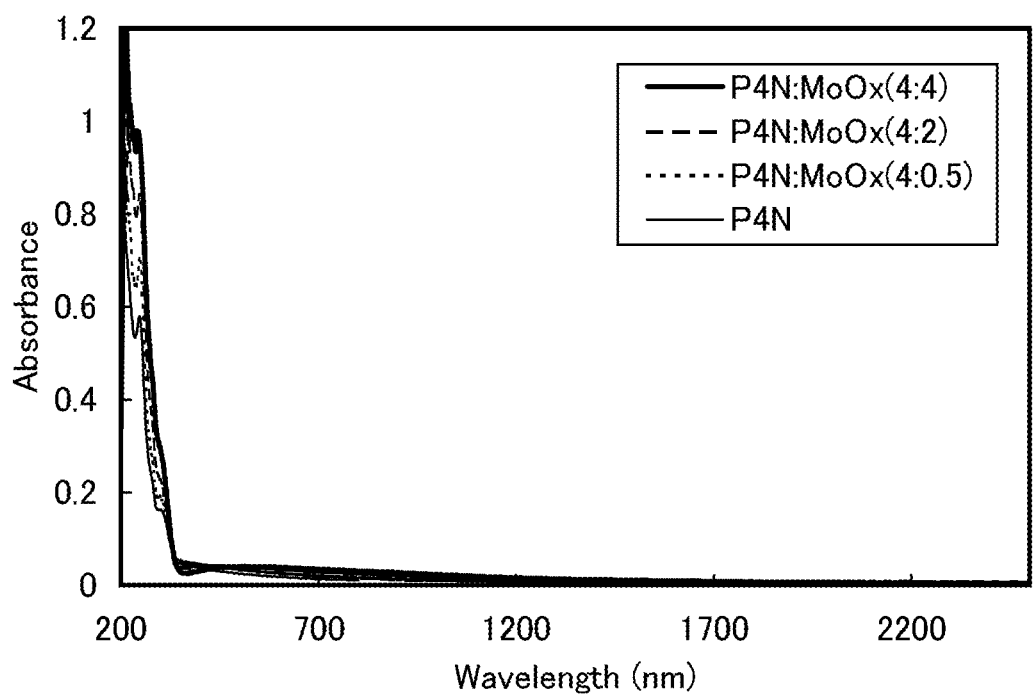
FIGS. 9A and 9B show absorbances of P4N and a composite material thereof according to Example 1.
Figure 9B:
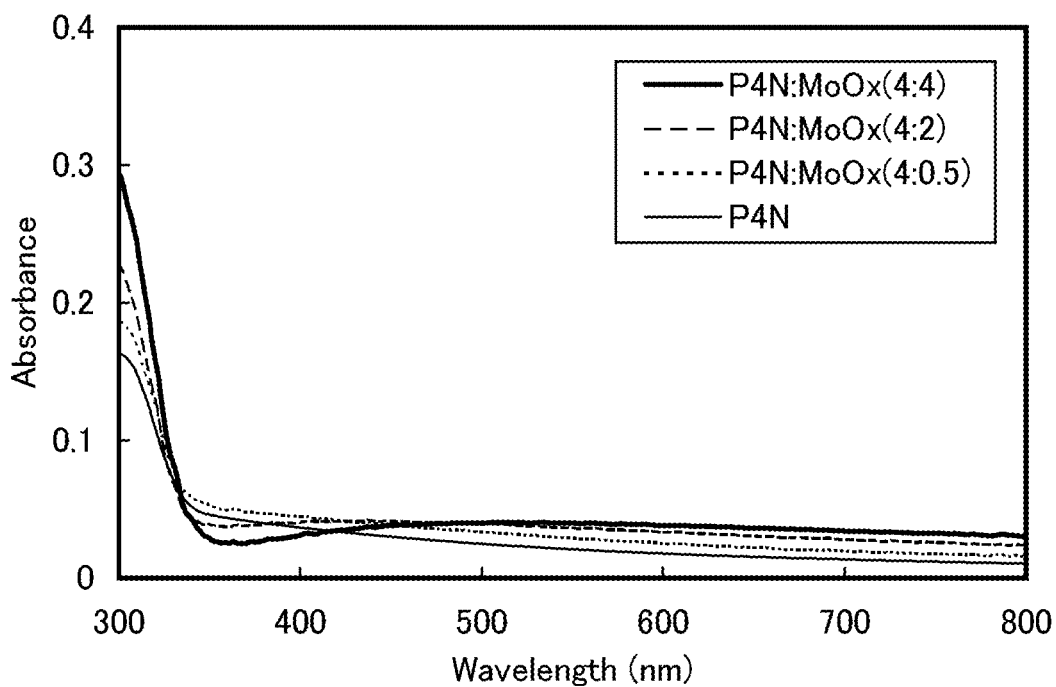

FIGS. 9A and 9B show measurement results of absorption spectra of the thus formed composite films of P4N and molybdenum oxide (Composition Example 3). In addition, for comparison, an absorption spectrum of a film of only P4N (50 nm thick) is also shown in the drawings.

COMPARISON EXAMPLE

First, a glass substrate was fixed to a substrate holder inside a vacuum evaporation apparatus. Then, 9,10-diphenylanthracene (abbreviation: DPAnth) and molybdenum(VI) oxide were separately put in respective resistance-heating evaporation sources, and under reduced pressure, films containing DPAnth and molybdenum oxide were formed by a co-evaporation method. At this time, DPAnth and molybdenum(VI) oxide were co-evaporated such that the mass ratios of DPAnth to molybdenum oxide were 4:2, 4:1, and 4:0.5 (=DPAnth:molybdenum oxide). Further, the thickness of each film was set to 50 nm.

Figure 10A:
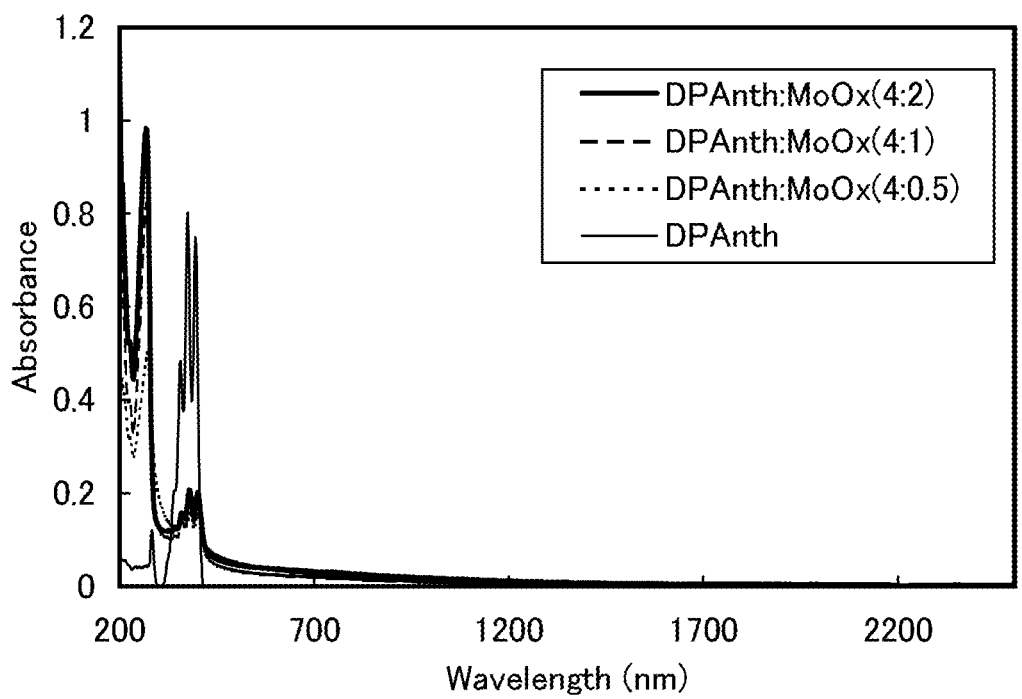
FIGS. 10A and 10B show absorbances of DPAnth and a composite material thereof according to Example 1.
Figure 10B:
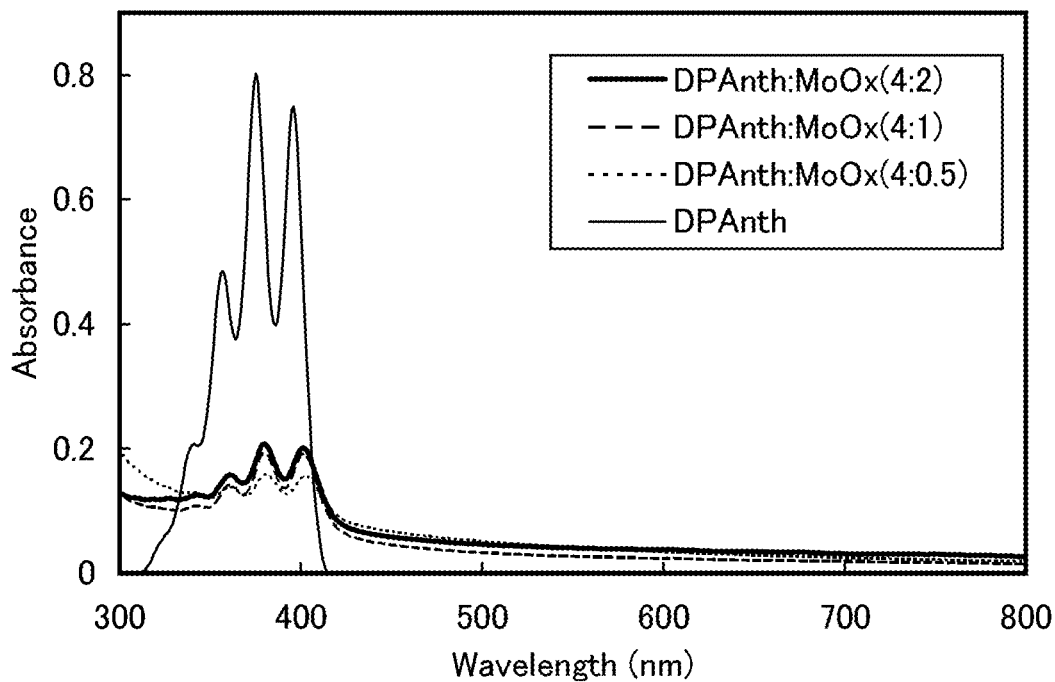

FIGS. 10A and 10B show measurement results of absorption spectra of the thus formed composite films of DPAnth and molybdenum oxide (Comparison Example). In addition, for comparison, an absorption spectrum of a film of only DPAnth (50 nm thick) is also shown in the drawings.

In each of FIGS. 7A and 7B, FIGS. 8A and 8B, FIGS. 9A and 9B, and FIGS. 10A and 10B, the horizontal axis represents wavelength (nm) and the vertical axis represents absorbance (no unit).

The composite film of DPAnth and molybdenum oxide (DPAnth:molybdenum oxide=4:0.5), which is described in Comparison Example, was crystallized.

The hydrocarbon compound used in Comparison Example (FIGS. 10A and 10B) has an anthracene skeleton. In a thick film in which the hydrocarbon compound including an anthracene skeleton is used for a composite material, slight absorption peaks in the visible light region, which originate from the anthracene skeleton, are observed. On the other hand, each of the composite materials described in Composition Examples 1 to 3 (FIGS. 7A and 7B, FIGS. 8A and 8B, and FIGS. 9A and 9B) does not exhibit a significant absorption peak in the wavelength region of at least 360 nm or more; thus, the composite materials are found to have a high light-transmitting property.

It is found that the composite materials of embodiments of the present invention are materials that have almost no significant absorption peak in the visible light region and have a high light-transmitting property. Further, the composite materials of embodiments of the present invention exhibited almost no significant absorption peak also in the infrared region (the wavelength region of 700 nm or more).

The absorption spectra of the composite materials each including the hydrocarbon compound and molybdenum oxide of one embodiment of the present invention have substantially the same shape as the absorption spectrum of the hydrocarbon compound. Almost no significant absorption peak in the visible to infrared region is observed even in the case of films having a high concentration of molybdenum oxide (specifically, the films in which the mass ratios of the hydrocarbon compound to molybdenum oxide are 4:2 and 4:4 in Composition Examples). This indicates that in the composite materials of embodiments of the present invention, light absorption due to charge-transfer interaction is unlikely to occur.

Example 2

Figure 26A:
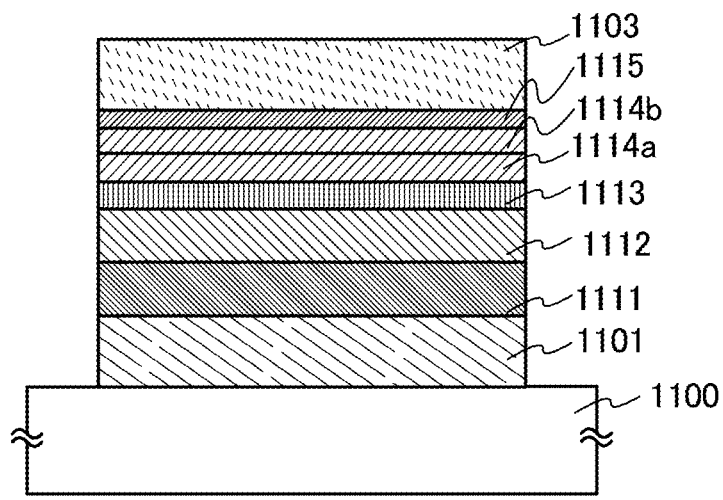
FIGS. 26A and 26B each illustrate a light-emitting element in Examples.

In this example, a light-emitting element of one embodiment of the present invention is described with reference to FIG. 26A. Note that structural formulae of the materials used in the above example are omitted here.

[Chemical Formula 25]

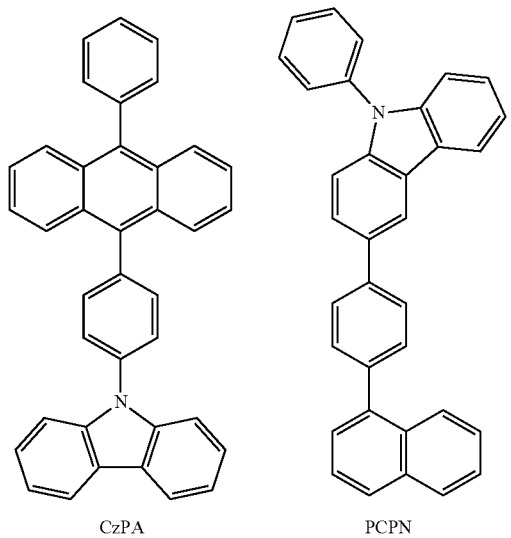

CzPA　　　　　　　　PCPN

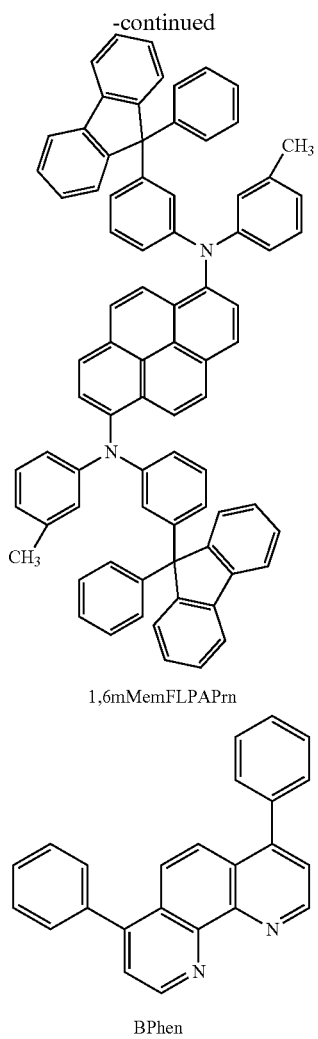

1,6mMemFLPAPrn

BPhen

The way how a light-emitting element 1 of this example was fabricated is described below.

(Light-Emitting Element 1)

First, a film of indium tin oxide containing silicon oxide (ITSO) was formed over a glass substrate 1100 by a sputtering method, so that a first electrode 1101 which functions as an anode was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface over which the first electrode 1101 was provided faced downward. The pressure in the vacuum evaporation apparatus was reduced to about $10^{-4}$ Pa. Then, N3P and molybdenum(VI) oxide were co-evaporated to form a hole-injection layer 1111 over the first electrode 1101. The thickness of the hole-injection layer 1111 was set to 50 nm, and the mass ratio of N3P to molybdenum oxide was adjusted to 4:2 (=N3P:molybdenum oxide). Note that the co-evaporation method refers to an evaporation method in which evaporation is carried out from a plurality of evaporation sources at the same time in one treatment chamber.

Next, over the hole-injection layer 1111, a film of 3-[4-(1-naphthyl)phenyl]-9-phenyl-9H-carbazole (abbreviation: PCPN) was formed to a thickness of 10 nm to form a hole-transport layer 1112.

Furthermore, 9-[4-(N-carbazolyl)]phenyl-10-phenylanthracene (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPm) were co-evaporated to form a light-emitting layer 1113 over the hole-transport layer 1112. Here, the mass ratio of CzPA to 1,6mMemFLPAPm was adjusted to 1:0.04 (=CzPA:1,6mMemFLPAPm). In addition, the thickness of the light-emitting layer 1113 was set to 30 nm.

Further, over the light-emitting layer 1113, a film of CzPA was formed to a thickness of 10 nm to form a first electron-transport layer 1114a.

Then, over the first electron-transport layer 1114a, a film of bathophenanthroline (abbreviation: BPhen) was formed to a thickness of 15 nm to form a second electron-transport layer 1114b.

Further, over the second electron-transport layer 1114b, a film of lithium fluoride (LiF) was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 1 of this example was fabricated.

Note that, in all the above evaporation steps, evaporation was performed by a resistance-heating method.

Table 2 shows element structures of the light-emitting element 1 obtained as described above.

TABLE 2

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | N3P:MoOx (=4:2) 50 nm | PCPN 10 nm | CzPA:1,6mMemFLPAPrn (=1:0.04) 30 nm | CzPA 10 nm | BPhen 15 nm | LiF 1 nm | Al 200 nm |

In a glove box containing a nitrogen atmosphere, the light-emitting element 1 was sealed so as not to be exposed to the air. Then, operation characteristics of the light-emitting element 1 were measured. Note that the measurements were carried out at room temperature (in an atmosphere kept at 25° C.).

Figure 11:
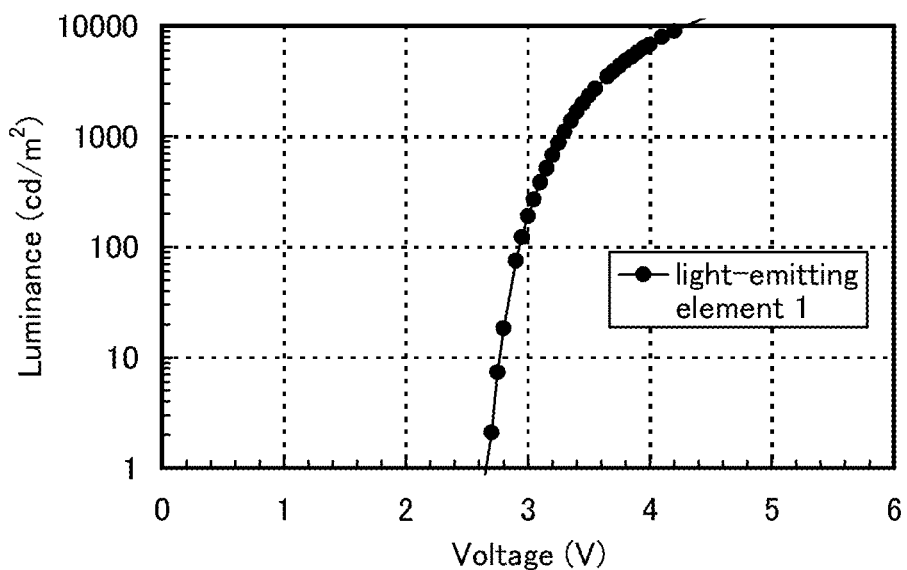
FIG. 11 shows luminance versus voltage characteristics of a light-emitting element of Example 2.
Figure 12:
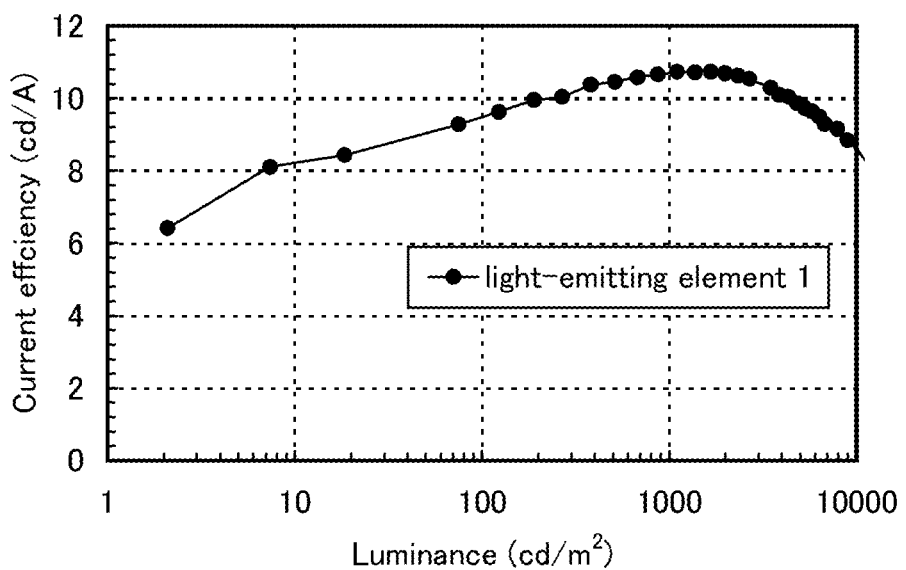
FIG. 12 shows current efficiency versus luminance characteristics of the light-emitting element of Example 2.

The luminance versus voltage characteristics of the light-emitting element 1 are shown in FIG. 11. In FIG. 11, the horizontal axis represents voltage (V) and the vertical axis represents luminance (cd/m$^2$). In addition, the current efficiency versus luminance characteristics of the element are shown in FIG. 12. In FIG. 12, the horizontal axis represents luminance (cd/m$^2$) and the vertical axis represents current efficiency (cd/A). Further, Table 3 shows the voltage (V), CIE chromaticity coordinates (x, y), current efficiency (cd/A), and external quantum efficiency (%) of the light-emitting element 1 at a luminance of 1100 cd/m$^2$.

TABLE 3

| | Voltage (V) | Chromaticity coordinates (x, y) | Current efficiency (cd/A) | External quantum efficiency (%) |
|---|---|---|---|---|
| Light-emitting element 1 | 3.3 | (0.14, 0.18) | 11 | 8.4 |

As shown in Table 3, the CIE chromaticity coordinates of the light-emitting element 1 are (x, y)=(0.14, 0.18) at a luminance of 1100 cd/m$^2$. This result shows that blue light emission originating from 1,6mMemFLPAPrn was obtained from the light-emitting element 1.

As can be seen from FIG. 11 and FIG. 12, the light-emitting element 1 has a low driving voltage and high emission efficiency.

Figure 13:
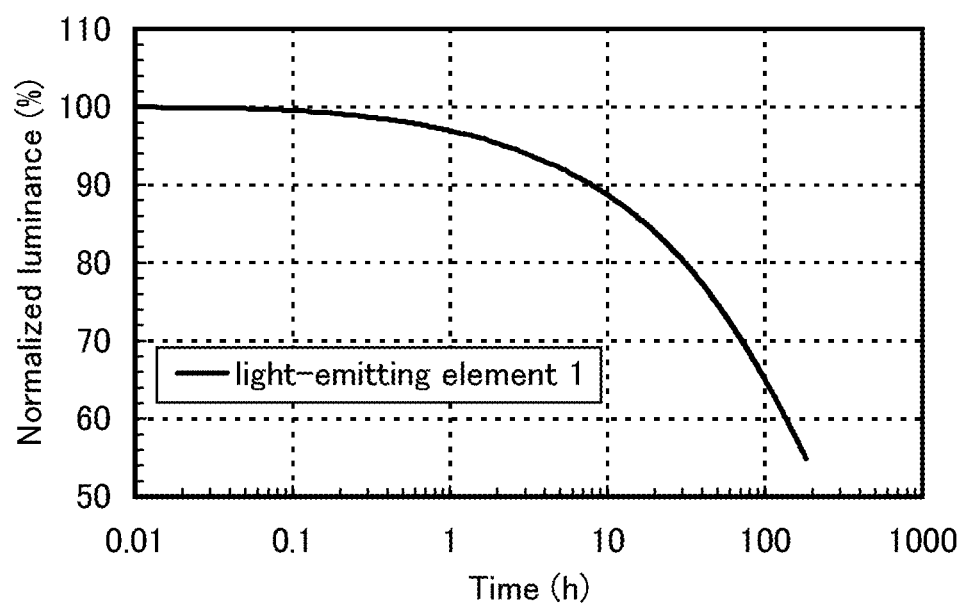
FIG. 13 shows results of a reliability test of the light-emitting element of Example 2.

Next, the light-emitting element 1 was subjected to a reliability test. Results of the reliability test are shown in FIG. 13. In FIG. 13, the vertical axis represents normalized luminance (%) with an initial luminance of 100% and the horizontal axis represents driving time (h) of the element.

In the reliability test, the light-emitting element of this example was driven under the conditions where the initial luminance was set to 5000 cd/m$^2$ and the current density was constant.

FIG. 13 shows that the light-emitting element 1 kept 55% of the initial luminance after 180 hours elapsed. It is found that the light-emitting element 1 to which one embodiment of the present invention is applied has a long lifetime.

The above results suggest that an element having high emission efficiency can be achieved when the composite material of one embodiment of the present invention is used for the hole-injection layer of the light-emitting element. The results also suggest that a light-emitting element having a low driving voltage can be provided when the composite material of one embodiment of the present invention is used for the hole-injection layer of the light-emitting element. The results also suggest that a light-emitting element having a long lifetime can be manufactured when the composite material of one embodiment of the present invention is used for the hole-injection layer.

Example 3

In this example, a light-emitting element of one embodiment of the present invention is described with reference to FIG. 26A. The materials used in this example are the ones used in the above examples, and therefore the chemical formulae thereof are omitted here.

The way how a light-emitting element 2 of this example was fabricated is described below.

(Light-Emitting Element 2) A hole-injection layer 1111 of the light-emitting element 2 was formed by co-evaporating Pn3P and molybdenum(VI) oxide. The thickness of the hole-injection layer 1111 was set to 50 nm, and the mass ratio of Pn3P to molybdenum oxide was adjusted to 4:2 (=Pn3P:molybdenum oxide). Components other than the hole-injection layer 1111 were fabricated in a manner similar to that of the light-emitting element 1.

Table 4 shows element structures of the light-emitting element 2 obtained as described above.

TABLE 4

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 2 | ITSO 110 nm | Pn3P:MoOx (=4:2) 50 nm | PCPN 10 nm | CzPA:1,6mMemFLPAPrn (=1:0.04) 30 nm | CzPA 10 nm | BPhen 15 nm | LiF 1 nm | Al 200 nm |

In a glove box containing a nitrogen atmosphere, the light-emitting element 2 was sealed so as not to be exposed to the air. Then, operation characteristics of the light-emitting element 2 were measured. Note that the measurements were carried out at room temperature (in the atmosphere kept at 25° C.).

Figure 14:
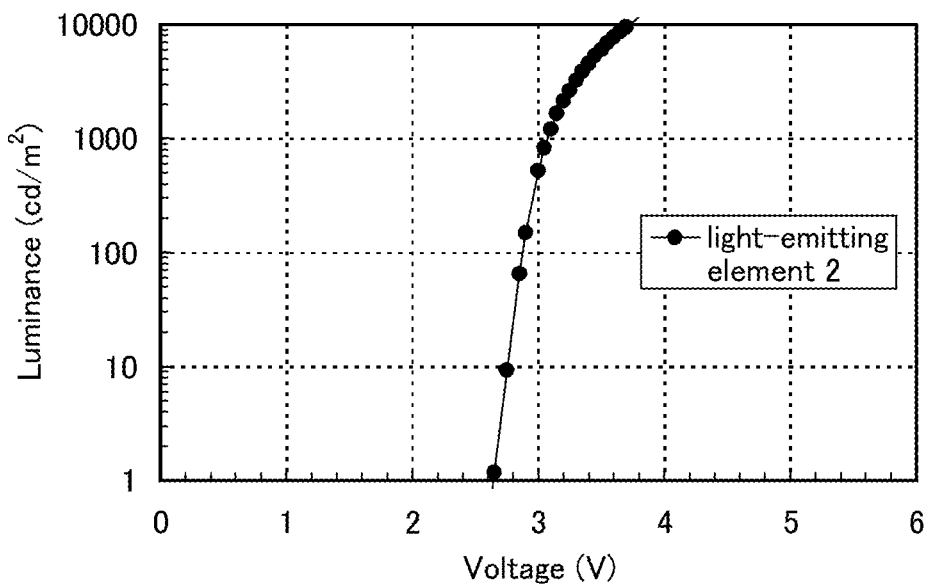
FIG. 14 shows luminance versus voltage characteristics of a light-emitting element of Example 3.
Figure 15:
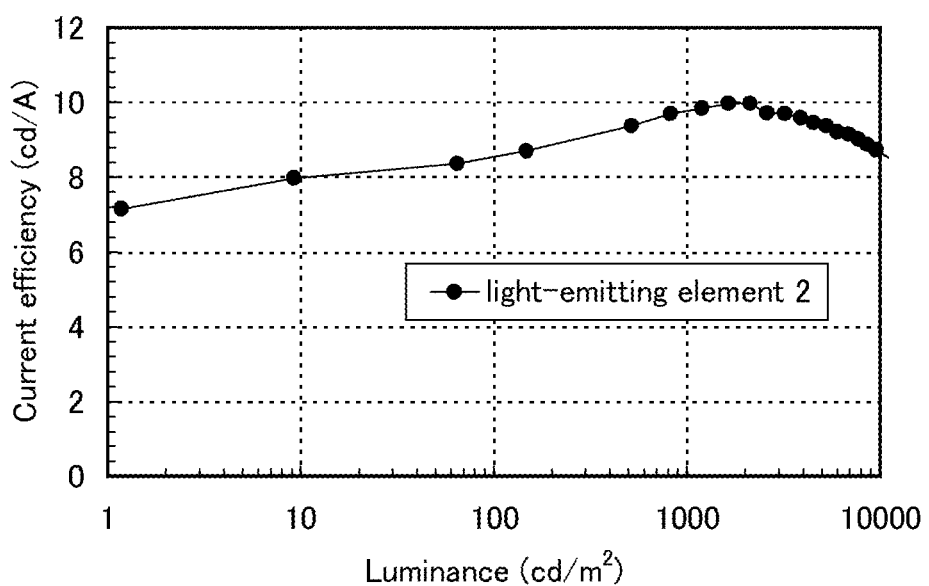
FIG. 15 shows current efficiency versus luminance characteristics of the light-emitting element of Example 3.

The luminance versus voltage characteristics of the light-emitting element 2 are shown in FIG. 14. In FIG. 14, the horizontal axis represents voltage (V) and the vertical axis represents luminance (cd/m$^2$). In addition, the current efficiency versus luminance characteristics of the element are shown in FIG. 15. In FIG. 15, the horizontal axis represents luminance (cd/m$^2$) and the vertical axis represents current efficiency (cd/A). Further, Table 5 shows the voltage (V), CIE chromaticity coordinates (x, y), current efficiency (cd/A), and external quantum efficiency (%) of the light-emitting element 2 at a luminance of 830 cd/m$^2$.

TABLE 5

| | Voltage (V) | Chromaticity coordinates (x, y) | Current efficiency (cd/A) | External quantum efficiency (%) |
|---|---|---|---|---|
| Light-emitting element 2 | 3.1 | (0.14, 0.17) | 9.7 | 7.8 |

As shown in Table 5, the CIE chromaticity coordinates of the light-emitting element 2 are (x, y)=(0.14, 0.17) at a luminance of 830 cd/m². This result shows that blue light emission originating from 1,6mMemFLPAPm was obtained from the light-emitting element 2.

As can be seen from FIG. 14 and FIG. 15, the light-emitting element 2 has a low driving voltage and high emission efficiency.

Figure 16:
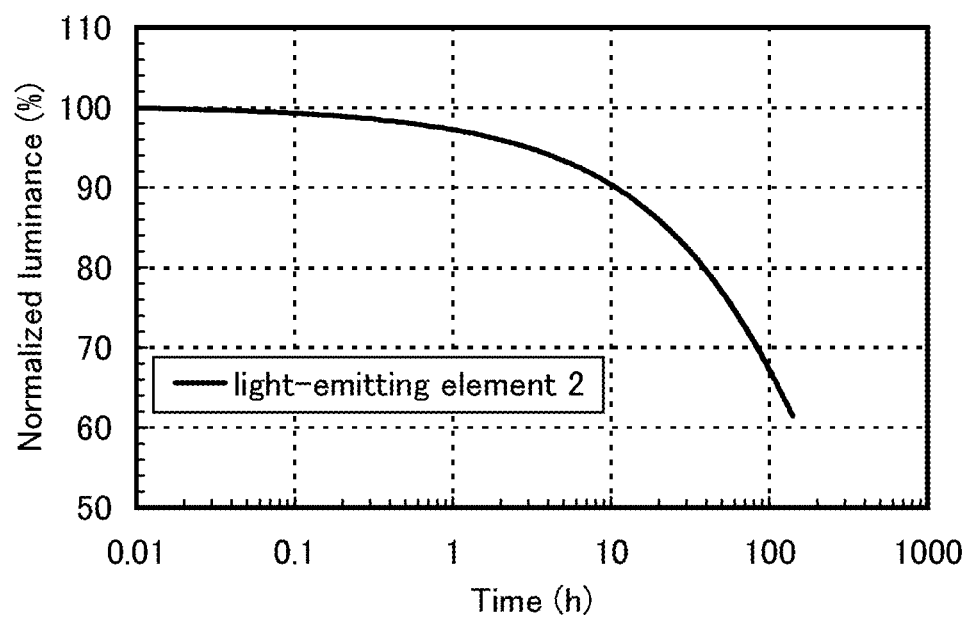
FIG. 16 shows results of a reliability test of the light-emitting element of Example 3.

Next, the light-emitting element 2 was subjected to a reliability test. Results of the reliability test are shown in FIG. 16. In FIG. 16, the vertical axis represents normalized luminance (%) with an initial luminance of 100% and the horizontal axis represents driving time (h) of the element.

In the reliability test, the light-emitting element of this example was driven under the conditions where the initial luminance was set to 5000 cd/m² and the current density was constant.

FIG. 16 shows that the light-emitting element 2 kept 61% of the initial luminance after 140 hours elapsed. It is found that the light-emitting element 2 to which one embodiment of the present invention is applied has a long lifetime.

The above results suggest that an element having high emission efficiency can be achieved when the composite material of one embodiment of the present invention is used for the hole-injection layer of the light-emitting element. The results also suggest that a light-emitting element having a low driving voltage can be provided when the composite material of one embodiment of the present invention is used for the hole-injection layer of the light-emitting element. The results also suggest that a light-emitting element having a long lifetime can be manufactured when the composite material of one embodiment of the present invention is used for the hole-injection layer.

Example 4

In this example, a light-emitting element of one embodiment of the present invention is described with reference to FIG. 26A. The materials used in this example are the ones used in the above examples, and therefore the chemical formulae thereof are omitted here.

The way how a light-emitting element 3 of this example was fabricated is described below.
(Light-Emitting Element 3)

The hole-transport layer 1112 of the light-emitting element 3 was formed by forming a film of N3P to a thickness of 10 nm. Components other than the hole-transport layer 1112 were fabricated in a manner similar to that of the light-emitting element 1.

Table 6 shows element structures of the light-emitting element 3 obtained as described above.

Figure 17:
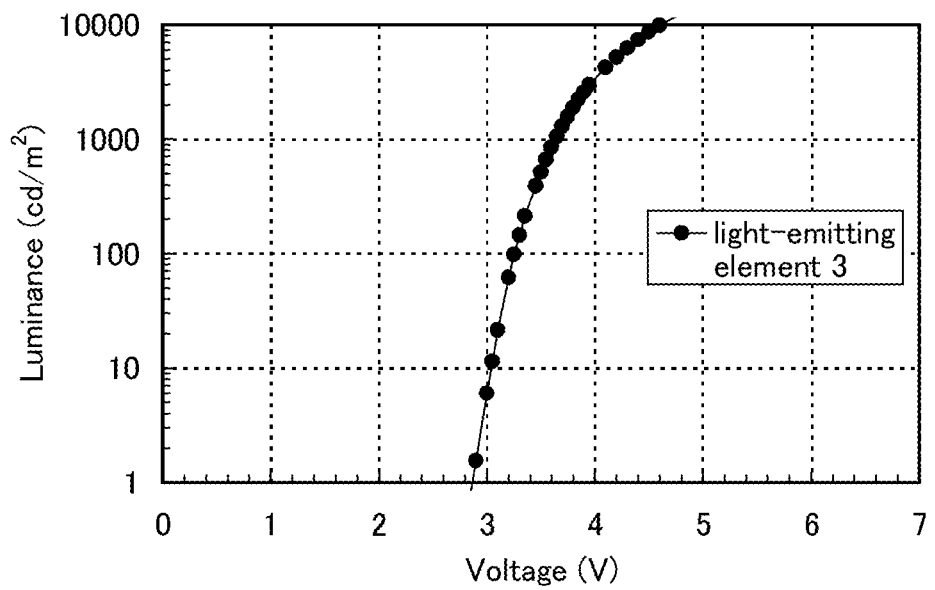
FIG. 17 shows luminance versus voltage characteristics of a light-emitting element of Example 4.
Figure 18:
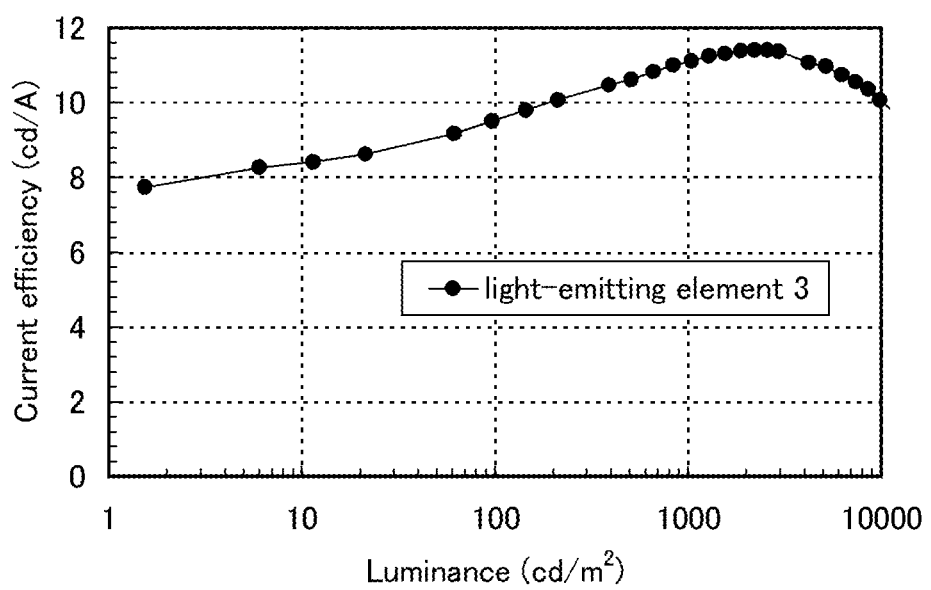
FIG. 18 shows current efficiency versus luminance characteristics of the light-emitting element of Example 4.

The luminance versus voltage characteristics of the light-emitting element 3 are shown in FIG. 17. In FIG. 17, the horizontal axis represents voltage (V) and the vertical axis represents luminance (cd/m²). In addition, the current efficiency versus luminance characteristics of the element are shown in FIG. 18. In FIG. 18, the horizontal axis represents luminance (cd/m²) and the vertical axis represents current efficiency (cd/A). Further, Table 7 shows the voltage (V), CIE chromaticity coordinates (x, y), current efficiency (cd/A), and external quantum efficiency (%) of the light-emitting element 3 at a luminance of 1000 cd/m².

TABLE 7

|  | Voltage (V) | Chromaticity coordinates (x, y) | Current efficiency (cd/A) | External quantum efficiency (%) |
| --- | --- | --- | --- | --- |
| Light-emitting element 3 | 3.7 | (0.14, 0.18) | 11 | 8.4 |

As shown in Table 7, the CIE chromaticity coordinates of the light-emitting element 3 are (x, y)=(0.14, 0.18) at a luminance of 1000 cd/m². This result shows that blue light emission originating from 1,6mMemFLPAPrn was obtained from the light-emitting element 3.

As can be seen from FIG. 17 and FIG. 18, the light-emitting element 3 has high emission efficiency.

Figure 19:
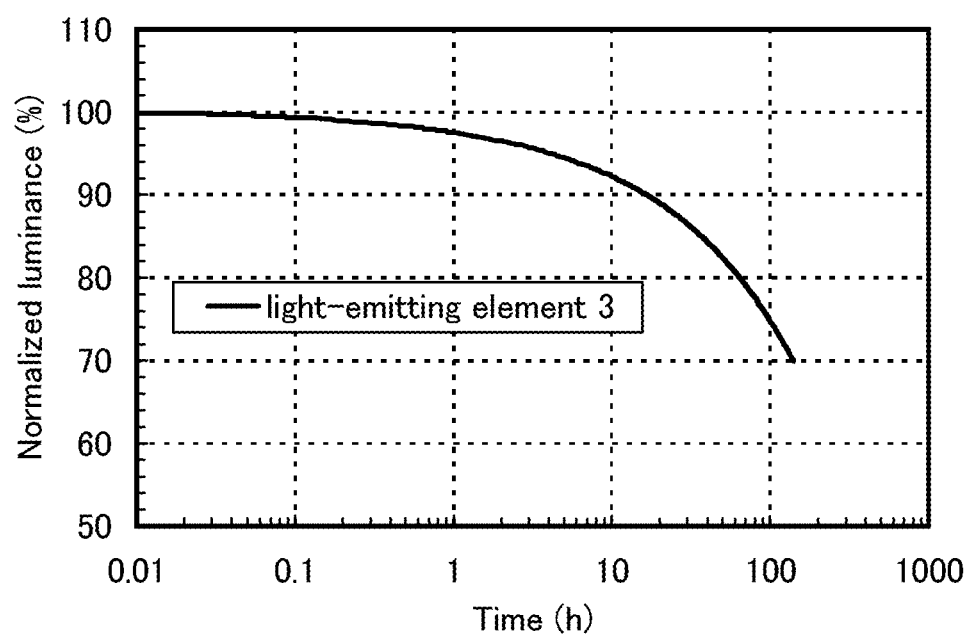
FIG. 19 shows results of a reliability test of the light-emitting element of Example 4.

Next, the light-emitting element 3 was subjected to a reliability test. Results of the reliability test are shown in FIG. 19. In FIG. 19, the vertical axis represents normalized luminance (%) with an initial luminance of 100% and the horizontal axis represents driving time (h) of the element.

In the reliability test, the light-emitting element of this example was driven under the conditions where the initial luminance was set to 5000 cd/m² and the current density was constant.

FIG. 19 shows that the light-emitting element 3 kept 70% of the initial luminance after 140 hours elapsed. It is found that the light-emitting element 3 to which one embodiment of the present invention is applied has a long lifetime.

The above results suggest that an element having high emission efficiency can be achieved when the composite material of one embodiment of the present invention is used for the hole-injection layer and use of the hydrocarbon compound included in the composite material for the hole-transport layer in the light-emitting element. The results also

TABLE 6

|  | First electrode | Hole-injection layer | Hole-transport layer | Light-emitting layer | First electron-transport layer | Second electron-transport layer | Electron-injection layer | Second electrode |
| --- | --- | --- | --- | --- | --- | --- | --- | --- |
| Light-emitting element 3 | ITSO 110 nm | N3P:MoOx (=4:2) 50 nm | N3P 10 nm | CzPA:1,6mMemFLPAPrn (=1:0.04) 30 nm | CzPA 10 nm | BPhen 15 nm | LiF 1 nm | Al 200 nm |

In a glove box containing a nitrogen atmosphere, the light-emitting element 3 was sealed so as not to be exposed to the air. Then, operation characteristics of the light-emitting element 3 were measured. Note that the measurements were carried out at room temperature (in an atmosphere kept at 25° C.).

suggest that a light-emitting element having a long lifetime can be fabricated when the composite material of one embodiment of the present invention is used for the hole-injection layer and use of the hydrocarbon compound included in the composite material for the hole-transport layer.

Example 5

In this example, a light-emitting element of one embodiment of the present invention is described with reference to FIG. 26A. The materials used in this example are the ones used in the above examples, and therefore the chemical formulae thereof are omitted here.

The way how a light-emitting element 4 of this example was fabricated is described below.
(Light-Emitting Element 4)

The hole-transport layer 1112 of the light-emitting element 4 was formed by forming a film of Pn3P to a thickness of 10 nm. Components other than the hole-transport layer 1112 were fabricated in a manner similar to that of the light-emitting element 2.

Table 8 shows element structures of the light-emitting element 4 obtained as described above.

TABLE 8

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 4 | ITSO 110 nm | Pn3P:MoOx (=4:2) 50 nm | Pn3P 10 nm | CzPA: 1,6mMemFLPAPrn (=1:0.04) 30 nm | CzPA 10 nm | BPhen 15 nm | LiF 1 nm | Al 200 nm |

In a glove box containing a nitrogen atmosphere, the light-emitting element 4 was sealed so as not to be exposed to the air. Then, operation characteristics of the light-emitting element 4 were measured. Note that the measurements were carried out at room temperature (in an atmosphere kept at 25° C.).

Figure 20:
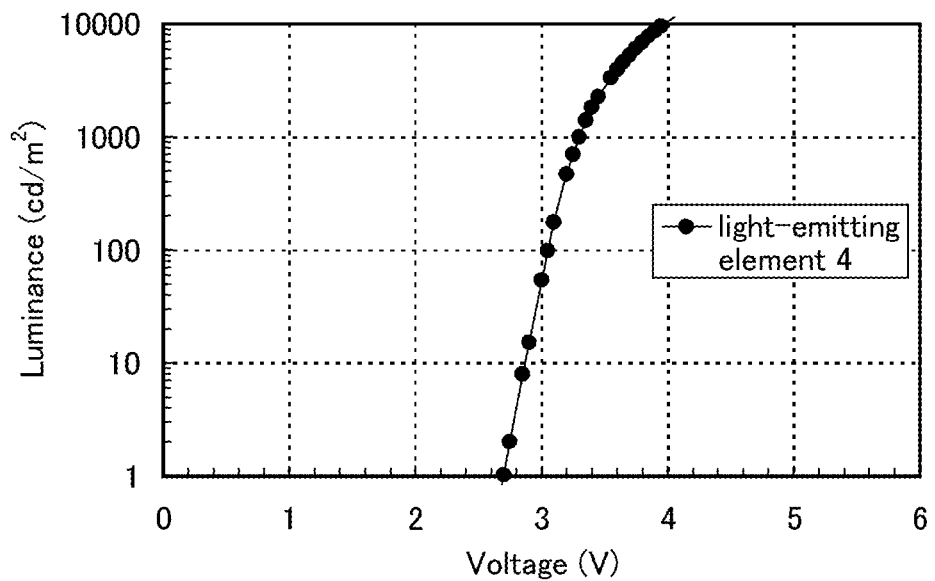
FIG. 20 shows luminance versus voltage characteristics of a light-emitting element of Example 5.
Figure 21:
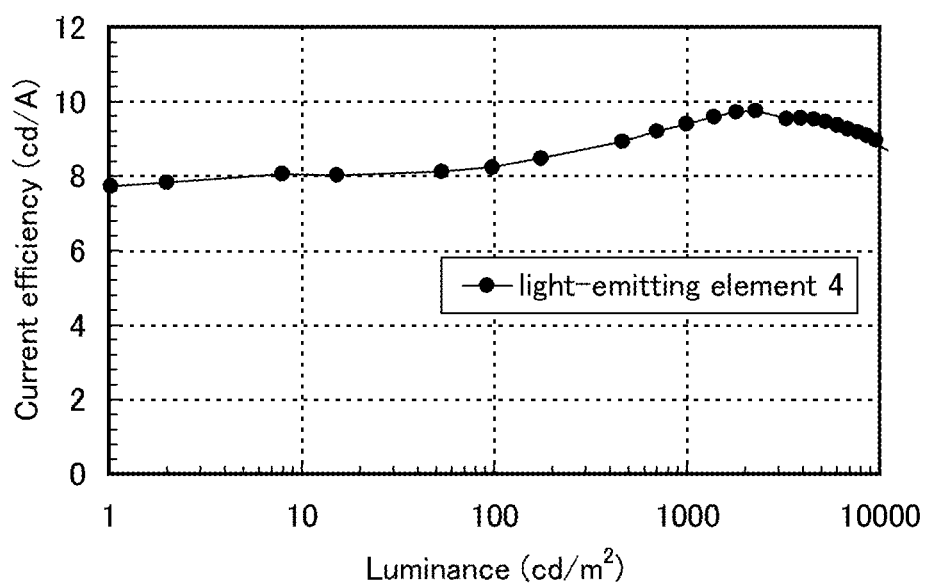
FIG. 21 shows current efficiency versus luminance characteristics of the light-emitting element of Example 5.

The luminance versus voltage characteristics of the light-emitting element 4 are shown in FIG. 20. In FIG. 20, the horizontal axis represents voltage (V) and the vertical axis represents luminance (cd/m$^2$). In addition, the current efficiency versus luminance characteristics of the element are shown in FIG. 21. In FIG. 21, the horizontal axis represents luminance (cd/m$^2$) and the vertical axis represents current efficiency (cd/A). Further, Table 9 shows the voltage (V), CIE chromaticity coordinates (x, y), current efficiency (cd/A), and external quantum efficiency (%) of the light-emitting element 4 at a luminance of 1000 cd/m$^2$.

TABLE 9

| | Voltage (V) | Chromaticity coordinates (x, y) | Current efficiency (cd/A) | External quantum efficiency (%) |
|---|---|---|---|---|
| Light-emitting element 4 | 3.3 | (0.14, 0.17) | 9.4 | 7.5 |

As shown in Table 9, the CIE chromaticity coordinates of the light-emitting element 4 are (x, y)=(0.14, 0.17) at a luminance of 1000 cd/m$^2$. This result shows that blue light emission originating from 1,6mMemFLPAPrn was obtained from the light-emitting element 4.

As can be seen from FIG. 20 and FIG. 21, the light-emitting element 4 has high emission efficiency.

Figure 22:
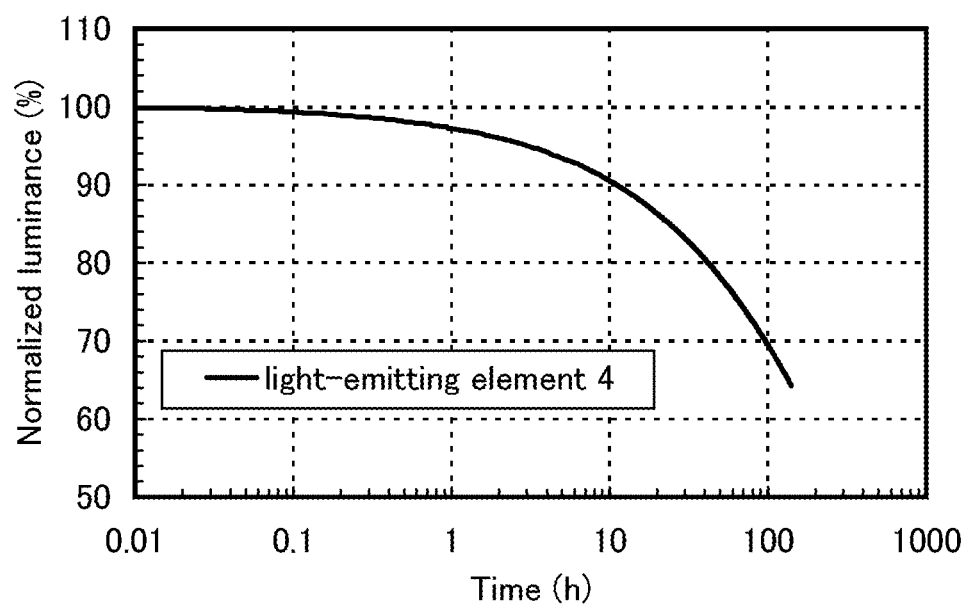
FIG. 22 shows results of a reliability test of the light-emitting element of Example 5.

Next, the light-emitting element 4 was subjected to a reliability test. Results of the reliability test are shown in FIG. 22. In FIG. 22, the vertical axis represents normalized luminance (%) with an initial luminance of 100% and the horizontal axis represents driving time (h) of the element.

In the reliability test, the light-emitting element of this example was driven under the conditions where the initial luminance was set to 5000 cd/m$^2$ and the current density was constant.

FIG. 22 shows that the light-emitting element 4 kept 64% of the initial luminance after 140 hours elapsed. It is found that the light-emitting element 4 to which one embodiment of the present invention is applied has a long lifetime.

The above results suggest that an element having high emission efficiency can be achieved when the composite material of one embodiment of the present invention is used for the hole-injection layer and use of the hydrocarbon compound included in the composite material for the hole-transport layer in the light-emitting element. The results also suggest that a light-emitting element having a long lifetime can be fabricated when the composite material of one embodiment of the present invention is used for the hole-injection layer and use of the hydrocarbon compound included in the composite material for the hole-transport layer.

Further, the results suggest that the light-emitting element can have excellent element characteristics when the composite material of one embodiment of the present invention is used for the hole-injection layer of the light-emitting element and the hydrocarbon compound which can be used for the composite material of one embodiment of the present invention is provided in contact with the composite material in the hole-injection layer. The results also suggest that the light-emitting element can have excellent element characteristics when the hydrocarbon compound which can be used for the composite material of one embodiment of the present invention is provided in contact with the light-emitting layer.

The experimental results of the light-emitting elements 1 to 4 in Examples 2 to 5 show that the composite materials of embodiments of the present invention can be suitably used for a light-emitting element which exhibits blue fluorescence.

Example 6

In this example, a light-emitting element of one embodiment of the present invention is described with reference to FIG. 26A. Note that structural formulae of the materials used in the above example are omitted here.

[Chemical Formula 26]

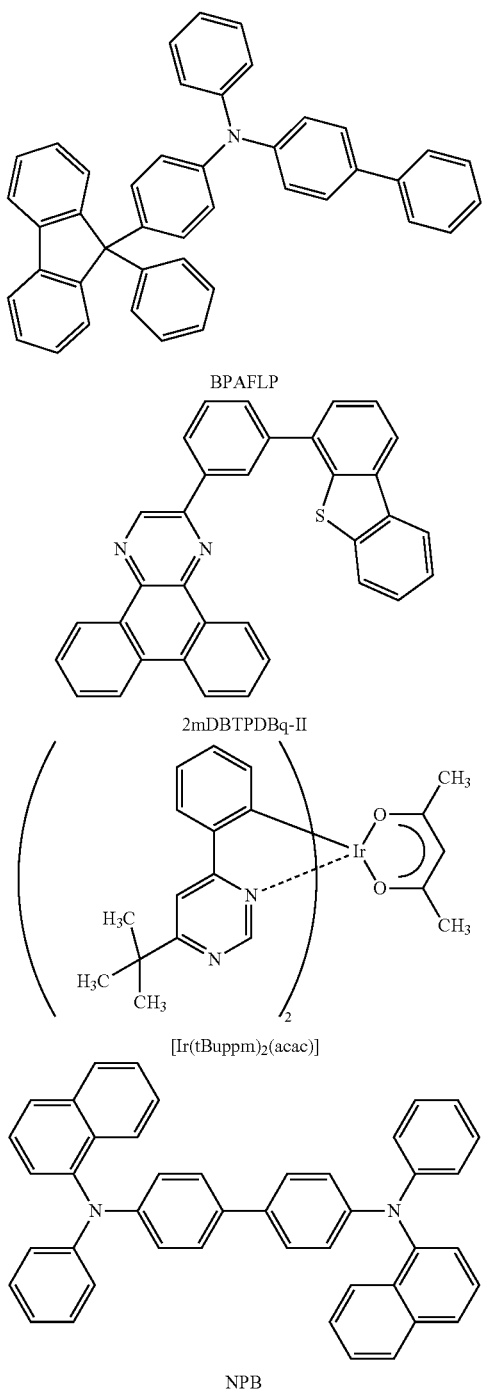

BPAFLP

2mDBTPDBq-II

[Ir(tBuppm)₂(acac)]

NPB

The way how a light-emitting element 5, a light-emitting element 6, and a comparison light-emitting element 7 of this example were fabricated is described below.

(Light-Emitting Element 5)

First, an ITSO film was formed over a glass substrate 1100 by a sputtering method, so that the first electrode 1101 which functions as an anode was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface over which the first electrode 1101 was provided faced downward. The pressure in the vacuum evaporation apparatus was reduced to about $10^{-4}$ Pa. Then, P4N and molybdenum(VI) oxide were co-evaporated to form a hole-injection layer 1111 over the first electrode 1101. The thickness of the hole-injection layer 1111 was set to 40 nm, and the mass ratio of P4N to molybdenum oxide was adjusted to 4:2 (=P4N:molybdenum oxide).

Next, over the hole-injection layer 1111, a film of 4-phenyl-4'-(9-phenylfluoren-9-yl)triphenylamine (abbreviation: BPAFLP) was formed to a thickness of 20 nm to form a hole-transport layer 1112.

Furthermore, 2-[3-(dibenzothiophen-4-yl)phenyl]dibenzo[f,h]quinoxaline (abbreviation: 2mDBTPDBq-II), 4,4'-bis[N-(1-naphthyl)-N-phenylamino]biphenyl (abbreviation: NPB), and (acetylacetonato)bis(6-tert-butyl-4-phenylpyrimidinato)iridium(III) (abbreviation: [Ir(tBuppm)₂(acac)]) were co-evaporated to form a light-emitting layer 1113 over the hole-transport layer 1112. Here, the mass ratio of 2mDBTPDBq-II to NPB and [Ir(tBuppm)₂(acac)] was adjusted to 0.8:0.2:0.05 (=2mDBTPDBq-II:NPB:[Ir(tBuppm)₂(acac)]). In addition, the thickness of the light-emitting layer 1113 was set to 40 nm.

Further, over the light-emitting layer 1113, a film of 2mDBTPDBq-II was formed to a thickness of 10 nm to form a first electron-transport layer 1114a.

Then, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form the electron-injection layer 1115.

Lastly, an aluminum film was formed by evaporation to a thickness of 200 nm as the second electrode 1103 functioning as a cathode. Thus, the light-emitting element 5 of this example was fabricated.

Note that, in all the above evaporation steps, evaporation was performed by a resistance-heating method.

(Light-Emitting Element 6)

A hole-injection layer 1111 of the light-emitting element 6 was formed by co-evaporating Pn3P and molybdenum(VI) oxide. The thickness of the hole-injection layer 1111 was set to 40 nm, and the mass ratio of Pn3P to molybdenum oxide was adjusted to 4:2 (=Pn3P:molybdenum oxide). Components other than the hole-injection layer 1111 were fabricated in a manner similar to that of the light-emitting element 5.

(Comparison Light-Emitting Element 7)

A hole-injection layer 1111 of the comparison light-emitting element 7 was formed by co-evaporating DPAnth and molybdenum(VI) oxide. The thickness of the hole-injection layer 1111 was set to 40 nm, and the mass ratio of DPAnth to molybdenum oxide was adjusted to 4:2 (=DPAnth:molybdenum oxide). Components other than the hole-injection layer 1111 were fabricated in a manner similar to that of the light-emitting element 5.

Table 10 shows element structures of the light-emitting element 5, the light-emitting element 6, and the comparison light-emitting element 7 formed as described above.

TABLE 10

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 5 | ITSO 110 nm | P4N:MoOx (=4:2) 40 nm | BPAFLP 10 nm | 2mDBTPDBq-II: NPB: [Ir(tBuppm)$_2$(acac)] (=0.8:0.2:0.05) 40 nm | 2mDBTPDBq-II 10 nm | BPhen 20 nm | LiF 1 nm | Al 200 nm |
| Light-emitting element 6 | ITSO 110 nm | Pn3P:MoOx (=4:2) 40 nm | BPAFLP 10 nm | 2mDBTPDBq-II: NPB: [Ir(tBuppm)$_2$(acac)] (=0.8:0.2:0.05) 40 nm | 2mDBTPDBq-II 10 nm | BPhen 20 nm | LiF 1 nm | Al 200 nm |
| Comparison light-emitting element 7 | ITSO 110 nm | DPAnth:MoOx (=4:2) 40 nm | BPAFLP 10 nm | 2mDBTPDBq-II: NPB: [Ir(tBuppm)$_2$(acac)] (=0.8:0.2:0.05) 40 nm | 2mDBTPDBq-II 10 nm | BPhen 20 nm | LiF 1 nm | Al 200 nm |

In a glove box containing a nitrogen atmosphere, these light-emitting elements were sealed so as not to be exposed to the air. Then, operation characteristics of these light-emitting elements were measured. Note that the measurements were carried out at room temperature (in an atmosphere kept at 25° C.).

Figure 23:
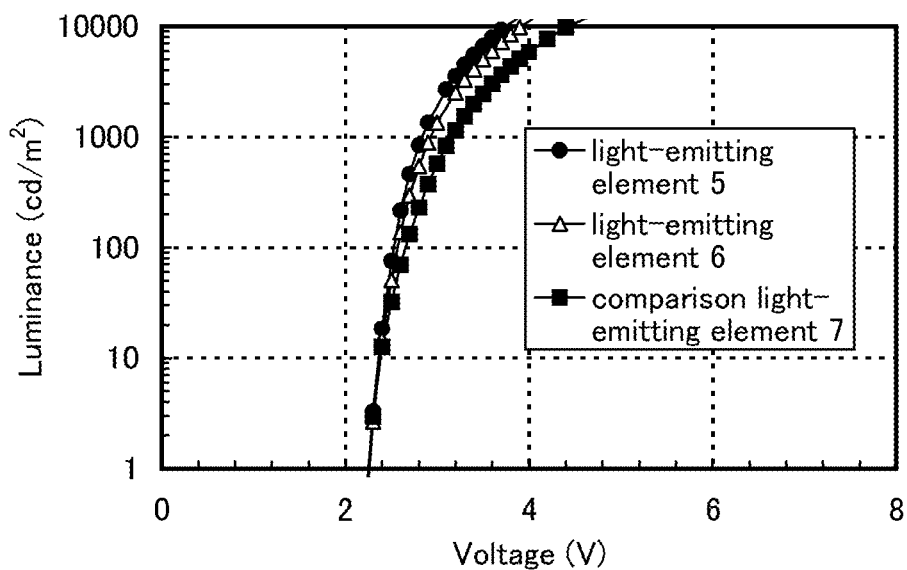
FIG. 23 shows luminance versus voltage characteristics of light-emitting elements of Example 6.
Figure 24:
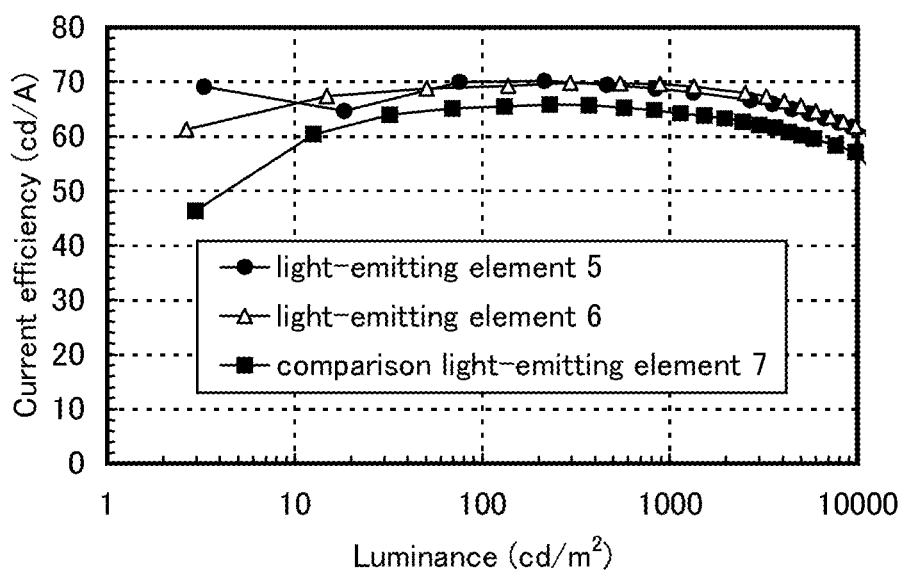
FIG. 24 shows current efficiency versus luminance characteristics of the light-emitting elements of Example 6.

The luminance versus voltage characteristics of the light-emitting element 5, the light-emitting element 6, and the comparison light-emitting element 7 are shown in FIG. 23. In FIG. 23, the horizontal axis represents voltage (V) and the vertical axis represents luminance (cd/m$^2$). In addition, the current efficiency versus luminance characteristics of the elements are shown in FIG. 24. In FIG. 24, the horizontal axis represents luminance (cd/m$^2$) and the vertical axis represents current efficiency (cd/A). Further, Table 11 shows the voltage (V), CIE chromaticity coordinates (x, y), current efficiency (cd/A), and external quantum efficiency (%) of each light-emitting element at a luminance of 1000 cd/m$^2$.

TABLE 11

| | Voltage (V) | Chromaticity coordinates (x, y) | Luminance (cd/m$^2$) | Current efficiency (cd/A) | External quantum efficiency (%) |
|---|---|---|---|---|---|
| Light-emitting element 5 | 2.8 | (0.45, 0.54) | 840 | 69 | 20 |
| Light-emitting element 6 | 2.9 | (0.45, 0.55) | 890 | 70 | 20 |
| Comparison light-emitting element 7 | 3.2 | (0.45, 0.55) | 1100 | 64 | 18 |

As shown in Table 11, the CIE chromaticity coordinates of the light-emitting element 5 are (x, y)=(0.45, 0.54) at a luminance of 840 cd/m$^2$, the CIE chromaticity coordinates of the light-emitting element 6 are (x, y)=(0.45, 0.55) at a luminance of 890 cd/m$^2$, and the CIE chromaticity coordinates of the comparison light-emitting element 7 are (x, y)=(0.45, 0.55) at a luminance of 1100 cd/m$^2$. These results show that orange light emission originating from [Ir(tBuppm)$_2$(acac)] was obtained from the light-emitting elements of this example.

As can be seen from FIG. 23 and FIG. 24, the light-emitting elements 5 and 6 have lower driving voltage and higher emission efficiency than the comparison light-emitting element 7.

Figure 25:
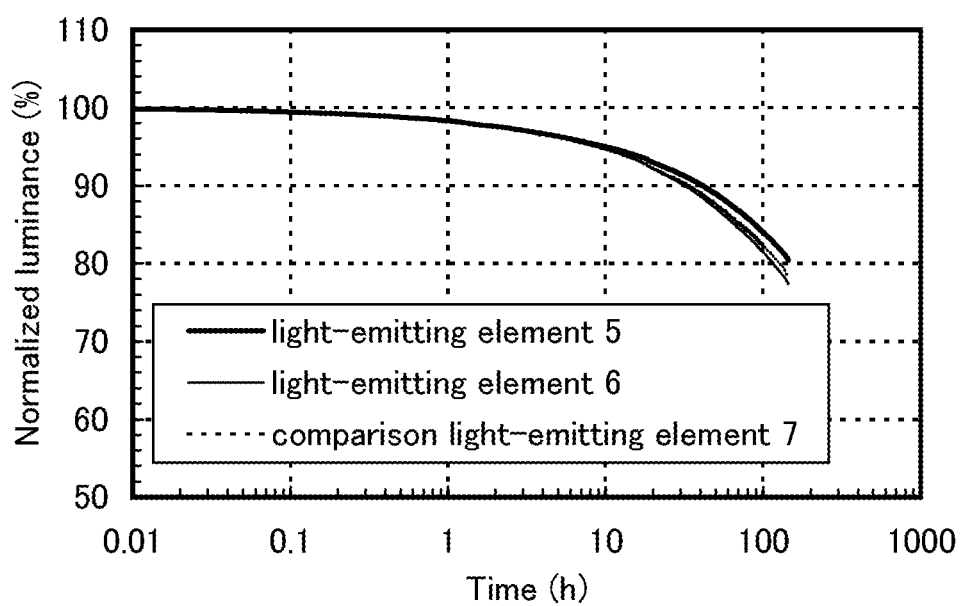
FIG. 25 shows results of reliability tests of the light-emitting elements of Example 5.

Next, the light-emitting elements were subjected to reliability tests. Results of the reliability tests are shown in FIG. 25. In FIG. 25, the vertical axis represents normalized luminance (%) with an initial luminance of 100% and the horizontal axis represents driving time (h) of the elements.

In the reliability tests, the light-emitting elements of this example were driven under the conditions where the initial luminance was set to 5000 cd/m$^2$ and the current density was constant.

FIG. 25 shows that the light-emitting element 5 kept 80% of the initial luminance after 150 hours elapsed, the light-emitting element 6 kept 77% of the initial luminance after 150 hours elapsed, and the comparison light-emitting element 7 kept 78% of the initial luminance after 150 hours elapsed.

It is found that the light-emitting elements 5 and 6 have as high reliability as the comparison light-emitting element 7.

The above results suggest that an element having high emission efficiency can be achieved when the composite material of one embodiment of the present invention is used for the hole-injection layer of the light-emitting element which exhibits phosphorescence. The results also suggest that a light-emitting element having a low driving voltage can be provided when the composite material of one embodiment of the present invention is used for the hole-injection layer of the light-emitting element which exhibits phosphorescence. The results also suggest that a light-emitting element having a long lifetime can be manufactured when the composite material of one embodiment of the present invention is used for the hole-injection layer of the light-emitting element which exhibits phosphorescence.

Further, the results suggest that the composite material of one embodiment of the present invention can be suitably used for the hole-injection layer of the light-emitting element which exhibits orange phosphorescence. It is thus found that the composite material can be suitably used for a light-emitting element which exhibits orange light or light having a longer wavelength than orange light.

Example 7

Figure 26B:
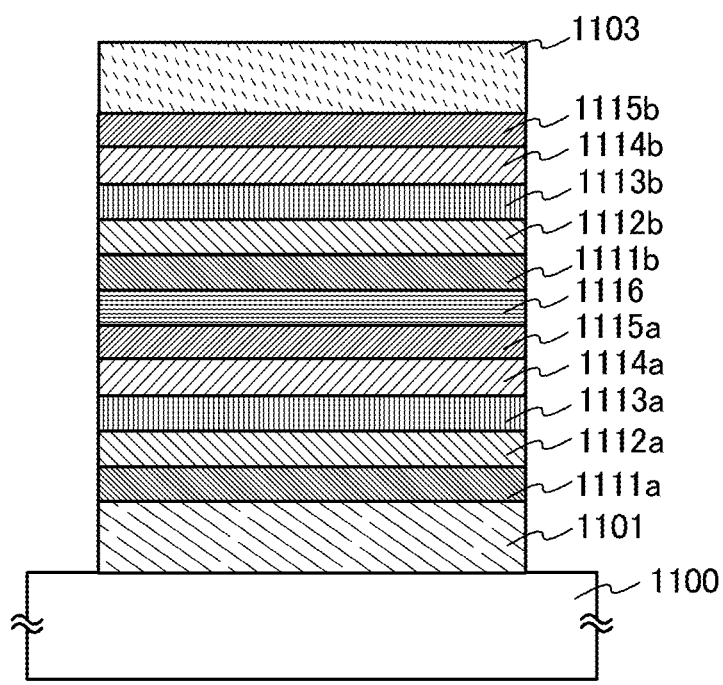

In this example, a light-emitting element of one embodiment of the present invention is described with reference to FIG. 26B. Structural formulae of materials used in this example are illustrated below. Note that structural formulae of the materials used in the above examples are omitted here.

[Chemical Formula 27]

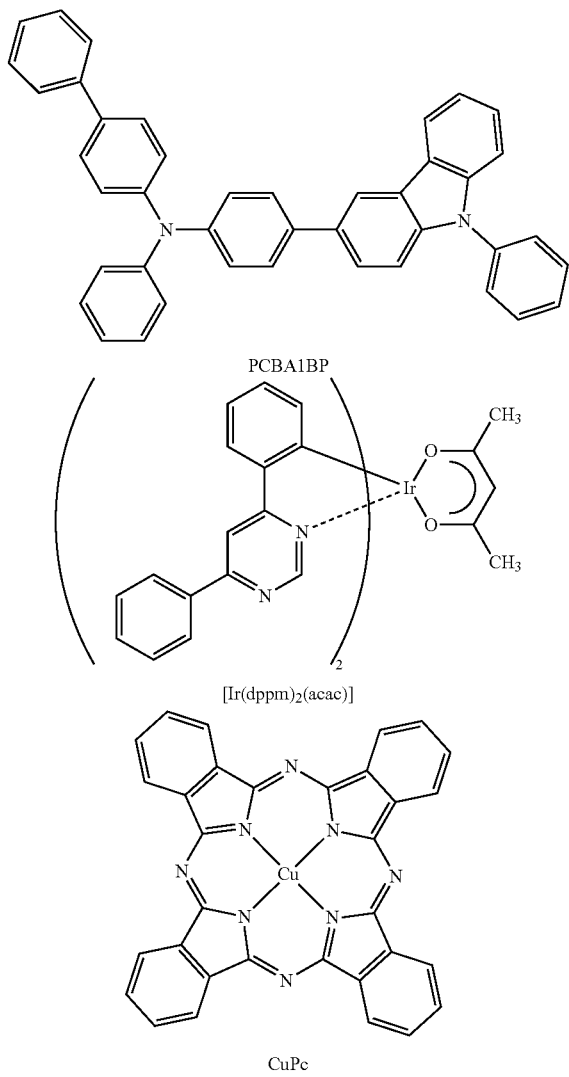

The way how a light-emitting element 8 of this example was fabricated is described below.
(Light-Emitting Element 8)

First, an ITSO film was formed over a glass substrate 1100 by a sputtering method, so that the first electrode 1101 which functions as an anode was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface over which the first electrode 1101 was provided faced downward. The pressure in the vacuum evaporation apparatus was reduced to about $10^{-4}$ Pa. Then, Pn3P and molybdenum(VI) oxide were co-evaporated to form a first hole-injection layer 1111a over the first electrode 1101. The thickness of the first hole-injection layer 1111a was set to 33 nm, and the mass ratio of Pn3P to molybdenum(VI) oxide was adjusted to 1:0.5 (=Pn3P:molybdenum oxide).

Next, over the first hole-injection layer 1111a, a film of PCPN was formed to a thickness of 30 nm to form a first hole-transport layer 1112a.

Next, CzPA and 1,6mMemFLPAPm were co-evaporated to form a first light-emitting layer 1113a over the first hole transport-layer 1112a. Here, the mass ratio of CzPA to 1,6mMemFLPAPm was adjusted to 1:0.05 (=CzPA:1,6mMemFLPAPm). The thickness of the first light-emitting layer 1113a was set to 30 nm.

Next, over the first light-emitting layer 1113a, a CzPA film was formed to a thickness of 5 nm and a BPhen film was formed to a thickness of 15 nm to form a first electron-transport layer 1114a.

Further, over the first electron-transport layer 1114a, a film of lithium oxide ($Li_2O$) was formed by evaporation to a thickness of 0.1 nm to form a first electron-injection layer 1115a.

After that, over the first electron-injection layer 1115a, a film of copper phthalocyanine (abbreviation: CuPc) was formed by evaporation to a thickness of 2 nm to form an electron-relay layer 1116.

Next, over the electron-relay layer 1116, Pn3P and molybdenum(VI) oxide were co-evaporated to form a second hole-injection layer 1111b. The thickness of the second hole-injection layer 1111b was set to 40 nm, and the mass ratio of Pn3P to molybdenum oxide was adjusted to 1:0.5 (=Pn3P:molybdenum oxide). Note that the second hole-injection layer 1111b of this example functions as the charge-generation layer described in the above embodiment.

Next, over the second hole-injection layer 1111b, a PCPN film was formed to a thickness of 20 nm to form a second hole-transport layer 1112b.

Further, 2mDBTPDBq-II, 4-phenyl-4'-(9-phenyl-9H-carbazol-3-yl)triphenylamine (abbreviation: PCBA1BP), and (acetylacetonato)bis(4,6-diphenylpyrimidinato)iridium(III) (abbreviation: [Ir(dppm)$_2$(acac)]) were co-evaporated to form a second light-emitting layer 1113b over the second hole-transport layer 1112b. Here, the mass ratio of 2mDBTPDBq-II to PCBA1BP and [Ir(dppm)$_2$(acac)] was adjusted to 0.8:0.2:0.06 (=2mDBTPDBq-II:PCBA1BP:[Ir(dppm)$_2$(acac)]). In addition, the thickness of the second light-emitting layer 1113b was set to 40 nm.

Next, over the second light-emitting layer 1113b, a film of 2mDBTPDBq-II was formed to a thickness of 15 nm and a film of BPhen was formed to a thickness of 15 nm to form a second electron-transport layer 1114b.

Further, over the second electron-transport layer 1114b, a film of LiF was formed to a thickness of 1 nm to form a second electron-injection layer 1115b.

Lastly, an aluminum film was formed by evaporation to a thickness of 200 nm as the second electrode 1103 functioning as a cathode. Thus, the light-emitting element 8 of this example was fabricated.

Note that, in all the above evaporation steps, evaporation was performed by a resistance-heating method.

Table 12 shows element structures of the light-emitting element 8 obtained as described above.

TABLE 12

| First electrode ITSO 110 nm | | | | | |
|---|---|---|---|---|---|
| First hole-injection layer | First hole-transport layer | First Light-emitting layer | First electron-transport layer | First electron-injection layer | Electron relay layer |
| Pn3P:MoOx (=1:0.5) 33 nm | PCPN 30 nm | CzPA: 1,6mMemFLPAPrn (=1:0.05) 30 nm | CzPA 5 nm | BPhen 15 nm | $Li_2O$ 0.1 nm | CuPc 2 nm |
| Second hole-injection layer | Second hole-transport layer | Second Light-emitting layer | Second electron-transport layer | Second electron-injection layer | Second electrode |
| Pn3P:MoOx (=1:0.5) 40 nm | PCPN 20 nm | 2mDBTPDBq-II: PCBA1BP: Ir(dppm)$_2$(acac) (=0.8:0.2:0.06) 40 nm | 2mDBTPDBq-II 15 nm | BPhen 15 nm | LiF 1 nm | Al 200 nm |

In a glove box containing a nitrogen atmosphere, the light-emitting element 8 was sealed so as not to be exposed to the air. Then, operation characteristics of the light-emitting element 8 were measured. Note that the measurements were carried out at room temperature (in an atmosphere kept at 25° C.).

Figure 28:
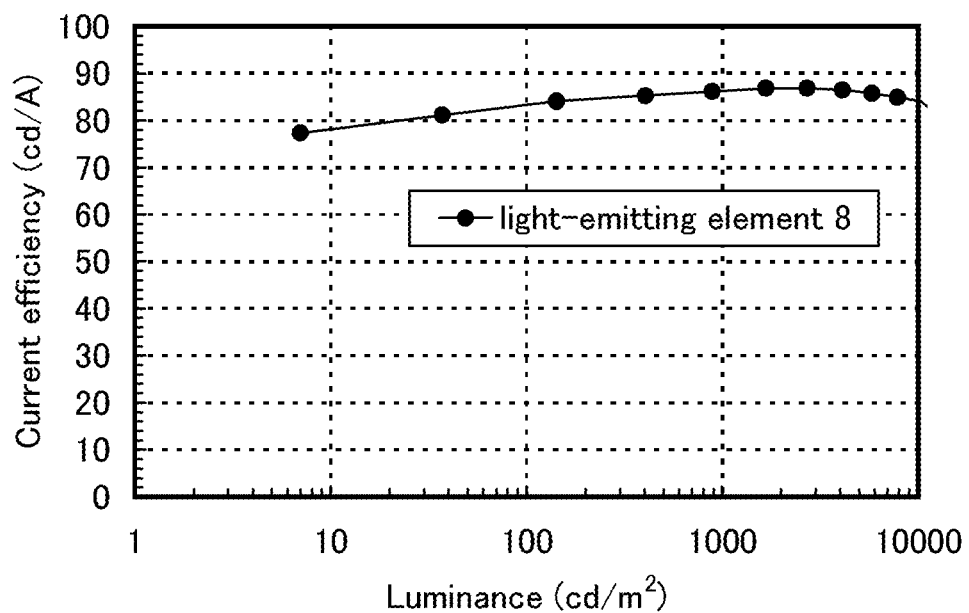
FIG. 28 shows current efficiency versus luminance characteristics of a light-emitting element of Example 7.
Figure 29:
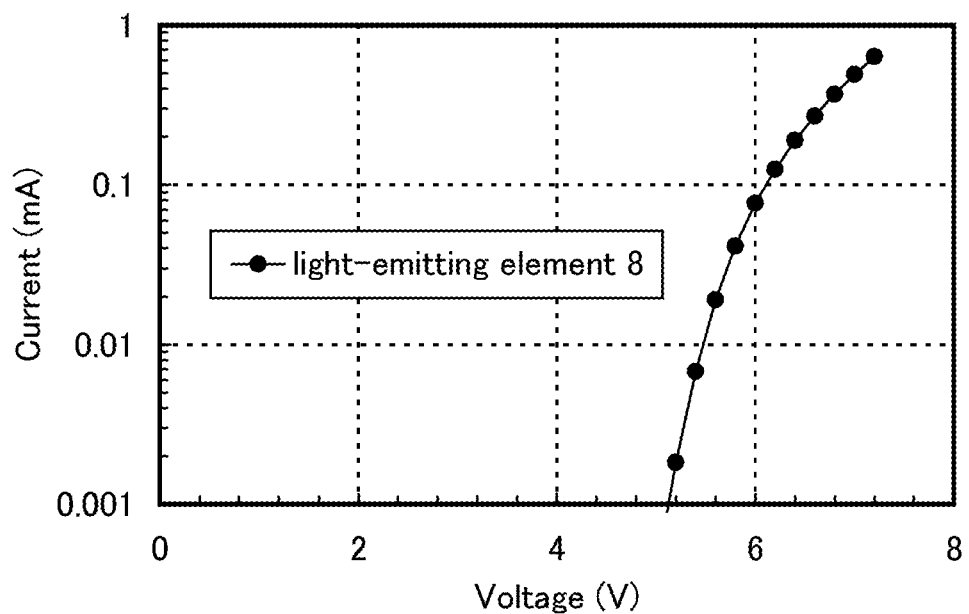
FIG. 29 shows current versus voltage characteristics of the light-emitting element of Example 7.
Figure 30:
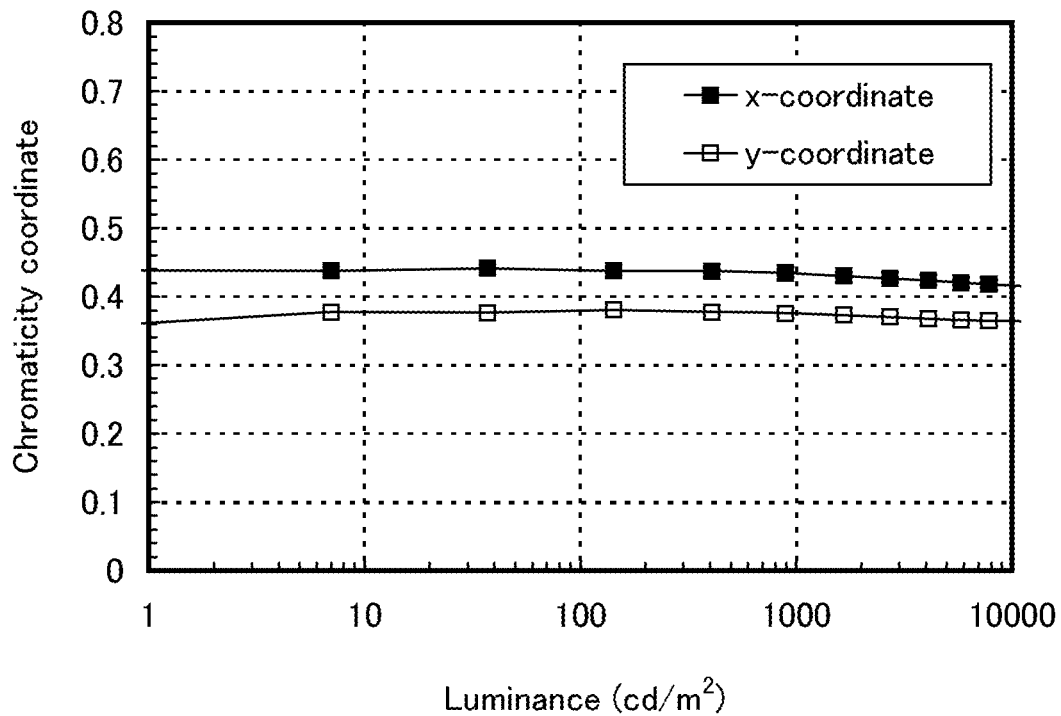
FIG. 30 shows chromaticity coordinate versus luminance characteristics of the light-emitting element of Example 7.
Figure 31:
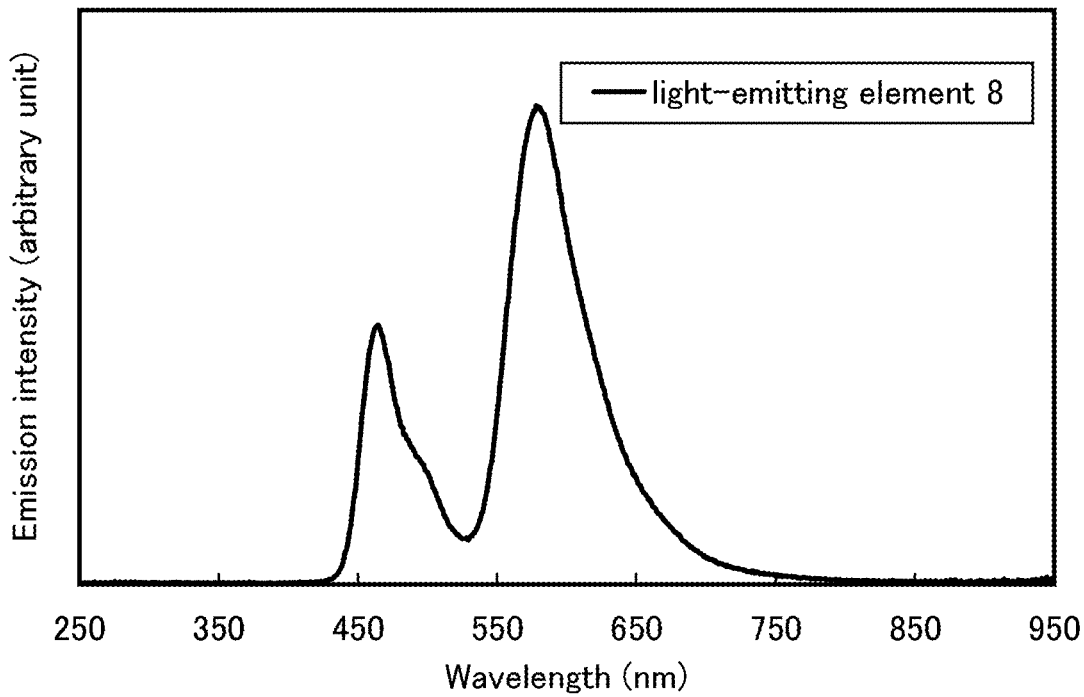
FIG. 31 shows an emission spectrum of the light-emitting element of Example 7.

The current efficiency versus luminance characteristics of the light-emitting element 8 are shown in FIG. 28. In FIG. 28, the horizontal axis represents luminance (cd/m$^2$) and the vertical axis represents current efficiency (cd/A). In addition, the current versus voltage characteristics are shown in FIG. 29. In FIG. 29, the horizontal axis represents voltage (V) and the vertical axis represents current (mA). Further, the chromaticity coordinate versus luminance characteristics are shown in FIG. 30. In FIG. 30, the horizontal axis represents luminance (cd/m$^2$) and the vertical axis represents chromaticity coordinates (the x-coordinate and the y-coordinate). In addition, FIG. 31 shows an emission spectrum of the light-emitting element 8 which was obtained by applying a current of 0.1 mA. In FIG. 31, the horizontal axis represents wavelength (nm) and the vertical axis represents emission intensity (arbitrary unit). Further, Table 13 shows the voltage (V), CIE chromaticity coordinates (x, y), current efficiency (cd/A), external quantum efficiency (%), and correlated color temperature (K) of the light-emitting element 8 at a luminance of 890 cd/m$^2$.

TABLE 13

| | Voltage (V) | Chromaticity coordinates (x, y) | Current efficiency (cd/A) | External quantum efficiency (%) | Correlated color temperature (K) |
|---|---|---|---|---|---|
| Light-emitting element 8 | 5.8 | (0.43, 0.38) | 86 | 36 | 2800 |

As shown in Table 13, the CIE chromaticity coordinates of the light-emitting element 8 are (x, y)=(0.43, 0.38) at a luminance of 890 cd/m$^2$. Further, FIG. 31 shows that in the light-emitting element 8, the blue light-emitting material (1,6mMemFLPAPrn) and the orange light-emitting material ([Ir(dppm)$_2$(acac)]) emit light with a good balance. In addition, FIG. 30 shows that the light-emitting element 8 undergoes a small change in chromaticity which depends on luminance, indicating its excellent carrier balance. Thus, the light-emitting element 8 is found suitable for use for a lighting device. Furthermore, as shown in Table 3, the correlated color temperature is 2800K. Light emission with a color close to an incandescent color is obtained from the light-emitting element 8, which also indicates the suitability for use for a lighting device.

The above results suggest that an element having high emission efficiency can be achieved when the composite material of one embodiment of the present invention is used for the hole-injection layer and the charge-generation layer in the tandem light-emitting element. The results also suggest that a light-emitting element having a low driving voltage can be provided when the composite material of one embodiment of the present invention is used for the hole-injection layer and the charge-generation layer in the tandem light-emitting element. The results also suggest that the composite material of one embodiment of the present invention can be suitably used for the light-emitting element for exhibiting white light emission.

Example 8

In this example, the composite material of one embodiment of the present invention is specifically exemplified. Table 14 shows the hydrocarbon compound used in Composition Example 4 of this example and the HOMO level (eV) of the hydrocarbon compound. Note that the HOMO level is measured by photoelectron spectroscopy. In addition, the structural formula of the hydrocarbon compound is illustrated below.

TABLE 14

| | Hydrocarbon compound | HOMO level (eV) |
|---|---|---|
| Composition Example 4 | βN3P | −6.0 |

[Chemical Formula 28]

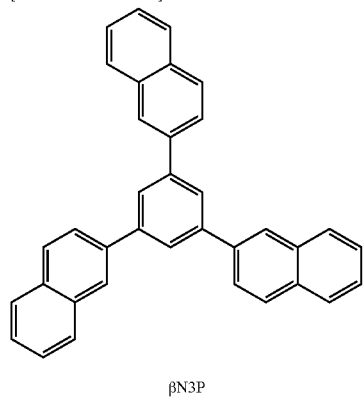

βN3P

Figure 34A:
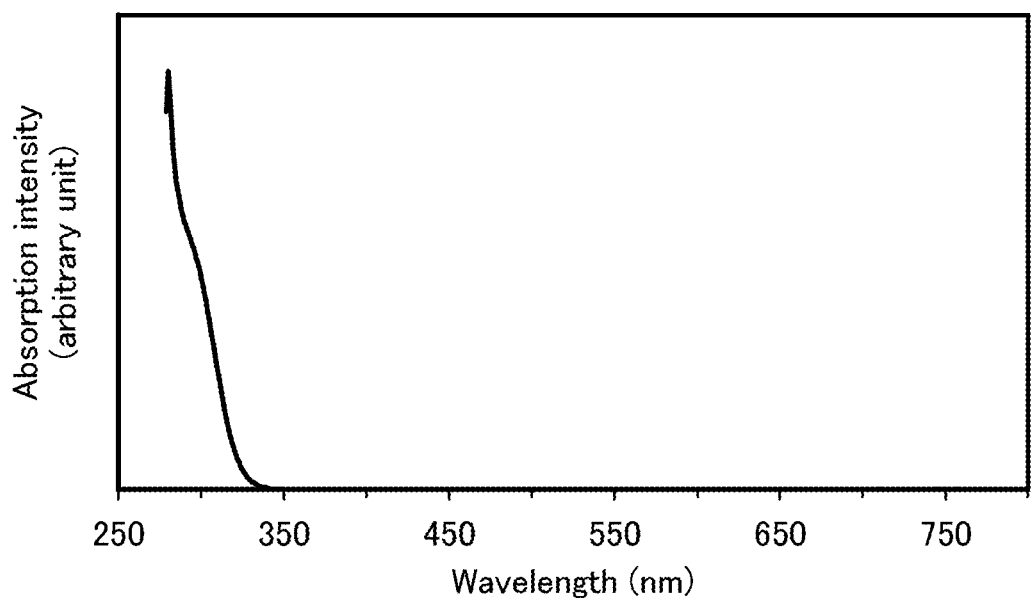
FIGS. 34A and 34B show an absorption and emission spectra of βN3P in a toluene solution of βN3P.
Figure 34B:
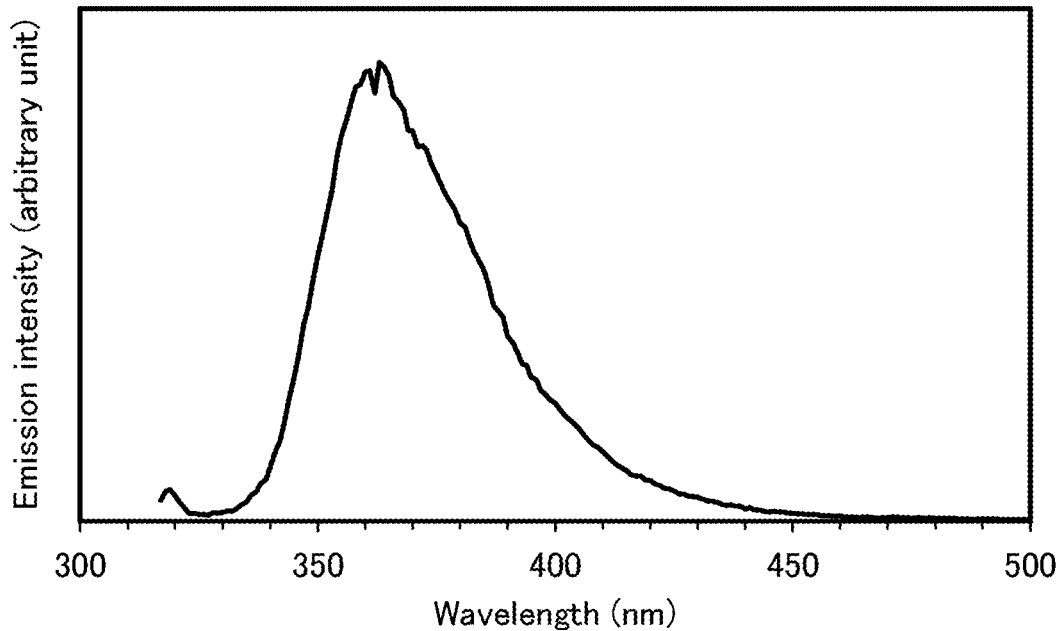

Further, FIG. 34A shows an absorption spectrum of βN3P in a toluene solution of βN3P, and FIG. 34B shows an emission spectrum thereof. The absorption spectrum was measured using an ultraviolet-visible spectrophotometer (V-550, produced by JASCO Corporation). The measurements were performed in such a way that each solution was put in a quartz cell. Here is shown the absorption spectrum which was obtained by subtraction of the absorption spectra of quartz and toluene from those of quartz and the solution. In FIG. 34A, the horizontal axis represents wavelength (nm) and the vertical axis represents absorption intensity (arbitrary unit). In FIG. 34B, the horizontal axis represents wavelength (nm) and the vertical axis represents emission intensity (arbitrary unit). Further, βN3P exhibits an absorption peak at around 296 nm and an emission wavelength peak at 363 nm (at an excitation wavelength of 291 nm).

It is thus found from the absorption spectra of the hydrocarbon compounds in the toluene solutions, each of which is used for the composite material of one embodiment of the present invention, that absorption in the visible light region is hardly observed. In addition, since the emission peaks are located at the shorter wavelengths, the hydrocarbon compounds are each found suitable for a material of the hole-transport layer in contact with a light-emitting layer and for a host material of a light-emitting layer.

The thin film of the hydrocarbon compound used for the composite material of one embodiment of the present invention also exhibits almost no absorption spectrum in the visible light region, which is described later (see FIGS. 35A and 35B). The fact that both the solution and the thin film exhibit almost no absorption in the visible light region indicates the hydrocarbon compound is suitable for both a film of a single substance and for a film of a mixture. Thus, the hydrocarbon compound can be suitably used for any of the composite material of one embodiment of the present invention, a hole-transport layer, and a light-emitting layer.

In Composition Example 4, molybdenum oxide was used as the inorganic compound.

The way how the composite material of one embodiment of the present invention was prepared is described.

Composition Example 4

First, a glass substrate was fixed to a substrate holder inside a vacuum evaporation apparatus. Then, 2-[3,5-di-(naphthalen-2-yl)-phenyl]-naphthalene (abbreviation: βN3P) and molybdenum(VI) oxide were separately put in respective resistance-heating evaporation sources, and in a vacuum state, films containing βN3P and molybdenum oxide were formed by a co-evaporation method. At this time, βN3P and molybdenum oxide were co-evaporated such that the mass ratios of βN3P to molybdenum oxide were 4:2, 4:1, and 4:0.5 (=βN3P:molybdenum oxide). Further, the thickness of each film was set to 50 nm.

Figure 35A:
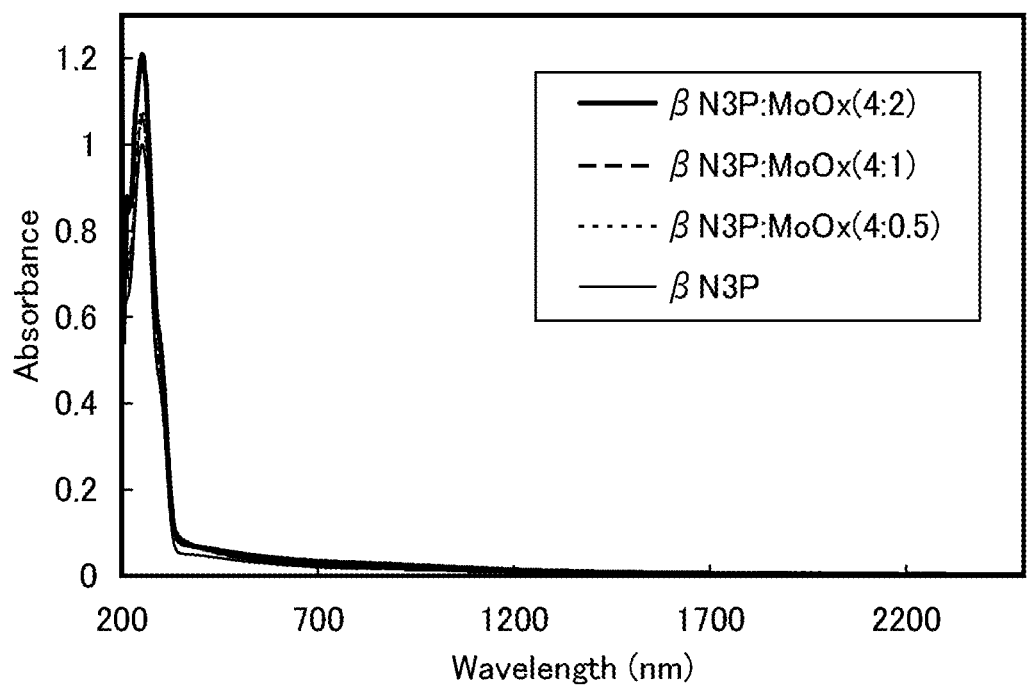
FIGS. 35A and 35B show absorbances of βN3P and a composite material thereof according to Example 8.
Figure 35B:
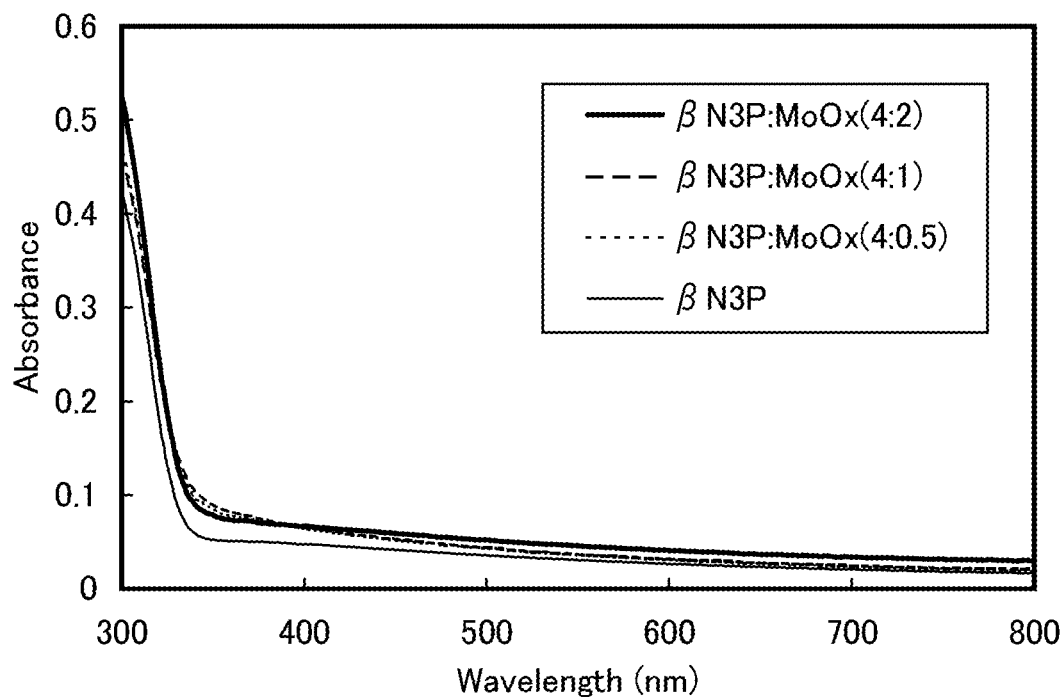

FIGS. 35A and 35B show measurement results of absorption spectra of the thus formed composite films of βN3P and molybdenum oxide (Composition Example 4). In addition, for comparison, an absorption spectrum of a film of only βN3P (50 nm thick) is also shown in the drawings. In each of FIGS. 35A and 35B, the horizontal axis represents a wavelength (nm) and the vertical axis represents absorbance (no unit).

The composite material described in Composition Example 4 (FIGS. 35A and 35B) does not exhibit a significant absorption peak in the wavelength region of at least 360 nm or more and is found to have a high light-transmitting property. It is thus found that the composite material of one embodiment of the present invention is a material that has almost no significant absorption peak in the visible light region and has a high light-transmitting property. Further, the composite material of one embodiment of the present invention exhibited almost no significant absorption peak also in the infrared region (the wavelength region of 700 nm or more).

The absorption spectrum of the composite material of one embodiment of the present invention, which includes the hydrocarbon compound and molybdenum oxide, has substantially the same shape as the absorption spectrum of the hydrocarbon compound. Almost no significant absorption peak in the visible to infrared region even in the case of a film having a high concentration of molybdenum oxide (specifically, the film in which the mass ratio of the hydrocarbon compound to molybdenum oxide is 4:2). This indicates that in the composite material of one embodiment of the present invention, light absorption due to charge-transfer interaction is unlikely to occur.

Example 9

In this example, a light-emitting element of one embodiment of the present invention is described with reference to FIG. 26A. Note that structural formulae of the materials used in the above example are omitted here.

[Chemical Formula 29]

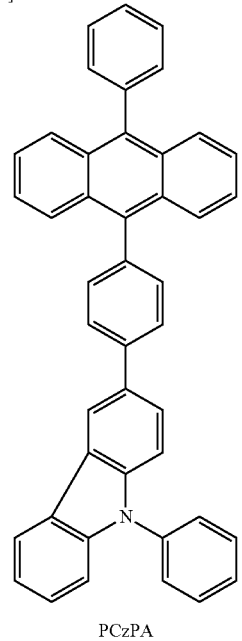

PCzPA

The way how a light-emitting element 9 of this example was fabricated is described below.
(Light-Emitting Element 9)

First, a film of ITSO was formed over a glass substrate 1100 by a sputtering method, so that the first electrode 1101 which functions as an anode was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface over which the first electrode 1101 was provided faced downward. The pressure in the vacuum evaporation apparatus was reduced to about $10^{-4}$ Pa. Then, βN3P and molybdenum(VI) oxide were co-evaporated to form a hole-injection layer 1111 over the first electrode 1101. The thickness of the hole-injection layer 1111 was set to 50 nm, and the mass ratio of βN3P to molybdenum oxide was adjusted to 4:2 (=βN3P:molybdenum oxide).

Next, over the hole-injection layer 1111, a film of 9-phenyl-3-[4-(10-phenyl-9-anthryl)phenyl]-9H-carbazole (abbreviation: PCzPA) was formed to a thickness of 10 nm to form a hole-transport layer 1112.

Furthermore, CzPA and 1,6mMemFLPAPm were co-evaporated to form the light-emitting layer 1113 over the hole-transport layer 1112. Here, the mass ratio of CzPA to 1,6mMemFLPAPm was adjusted to 1:0.04 (=CzPA:1,6mMemFLPAPm). In addition, the thickness of the light-emitting layer 1113 was set to 30 nm.

Further, over the light-emitting layer 1113, a film of CzPA was formed to a thickness of 10 nm to form the first electron-transport layer 1114a.

Then, over the first electron-transport layer 1114a, a film of BPhen was formed to a thickness of 15 nm to form the second electron-transport layer 1114b.

Further, over the second electron-transport layer 1114b, a film of LiF was formed by evaporation to a thickness of 1 nm to form the electron-injection layer 1115.

Lastly, an aluminum film was formed by evaporation to a thickness of 200 nm as the second electrode 1103 functioning as a cathode. Thus, the light-emitting element 9 of this example was fabricated.

Note that, in all the above evaporation steps, evaporation was performed by a resistance-heating method.

Table 15 shows element structures of the light-emitting element 9 obtained as described above.

In a glove box containing a nitrogen atmosphere, the light-emitting element 9 was sealed so as not to be exposed to the air. Then, operation characteristics of the light-emitting element 9 were measured. Note that the measurements were carried out at room temperature (in an atmosphere kept at 25° C.).

Figure 36:
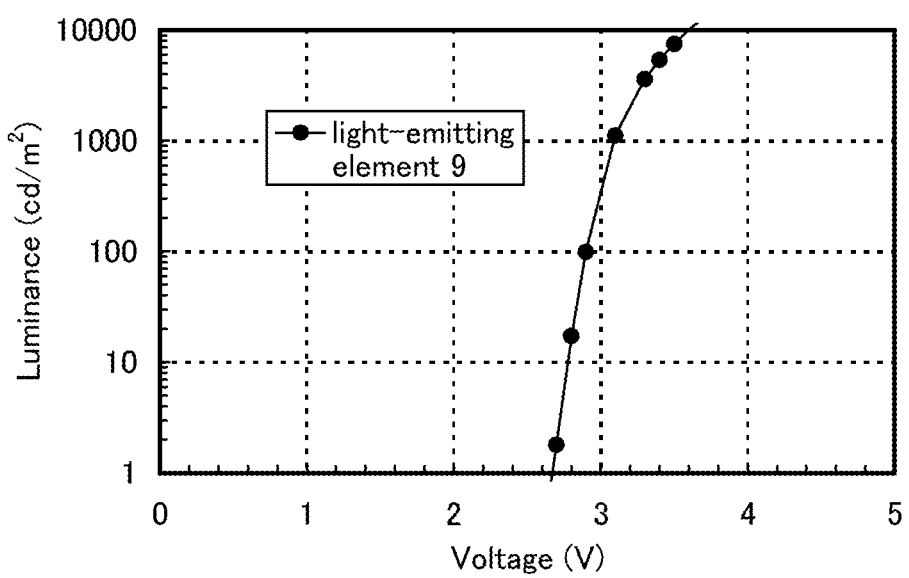
FIG. 36 shows luminance versus voltage characteristics of a light-emitting element of Example 9.
Figure 37:
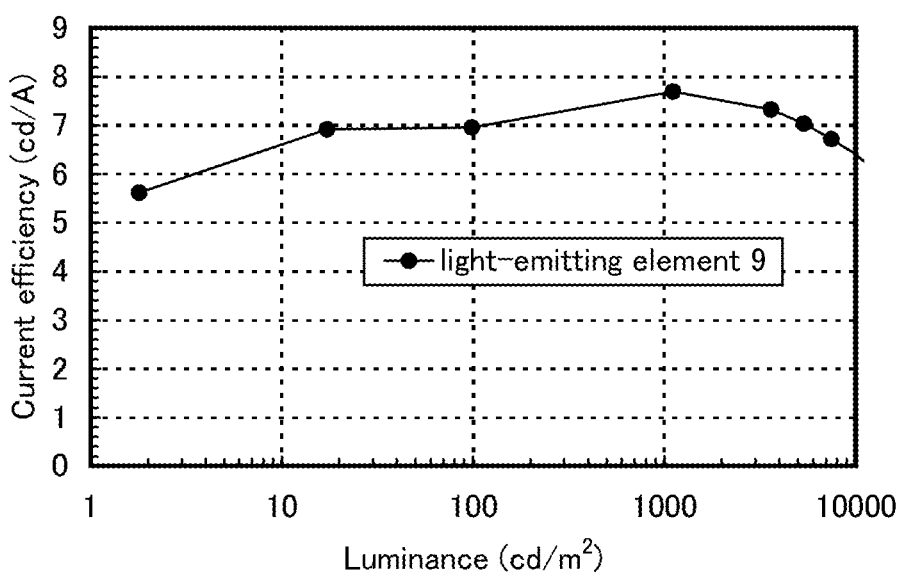
FIG. 37 shows current efficiency versus luminance characteristics of the light-emitting element of Example 9.

The luminance versus voltage characteristics of the light-emitting element 9 are shown in FIG. 36. In FIG. 36, the horizontal axis represents voltage (V) and the vertical axis represents luminance (cd/m$^2$). In addition, the current efficiency versus luminance characteristics of the element are shown in FIG. 37. In FIG. 37, the horizontal axis represents luminance (cd/m$^2$) and the vertical axis represents current efficiency (cd/A). Further, Table 16 shows the voltage (V), CIE chromaticity coordinates (x, y), current efficiency (cd/A), and external quantum efficiency (%) of the light-emitting element 9 at a luminance of 1100 cd/m$^2$.

TABLE 16

|  | Voltage (V) | Chromaticity coordinates (x, y) | Luminance (cd/m$^2$) | Current efficiency (cd/A) | External quantum efficiency (%) |
| --- | --- | --- | --- | --- | --- |
| Light-emitting element 9 | 3.1 | (0.14, 0.18) | 1100 | 7.7 | 5.8 |

As shown in Table 16, the CIE chromaticity coordinates of the light-emitting element 9 are (x, y)=(0.14, 0.18) at a luminance of 1100 cd/m$^2$. This result shows that blue light emission originating from 1,6mMemFLPAPrn was obtained from the light-emitting element 9.

As can be seen from FIG. 36 and FIG. 37, the light-emitting element 9 has a low driving voltage and high emission efficiency.

The above results suggest that an element having high emission efficiency can be achieved when the composite material of one embodiment of the present invention is used for the hole-injection layer of the light-emitting element. The results also suggest that a light-emitting element having a low driving voltage can be provided when the composite material of one embodiment of the present invention is used for the hole-injection layer of the light-emitting element. The results also suggest that a light-emitting element having a long lifetime can be manufactured when the composite material of one embodiment of the present invention is used for the hole-injection layer.

The experimental results of the light-emitting element 9 in this example show that the composite materials of embodiments of the present invention can be suitably used for a light-emitting element which exhibits blue fluorescence.

Example 10

In this example, a light-emitting element of one embodiment of the present invention is described with reference to FIG. 26A. The materials used in this example are the ones used in the above examples, and therefore the chemical formulae thereof are omitted here.

TABLE 15

|  | First electrode | Hole-injection layer | Hole-transport layer | Light-emitting layer | First electron-transport layer | Second electron-transport layer | Electron-injection layer | Second electrode |
| --- | --- | --- | --- | --- | --- | --- | --- | --- |
| Light-emitting element 9 | ITSO 110 nm | βN3P:MoOx (=4:2) 50 nm | PCzPA 10 nm | CzPA:1,6mMemFLPAPrn (=1:0.04) 30 nm | CzPA 10 nm | BPhen 15 nm | LiF 1 nm | Al 200 nm |

The way how a light-emitting element 10 of this example was fabricated is described below.
(Light-Emitting Element 10)

First, a film of ITSO was formed over a glass substrate 1100 by a sputtering method, so that the first electrode 1101 which functions as an anode was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface over which the first electrode 1101 was provided faced downward. The pressure in the vacuum evaporation apparatus was reduced to about $10^{-4}$ Pa. Then, P4N and molybdenum(VI) oxide were co-evaporated to form the hole-injection layer 1111 over the first electrode 1101. The thickness of the hole-injection layer 1111 was set to 40 nm, and the mass ratio of P4N to molybdenum oxide was adjusted to 4:2 (=P4N:molybdenum oxide).

Next, over the hole-injection layer 1111, a film of BPAFLP was formed to a thickness of 10 nm to form a hole-transport layer 1112.

Furthermore, 2mDBTPDBq-II, NPB, and [Ir(dppm)$_2$(acac)] were co-evaporated to form a light-emitting layer 1113 over the hole-transport layer 1112. Here, the mass ratio of 2mDBTPDBq-II to NPB and [Ir(dppm)$_2$(acac)] was adjusted to 0.8:0.2:0.05 (=2mDBTPDBq-II:NPB:[Ir(dppm)$_2$(acac)]). In addition, the thickness of the light-emitting layer 1113 was set to 40 nm.

Further, over the light-emitting layer 1113, a film of 2mDBTPDBq-II was formed to a thickness of 10 nm to form the first electron-transport layer 1114a.

Then, over the first electron-transport layer 1114a, a film of BPhen was formed to a thickness of 20 nm to form the second electron-transport layer 1114b.

Further, over the second electron-transport layer 1114b, a film of LiF was formed by evaporation to a thickness of 1 nm to form the electron-injection layer 1115.

Lastly, an aluminum film was formed by evaporation to a thickness of 200 nm as the second electrode 1103 functioning as a cathode. Thus, the light-emitting element 10 of this example was fabricated.

Note that, in all the above evaporation steps, evaporation was performed by a resistance-heating method.

Table 17 shows element structures of the light-emitting element 10 obtained as described above.

In a glove box containing a nitrogen atmosphere, the light-emitting element 10 was sealed so as not to be exposed to the air. Then, operation characteristics of the light-emitting element 10 were measured. Note that the measurements were carried out at room temperature (in an atmosphere kept at 25° C.).

Figure 38:
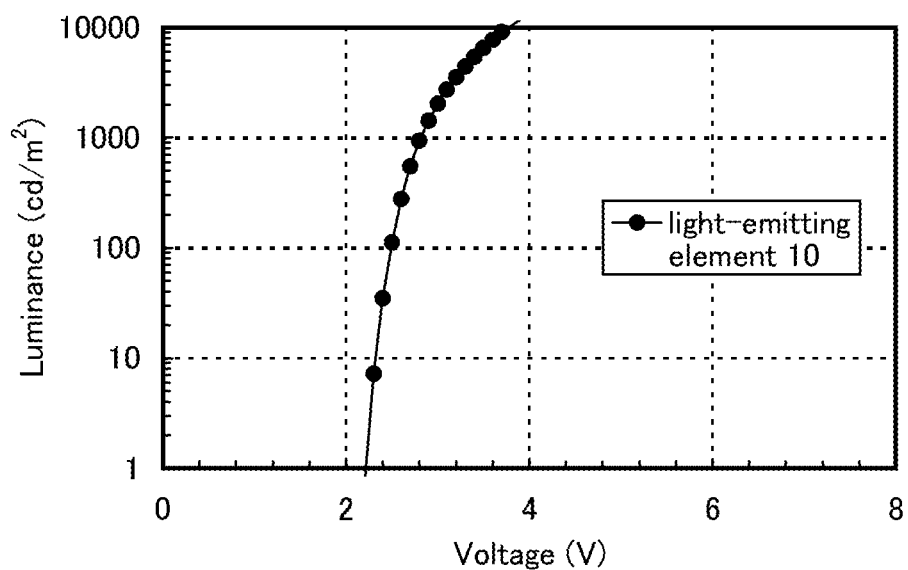
FIG. 38 shows luminance versus voltage characteristics of a light-emitting element of Example 10.
Figure 39:
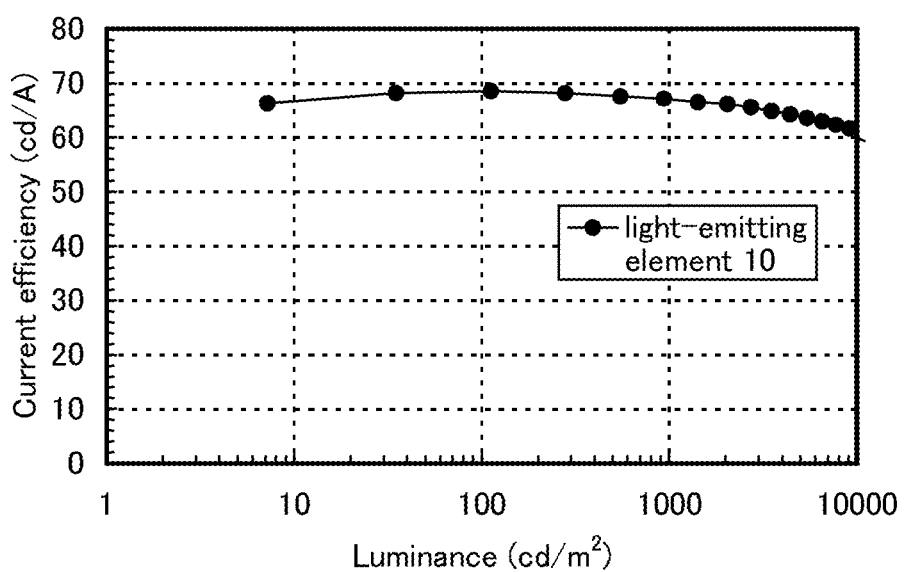
FIG. 39 shows current efficiency versus luminance characteristics of the light-emitting element of Example 10.

The luminance versus voltage characteristics of the light-emitting element 10 are shown in FIG. 38. In FIG. 38, the horizontal axis represents voltage (V) and the vertical axis represents luminance (cd/m$^2$). In addition, the current efficiency versus luminance characteristics of the element are shown in FIG. 39. In FIG. 39, the horizontal axis represents luminance (cd/m$^2$) and the vertical axis represents current efficiency (cd/A). Further, Table 18 shows the voltage (V), CIE chromaticity coordinates (x, y), current efficiency (cd/A), and external quantum efficiency (%) of the light-emitting element 10 at a luminance of 940 cd/m$^2$.

TABLE 18

|  | Voltage (V) | Chromaticity coordinates (x, y) | Luminance (cd/m$^2$) | Current efficiency (cd/A) | External quantum efficiency (%) |
| --- | --- | --- | --- | --- | --- |
| Light-emitting element 10 | 2.8 | (0.57, 0.42) | 940 | 67 | 28 |

As shown in Table 18, the CIE chromaticity coordinates of the light-emitting element 10 are (x, y)=(0.57, 0.42) at a luminance of 940 cd/m$^2$. This shows that orange light emission originating from [Ir(dppm)$_2$(acac)] was obtained from the light-emitting element 10.

As can be seen from FIG. 38 and FIG. 39, the light-emitting element 10 has a low driving voltage and high emission efficiency. In addition, the light-emitting element 10 is found to have an extremely high external quantum efficiency at a luminance of 940 cd/m$^2$, which is 28%.

Figure 40:
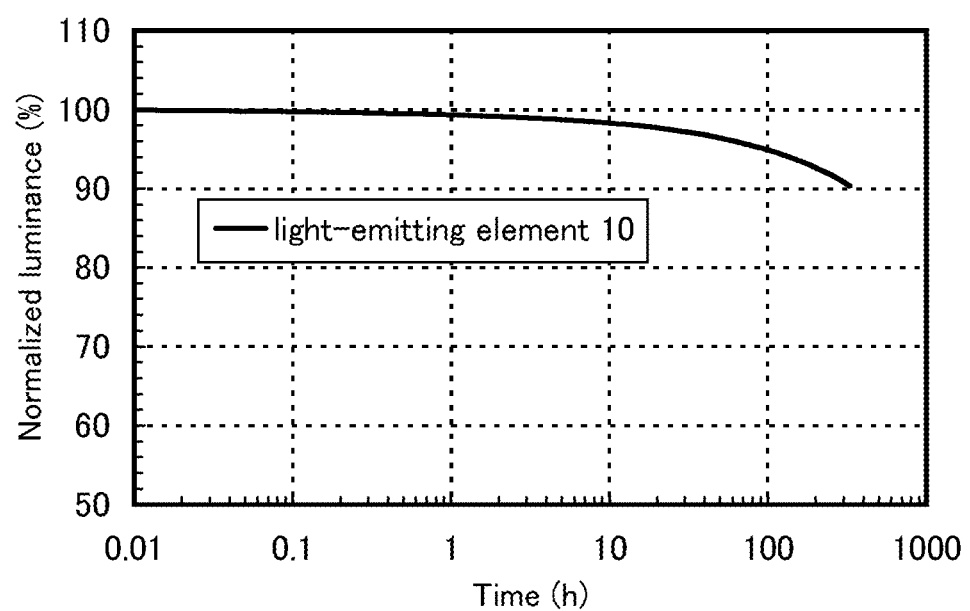
FIG. 40 shows results of a reliability test of the light-emitting element of Example 10.

Next, the light-emitting element was subjected to a reliability test. Results of the reliability test are shown in FIG. 40. In FIG. 40, the vertical axis represents normalized luminance (%) with an initial luminance of 100% and the horizontal axis represents driving time (h) of the element.

In the reliability test, the light-emitting element of this example was driven under the conditions where the initial luminance was set to 5000 cd/m$^2$ and the current density was constant.

FIG. 40 shows that the light-emitting element 10 kept 90% of the initial luminance after 330 hours elapsed. It is found that the light-emitting element 10 to which one embodiment of the present invention is applied has a long lifetime and high reliability.

The above results suggest that an element having high emission efficiency can be achieved when the composite material of one embodiment of the present invention is used for the hole-injection layer of the light-emitting element which exhibits phosphorescence. The results also suggest

TABLE 17

|  | First electrode | Hole-injection layer | Hole-transport layer | Light-emitting layer | First electron-transport layer | Second electron-transport layer | Electron-injection layer | Second electrode |
| --- | --- | --- | --- | --- | --- | --- | --- | --- |
| Light-emitting element 10 | ITSO 110 nm | P4N:MoOx (=4:2) 40 nm | BPAFLP 10 nm | 2mDBTPDBq-II: NPB: [Ir(dppm)$_2$(acac)] (=0.8:0.2:0.05) 40 nm | 2mDBTPDBq-II 10 nm | BPhen 20 nm | LiF 1 nm | Al 200 nm | that a light-emitting element having a low driving voltage can be provided when the composite material of one embodiment of the present invention is used for the hole-injection layer of the light-emitting element which exhibits phosphorescence. The results also suggest that a light-emitting element having a long lifetime can be manufactured when the composite material of one embodiment of the present invention is used for the hole-injection layer of the light-emitting element which exhibits phosphorescence.

Further, the results suggest that the composite material of one embodiment of the present invention can be suitably used for the hole-injection layer of the light-emitting element which exhibits orange phosphorescence. It is thus found that the composite material can be suitably used for a light-emitting element which exhibits orange light or light having a longer wavelength than orange light.

Example 11

In this example, 9,9'-(biphenyl-3,3'-diyl)-di-phenanthrene (abbreviation: mPnBP), which is a hydrocarbon compound that can be used for the composite material of one embodiment of the present invention, is described. A structural formula of mPnBP is illustrated below.

[Chemical Formula 30]

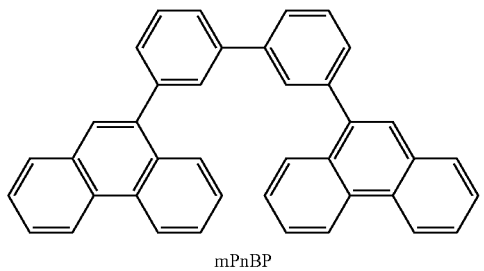

mPnBP

Figure 41A:
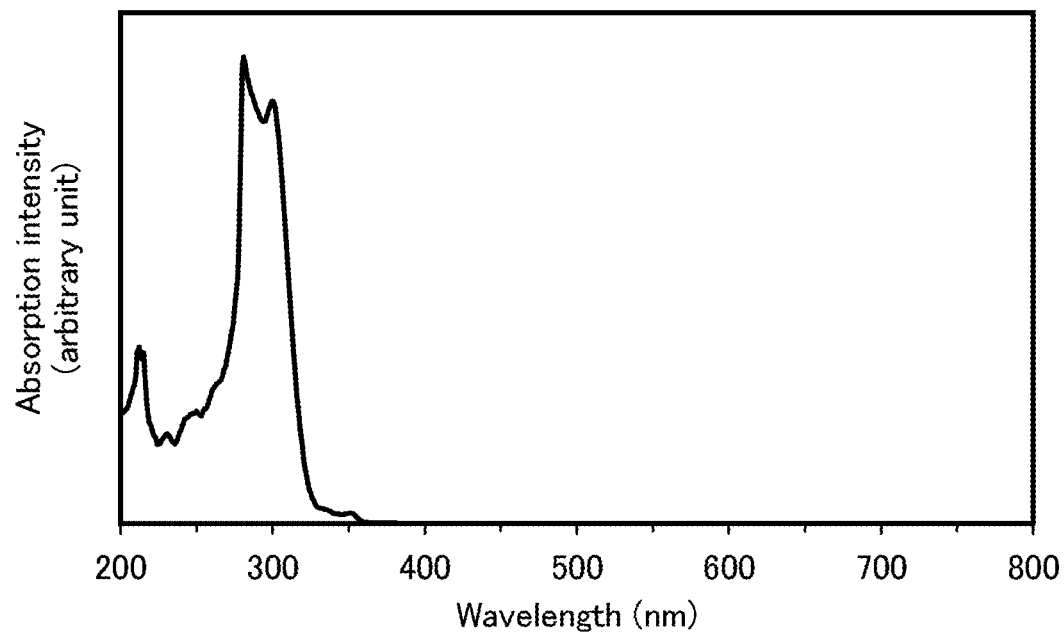
FIGS. 41A and 41B show an absorption and emission spectra of mPnBP in a toluene solution of mPnBP.
Figure 41B:
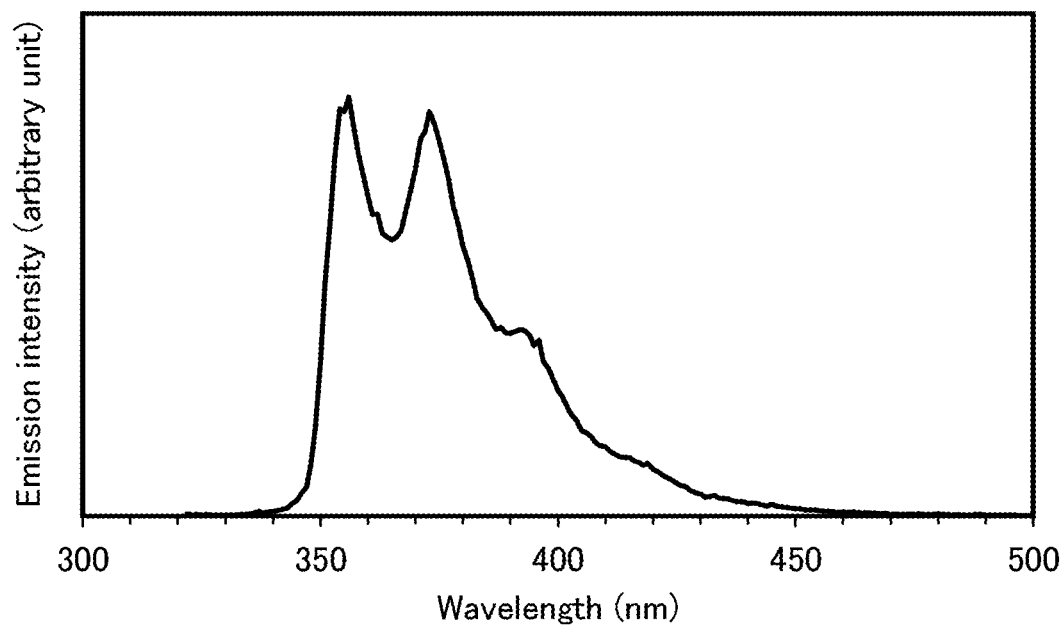

Further, FIG. 41A shows an absorption spectrum of mPnBP in a toluene solution of mPnBP, and FIG. 41B shows an emission spectrum thereof. The absorption spectrum was measured using an ultraviolet-visible spectrophotometer (V-550, produced by JASCO Corporation). The measurements were performed in such a way that each solution was put in a quartz cell. Here is shown the absorption spectrum which was obtained by subtraction of the absorption spectra of quartz and toluene from those of quartz and the solution. In FIG. 41A, the horizontal axis represents wavelength (nm) and the vertical axis represents absorption intensity (arbitrary unit). In FIG. 41B, the horizontal axis represents wavelength (nm) and the vertical axis represents emission intensity (arbitrary unit). Further, mPnBP exhibits an absorption peak at around 282 nm, 298 nm, and 348 nm and an emission wavelength peak at 356 nm, 373 nm, and 394 nm (at an excitation wavelength of 306 nm).

It is thus found from the absorption spectrum of mPnBP in a toluene solution, that no absorption spectrum in the visible light region is observed and therefore mPnBP is suitable as the hydrocarbon compound used for the composite material of one embodiment of the present invention. In addition, since the emission peaks are located at the shorter wavelengths, the hydrocarbon compound is suitable for a material of a hole-transport layer in contact with the light-emitting layer or for a host material of a light-emitting layer.

Reference Example 1

A synthesis example in which 3-[4-(1-naphthyl)-phenyl]-9-phenyl-9H-carbazole (abbreviation: PCPN) used in the above example was prepared is described.

[Chemical Formula 31]

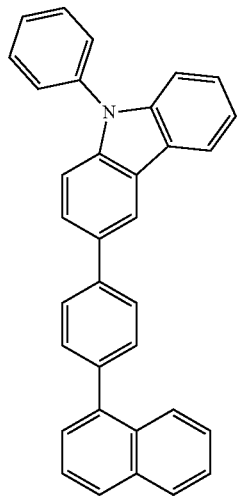

PCPN

A synthesis scheme of PCPN is illustrated in (a-1).

[Chemical Formula 32]

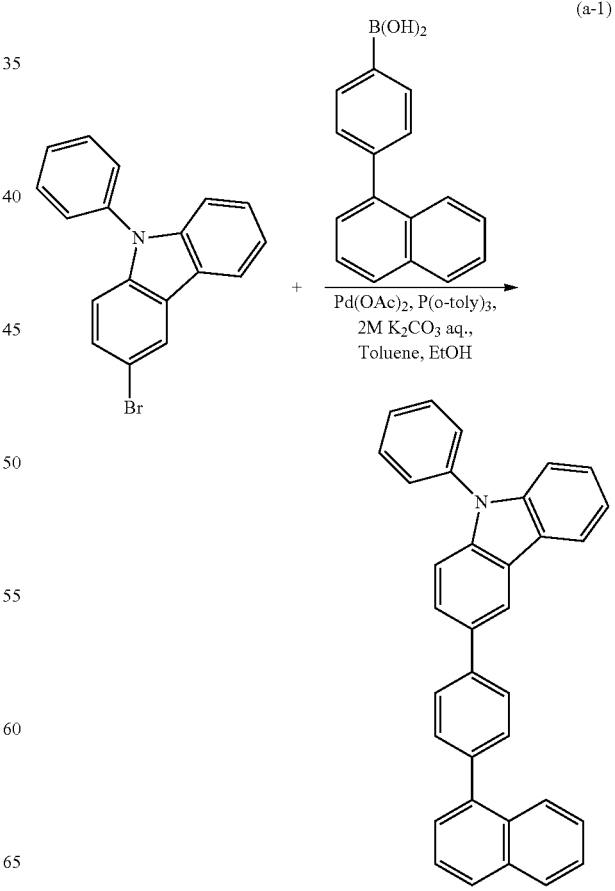

(a-1)

In a 200 mL three-neck flask, a mixture of 5.0 g (15.5 mmol) of 3-bromo-9-phenyl-9H-carbazole, 4.2 g (17.1 mmol) of 4-(1-naphthyl)-phenylboronic acid, 38.4 mg (0.2 mmol) of palladium(II) acetate, 104 mg (0.3 mmol) of tri(ortho-tolyl)phosphine, 50 mL of toluene, 5 mL of ethanol, and 30 mL of a 2 mol/L aqueous potassium carbonate solution was degassed while being stirred under reduced pressure, and reacted by being stirred and heated at 85° C. for 9 hours under a nitrogen atmosphere.

After the reaction, 500 mL of toluene was added to this reaction mixture solution, and the organic layer of this mixture solution was filtered through Florisil (produced by Wako Pure Chemical Industries, Ltd., Catalog No. 540-00135), alumina, and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and methanol was added thereto. The mixture was irradiated with ultrasonic waves and then recrystallized to give 6.24 g of a white powder in a yield of 90%, which was the object of the synthesis.

This compound was identified as 3-[4-(1-naphthyl)-phenyl]-9-phenyl-9H-carbazole (abbreviation: PCPN), which was the object of the synthesis, by nuclear magnetic resonance ($^1$H-NMR) spectroscopy.

$^1$H NMR data of the obtained substance are as follows: $^1$H NMR (CDCl$_3$, 300 MHz): δ (ppm)=7.30-7.35 (m, 1H), 7.44-7.67 (m, 14H), 7.76 (dd, J=8.7 Hz, 1.8 Hz, 1H), 7.84-7.95 (m, 4H), 8.04 (d, J=7.8, 1H), 8.23 (d, J=7.8, 1H), 8.46 (d, J=1.5, 1H).

Reference Example 2

A method of synthesizing 2-[3-(dibenzothiophen-4-yl)phenyl]dibenzo[f,h]quinoxaline (abbreviation: 2mDBTP-DBq-II), which was used in the above examples, is described.

[Chemical Formula 33]

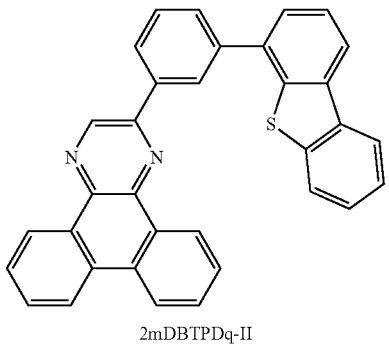

2mDBTPDq-II

A synthesis scheme of 2mDBTPDBq-II is shown in (b-1).

[Chemical Formula 34]

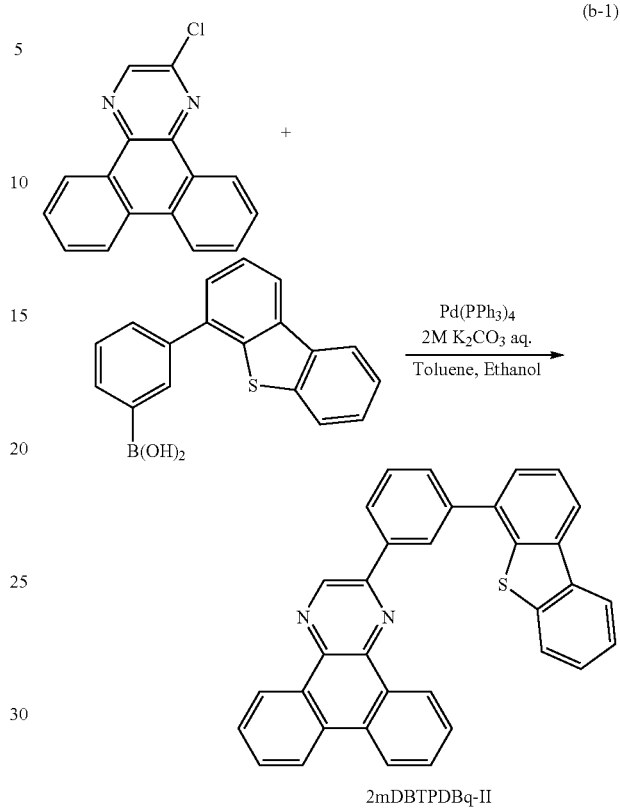

(b-1)

First, 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous solution of potassium carbonate were put in a 2 L three-neck flask. The mixture was degassed by being stirred under reduced pressure, and the air in the three-neck flask was replaced with nitrogen. This mixture was stirred under a nitrogen stream at 100° C. for 7.5 hours. After cooled to room temperature, the obtained mixture was filtered to give a white residue. The obtained residue was washed with water and ethanol in this order, and then dried. The obtained solid was dissolved in about 600 mL of hot toluene, followed by filtration through Celite and Florisil, so that a clear colorless filtrate was obtained. The obtained filtrate was concentrated and purified by silica gel column chromatography using silica gel. The chromatography was carried out using hot toluene as a developing solvent. Acetone and ethanol were added to the solid obtained here, followed by irradiation with ultrasonic waves. Then, the generated suspended solid was collected by filtration and the obtained solid was dried, so that 7.85 g of a white powder of the object of the synthesis was obtained in 80% yield.

By a train sublimation method, 4.0 g of the obtained white powder was purified. In the purification, the white powder was heated at 300° C. under a pressure of 5.0 Pa with a flow rate of argon gas of 5 mL/min. After the purification, the object of the synthesis was obtained in a yield of 88% as 3.5 g of a white powder.

A nuclear magnetic resonance ($^1$H NMR) spectroscopy identified this compound as 2-[3-(dibenzothiophen-4-yl)

phenyl]dibenzo[f,h]quinoxaline (abbreviation: 2mDBTP-DBq-II), which was the object of the synthesis.

¹H NMR data of the obtained substance are shown below.

¹H NMR (CDCl₃, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

Reference Example 3

Reference Example 3 shows a method of synthesizing N,N'-bis(3-methylphenyl)-N,N'-bis[3-(9-phenyl-9H-fluoren-9-yl)phenyl]-pyrene-1,6-diamine (abbreviation: 1,6mMemFLPAPm) used in the above Examples. The structural formula of 1,6mMemFLPAPm is shown below.

[Chemical Formula 35]

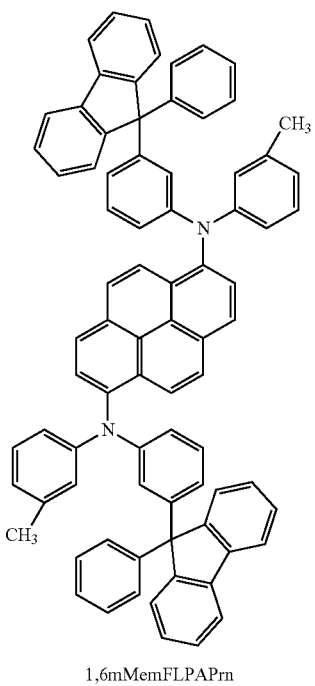

1,6mMemFLPAPm

Step 1: Synthesis Method of 3-Methylphenyl-3-(9-phenyl-9H-fluoren-9-yl)phenylamine (Abbreviation: mMemFLPA)

A synthesis scheme of Step 1 is illustrated in (c-1).

[Chemical Formula 36]

(c-1)

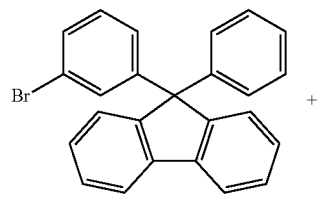

+

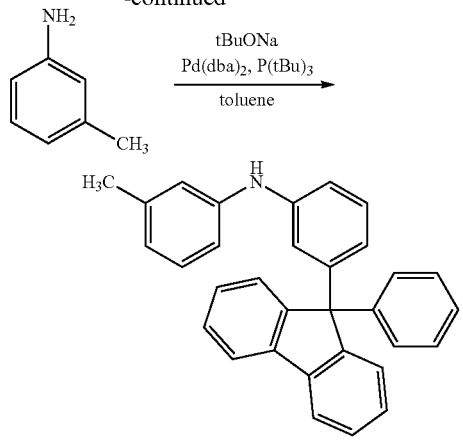

There were put 3.2 g (8.1 mmol) of 9-(3-bromophenyl)-9-phenylfluorene and 2.3 g (24.1 mmol) of sodium tert-butoxide in a 200 mL three-neck flask. The air in the flask was replaced with nitrogen. Then, 40.0 mL of toluene, 0.9 mL (8.3 mmol) of m-toluidine, and 0.2 mL of a 10% hexane solution of tri(tert-butyl)phosphine were added to this mixture. The temperature of this mixture was set to 60° C., and 44.5 mg (0.1 mmol) of bis(dibenzylideneacetone)palladium (0) was added to the mixture. The temperature of the mixture was raised to 80° C., followed by stirring for 2.0 hours. After the stirring, the mixture was suction-filtered through Florisil, Celite, and alumina to give a filtrate. The filtrate was concentrated to give a solid, which was then purified by silica gel column chromatography (with a developing solvent containing hexane and toluene in a 1:1 ratio). Recrystallization was performed from a mixed solvent of toluene and hexane. Accordingly, 2.8 g of a white solid of the object of the synthesis was obtained in 82% yield.

Step 2: Synthesis Method of 1,6mMemFLPAPm)

A synthesis scheme of Step 2 is illustrated in (c-2).

[Chemical Formula 37]

(c-2)

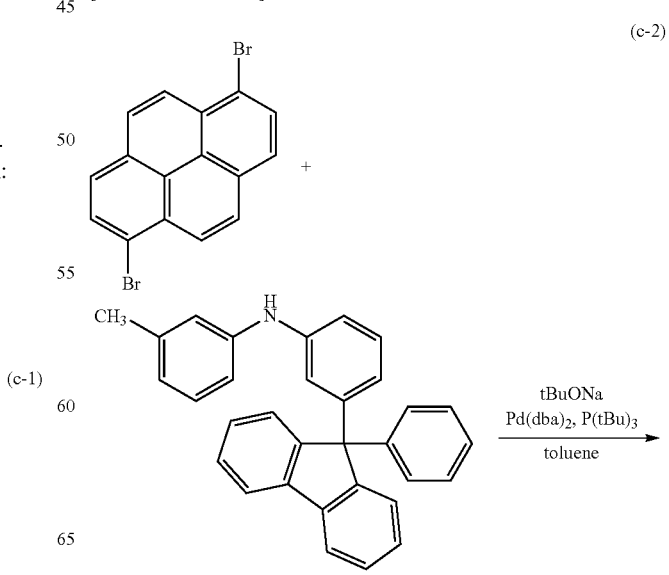

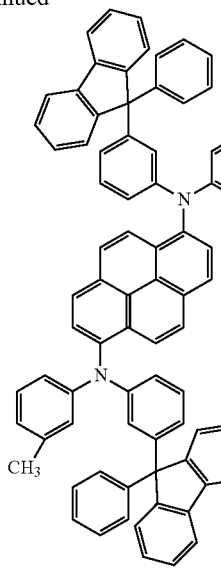

1,6mMemFLPAPrn

There were put 0.6 g (1.7 mmol) of 1,6-dibromopyrene, 1.4 g (3.4 mmol) of mMemFLPA obtained in Step 1 above, and 0.5 g (5.1 mmol) of sodium tert-butoxide in a 100 mL three-neck flask. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture. The temperature of this mixture was set to 80° C., followed by stirring for 3.0 hours. After the stirring, 400 mL of toluene was added to the mixture, and the mixture was heated. While the mixture was kept hot, it was suction-filtered through Florisil, Celite, and alumina to give a filtrate. The filtrate was concentrated to give a solid, which was then purified by silica gel column chromatography (with a developing solvent containing hexane and toluene in a 3:2 ratio) to give a yellow solid. Recrystallization of the obtained yellow solid from a mixed solvent of toluene and hexane gave 1.2 g of a yellow solid in 67% yield, which was the object of the synthesis.

By a train sublimation method, 1.0 g of the obtained yellow solid was purified. In the purification, the yellow solid was heated at 317° C. under a pressure of 2.2 Pa with a flow rate of argon gas of 5.0 mL/min. After the purification, 1.0 g of a yellow solid of the object of the synthesis was obtained in 93% yield.

A nuclear magnetic resonance (NMR) spectroscopy and a mass spectrometry identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPm), which was the object of the synthesis.

$^1$H NMR data of the obtained compound is shown below.

$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

Reference Example 4

A synthetic example of (acetylacetonato)bis(6-tert-butyl-4-phenylpyrimidinato)iridium(III) (abbreviation: [Ir(tBuppm)$_2$(acac)]), which was used in the above examples, is described.

[Chemical Formula 38]

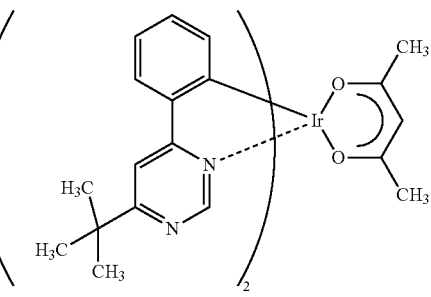

[Ir(tBuppm)$_2$(acac)]

Synthesis of 4-tert-Butyl-6-phenylpyrimidine
(Abbreviation: HtBuppm)

A synthesis scheme of Step 1 is shown in (d-1) given below.

[Chemical Formula 39]

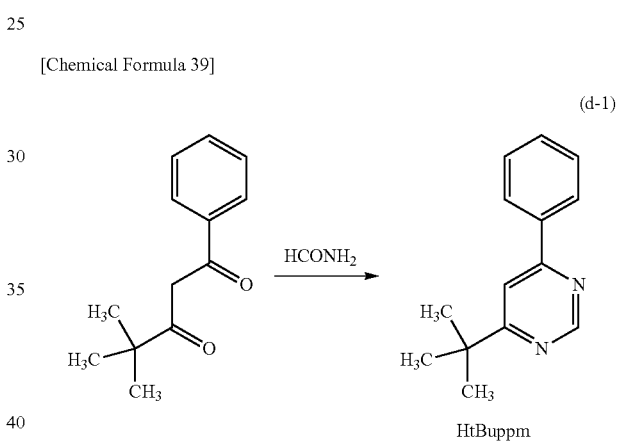

(d-1)

HtBuppm

First, 22.5 g of 4,4-dimethyl-1-phenylpentane-1,3-dione and 50 g of formamide were put into a recovery flask equipped with a reflux pipe, and the air in the flask was replaced with nitrogen. This reaction container was heated, so that the reacted solution was refluxed for 5 hours. After that, this solution was poured into an aqueous solution of sodium hydroxide, and an organic layer was extracted with dichloromethane. The obtained organic layer was washed with water and saturated saline, and dried with magnesium sulfate. The solution after drying was filtered. The solvent of this solution was distilled off, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained.

Step 2: Synthesis of Di-µ-chloro-bis[bis(6-tert-butyl-4-phenylpyrimidinato)iridium(III)](Abbreviation: [Ir(tBuppm)$_2$Cl]$_2$)

A synthesis scheme of Step 2 is shown in (d-2) given below.

[Chemical Formula 40]

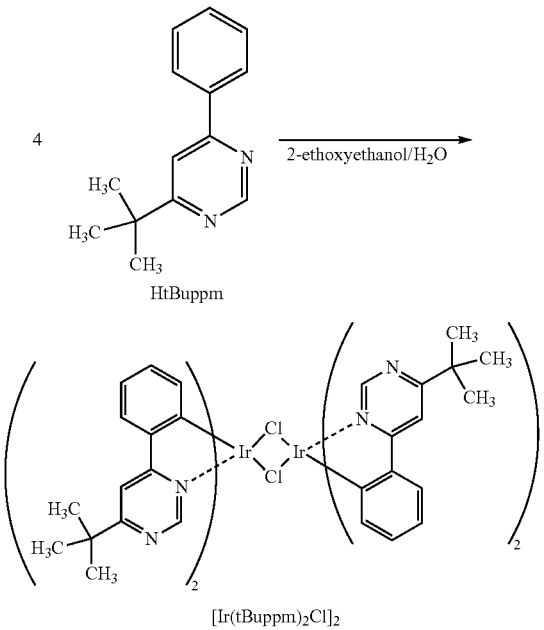

Next, 15 mL of 2-ethoxyethanol, 5 mL of water, 1.49 g of HtBuppm obtained in Step 1, and 1.04 g of iridium chloride hydrate (IrCl₃.H₂O) were put into a recovery flask equipped with a reflux pipe, and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol, so that a dinuclear complex [Ir(tBuppm)₂Cl]₂ (yellow green powder, yield of 73%) was obtained.

Step 3: Synthesis of [Ir(tBuppm)₂(acac)]

A synthesis scheme of Step 3 is shown in (d-3) given below.

[Chemical Formula 41]

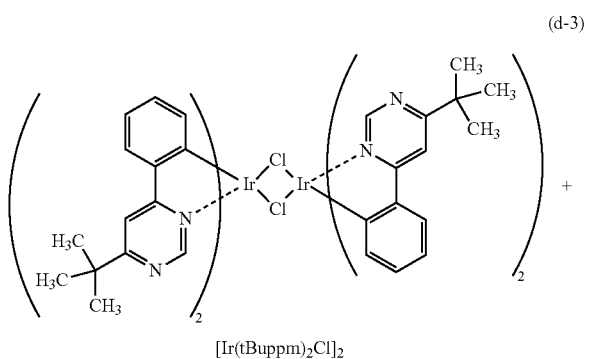

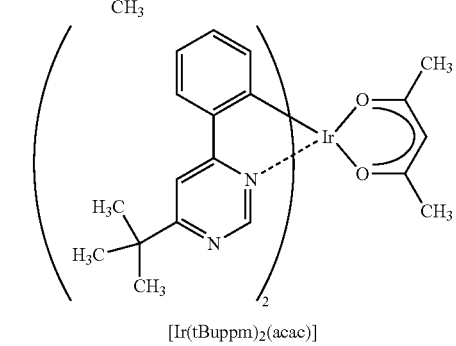

Further, 40 mL of 2-ethoxyethanol, 1.61 g of the dinuclear complex [Ir(tBuppm)₂Cl]₂ obtained in Step 2, 0.36 g of acetylacetone, and 1.27 g of sodium carbonate were put into a recovery flask equipped with a reflux pipe, and the air in the flask was replaced with argon. After that, irradiation with microwaves (2.45 GHz, 120 W) was performed for 60 minutes to cause a reaction. The solvent was distilled off, and the obtained residue was suction-filtered with ethanol and washed with water and ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized with a mixed solvent of dichloromethane and hexane, so that the object of the synthesis was obtained as yellow powder (yield of 68%).

An analysis result by nuclear magnetic resonance (¹H NMR) spectroscopy of the yellow powder obtained in Step 3 is described below. These results show that [Ir(tBuppm)₂(acac)] was obtained in this synthesis example.

¹H NMR. δ (CDCl₃): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

Reference Example 5

A synthetic example of an organometallic complex (acetylacetonato)bis(4,6-diphenylpyrimidinato)iridium(III) (abbreviation: [Ir(dppm)₂(acac)]), which was used in the above examples, is described.

[Chemical Formula 42]

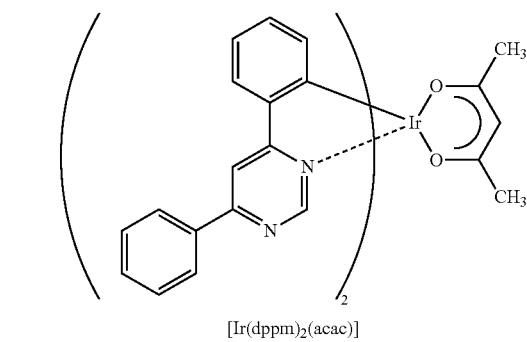

Step 1: Synthesis of 4,6-Diphenylpyrimidine (Abbreviation: Hdppm)

First, 5.02 g of 4,6-dichloropyrimidine, 8.29 g of phenylboronic acid, 7.19 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile were put into a recovery flask equipped with a reflux pipe, and the air in the flask was replaced with argon. This reaction container was heated by irradiation with microwaves (2.45 GHz, 100 W) for 60 minutes. Here, there were further put 2.08 g of phenylboronic acid, 1.79 g of sodium carbonate, 0.070 g of Pd(PPh$_3$)$_2$Cl$_2$, 5 mL of water, and 5 mL of acetonitrile into the flask, and the mixture was heated again by irradiation with microwaves (2.45 GHz, 100 W) for 60 minutes. After that, water was added to this solution and an organic layer was extracted with dichloromethane. The obtained solution of the extract was washed with water and dried with magnesium sulfate. The solution after drying was filtered. The solvent of this solution was distilled off, and then the obtained residue was purified by silica gel column chromatography using dichloromethane as a developing solvent, so that a pyrimidine derivative Hdppm (yellow white powder, yield of 38%) was obtained. Note that for the microwave irradiation, a microwave synthesis system (Discover, manufactured by CEM Corporation) was used. A synthesis scheme (e-1) of Step 1 is illustrated below.

[Chemical Formula 43]

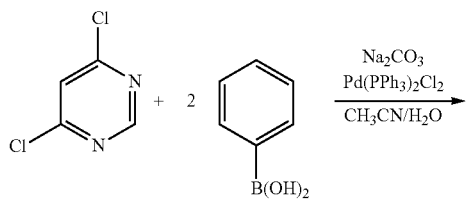

(e-1)

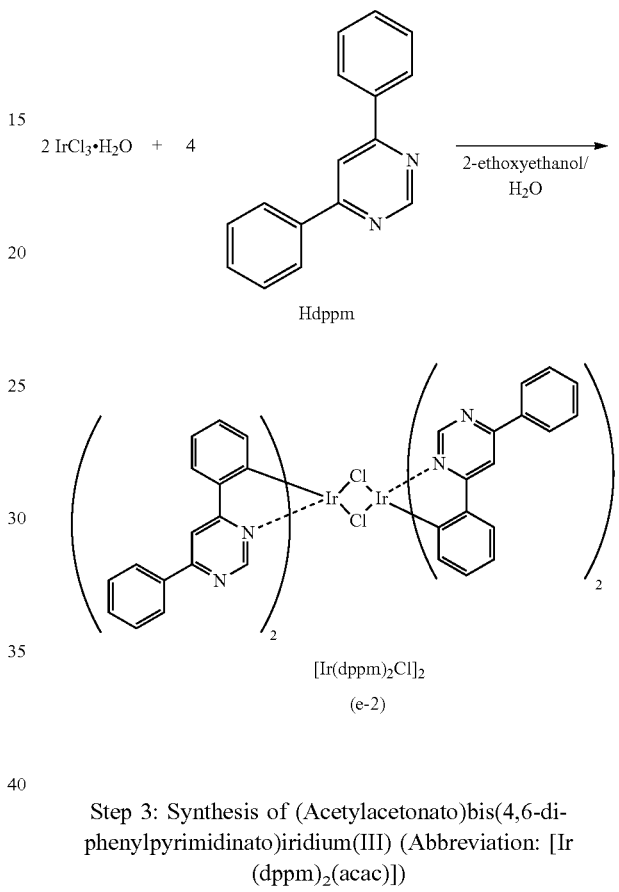

Step 2: Synthesis of Di-μ-chloro-bis[bis(4,6-diphenylpyrimidinato)iridium(III)](Abbreviation: [Ir(dppm)$_2$Cl]$_2$)

Next, 15 mL of 2-ethoxyethanol, 5 mL of water, 1.10 g of Hdppm obtained in Step 1, and 0.69 g of iridium chloride hydrate (IrCl$_3$·H$_2$O) were put into a recovery flask equipped with a reflux pipe, and the air in the recovery flask was replaced with argon. After that, irradiation with microwaves (2.45 GHz, 100 W) was performed for 1 hour to cause a reaction. The solvent was distilled off, and then the obtained residue was filtered and washed with ethanol to give a dinuclear complex [Ir(dppm)$_2$Cl]$_2$ (reddish brown powder, yield of 88%). A synthesis scheme (e-2) of Step 2 is illustrated below.

[Chemical Formula 44]

Step 3: Synthesis of (Acetylacetonato)bis(4,6-diphenylpyrimidinato)iridium(III) (Abbreviation: [Ir(dppm)$_2$(acac)])

Furthermore, 40 mL of 2-ethoxyethanol, 1.44 g of [Ir(dppm)$_2$Cl]$_2$ obtained in Step 2, 0.30 g of acetylacetone, and 1.07 g of sodium carbonate were put into a recovery flask equipped with a reflux pipe, and the air in the recovery flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove insoluble matter. The obtained filtrate was washed with water and then with saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a volume ratio of 50:1. After that, recrystallization was carried out with a mixed solvent of dichloromethane and hexane, so that an orange powder (yield of 32%), which was the object of the synthesis, was obtained. A synthesis scheme (e-3) of Step 3 is illustrated below.

[Chemical Formula 45]

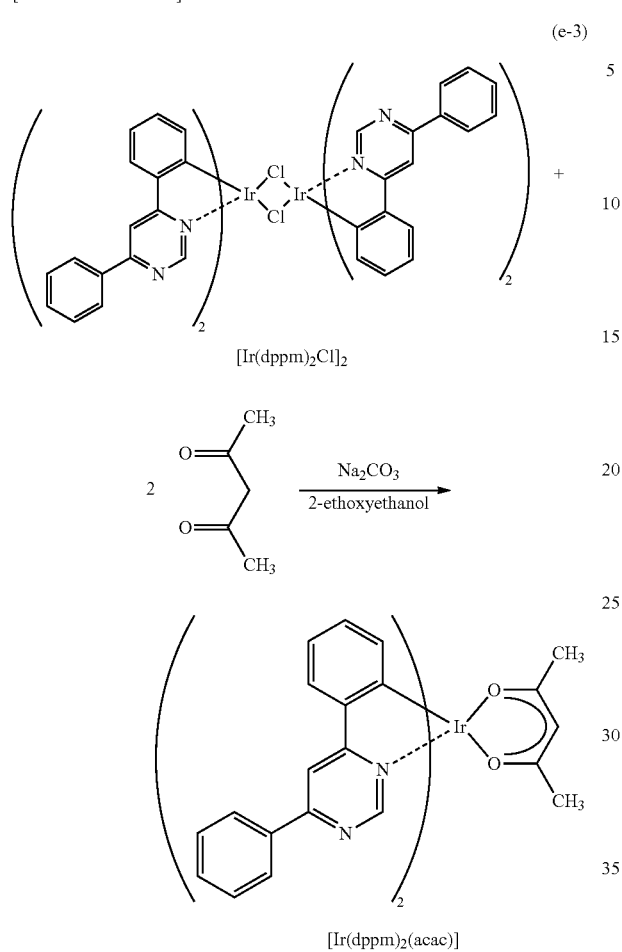

An analysis result by nuclear magnetic resonance ($^1$H NMR) spectroscopy of the orange powder obtained in Step 3 above is described below. These results show that [Ir(dppm)$_2$(acac)] was obtained in this synthesis example.

$^1$H NMR. δ (CDCl$_3$): 1.83 (s, 6H), 5.29 (s, 1H), 6.48 (d, 2H), 6.80 (t, 2H), 6.90 (t, 2H), 7.55-7.63 (m, 6H), 7.77 (d, 2H), 8.17 (s, 2H), 8.24 (d, 4H), 9.17 (s, 2H).

This application is based on Japanese Patent Application Serial No. 2011-064629 filed with the Japan Patent Office on Mar. 23, 2011 and Japanese Patent Application Serial No. 2011-122829 filed with the Japan Patent Office on May 31, 2011, the entire contents of which are hereby incorporated by reference.

What is claimed is:

1. A light-emitting device comprising:
a first electrode and a second electrode; and
a layer comprising a composite material between the first electrode and the second electrode,
wherein the composite material comprises a hydrocarbon compound of which a molecular weight is in a range of 350 or more and 2000 or less and molybdenum oxide,
wherein the hydrocarbon compound is represented by a general formula (G1):

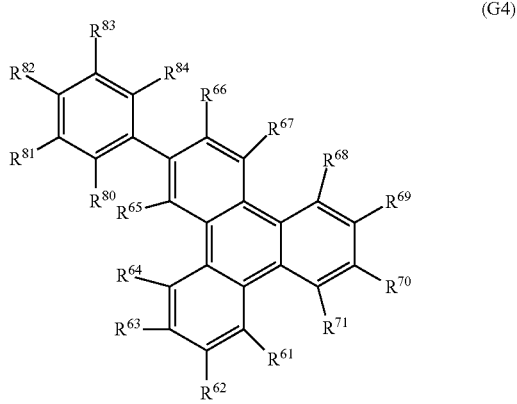

(G1)

wherein $R^1$ to $R^9$ independently represent any of hydrogen, an alkyl group having 1 to 4 carbon atoms, and an aryl group having 6 to 25 carbon atoms in a ring,
wherein one or more of $R^{19}$ to $R^{14}$ independently represent any of a substituted or unsubstituted phenyl group, a substituted or unsubstituted naphthyl group, a substituted or unsubstituted phenanthryl group, and a substituted or unsubstituted triphenylenyl group, and
wherein the other or others of $R^{19}$ to $R^{14}$ independently represent any of hydrogen, and an alkyl group having 1 to 6 carbon atoms.

2. A light-emitting device comprising:
a first electrode and a second electrode; and
a layer comprising a composite material between the first electrode and the second electrode,
wherein the composite material comprises a hydrocarbon compound of which a molecular weight is in a range of 350 or more and 2000 or less and molybdenum oxide,
wherein the hydrocarbon compound is represented by a general formula (G4):

(G4)

wherein $R^{61}$ to $R^{71}$ independently represent hydrogen, an alkyl group having 1 to 4 carbon atoms, or an aryl group having 6 to 25 carbon atoms in a ring,
wherein one or more of $R^{80}$ to $R^{84}$ independently represent a substituted or unsubstituted phenyl group, a substituted or unsubstituted naphthyl group, a substituted or unsubstituted phenanthryl group, or a substituted or unsubstituted triphenylenyl group, and
wherein the other or others of $R^{80}$ to $R^{84}$ independently represent hydrogen, and an alkyl group having 1 to 6 carbon atoms.

3. The light-emitting device according to claim 1, wherein the hydrocarbon compound has an absorption peak at a shorter wavelength than a visible-light wavelength.

4. The light-emitting device according to claim 1, wherein the hydrocarbon compound has an absorption peak at shorter than 380 nm.

5. The light-emitting device according to claim 1, further comprising a light-emitting layer between the first electrode and the second electrode.

6. An electronic device comprising the light-emitting device according to claim 1 in a display portion.

7. A lighting device comprising the light-emitting device according to claim 1 in a lighting portion.

8. The light-emitting device according to claim 2, wherein the hydrocarbon compound has an absorption peak at a shorter wavelength than a visible-light wavelength.

9. The light-emitting device according to claim 2, wherein the hydrocarbon compound has an absorption peak at shorter than 380 nm.

10. The light-emitting device according to claim 2, further comprising a light-emitting layer between the first electrode and the second electrode.

11. An electronic device comprising the light-emitting device according to claim 2 in a display portion.

12. A lighting device comprising the light-emitting device according to claim 2 in a lighting portion.

* * * * *